US012630868B2

(12) United States Patent
Cai et al.

(10) Patent No.: US 12,630,868 B2
(45) Date of Patent: *May 19, 2026

(54) MULTIPLEX LABELING OF MOLECULES BY SEQUENTIAL HYBRIDIZATION BARCODING

(71) Applicant: CALIFORNIA INSTITUTE OF TECHNOLOGY, Pasadena, CA (US)

(72) Inventors: Long Cai, Pasadena, CA (US); Eric Lubeck, Pasadena, CA (US); Timur Zhiyentayev, Pasadena, CA (US); Ahmet Coskun, Pasadena, CA (US); Ting-Fang He, Pasadena, CA (US); Chang Ho Sohn, Pasadena, CA (US); Sheel Shah, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 920 days.

This patent is subject to a terminal disclaimer.

(21) Appl. No.: 17/940,356

(22) Filed: Sep. 8, 2022

(65) Prior Publication Data

US 2023/0212658 A1     Jul. 6, 2023

Related U.S. Application Data

(63) Continuation of application No. 16/572,511, filed on Sep. 16, 2019, now Pat. No. 11,473,129, which is a continuation of application No. 14/435,735, filed as application No. PCT/US2014/036258 on Apr. 30, 2014, now Pat. No. 10,457,980.

(60) Provisional application No. 61/971,974, filed on Mar. 28, 2014, provisional application No. 61/817,651, filed on Apr. 30, 2013.

(51) Int. Cl.
| | |
|---|---|
| *C12Q 1/6841* | (2018.01) |
| *C12N 15/10* | (2006.01) |
| *G01N 21/64* | (2006.01) |
| *G02B 21/06* | (2006.01) |
| *G02B 21/16* | (2006.01) |

(52) U.S. Cl.
CPC ....... *C12Q 1/6841* (2013.01); *C12N 15/1065* (2013.01); *G01N 21/6428* (2013.01); *G01N 21/6458* (2013.01); *G02B 21/06* (2013.01); *G02B 21/16* (2013.01); *G01N 2201/068* (2013.01); *G01N 2201/10* (2013.01)

(58) Field of Classification Search
CPC .... C12Q 1/68; C12Q 2537/143; G01N 21/64; G01N 33/53
See application file for complete search history.

(56) References Cited

U.S. PATENT DOCUMENTS

| | | | |
|---|---|---|---|
| 5,364,763 A | 11/1994 | Kacian | |
| 5,367,066 A | 11/1994 | Urdea et al. | |
| 5,424,413 A | 6/1995 | Hogan et al. | |
| 5,629,147 A | 5/1997 | Asgari et al. | |
| 5,866,331 A | 2/1999 | Singer et al. | |
| 5,955,272 A | 9/1999 | Lawrence et al. | |
| 6,194,146 B1 | 2/2001 | Utermohlen et al. | |
| 6,534,266 B1 | 3/2003 | Singer | |
| 6,537,755 B1 | 3/2003 | Drmanac | |
| 7,033,758 B2 * | 4/2006 | Kenny | C12Q 1/682 |
| | | | 536/23.1 |
| 7,189,509 B2 | 3/2007 | Shao et al. | |
| 7,727,720 B2 | 6/2010 | Dhallan | |
| 8,309,306 B2 | 11/2012 | Nolan et al. | |
| 8,741,566 B2 | 6/2014 | Winther et al. | |
| 10,457,980 B2 * | 10/2019 | Cai | C12N 15/1065 |
| 10,961,566 B2 | 3/2021 | Chee | |
| 11,473,129 B2 * | 10/2022 | Cai | G01N 21/6428 |
| 12,305,224 B2 * | 5/2025 | Cai | G02B 21/06 |
| 12,421,540 B2 * | 9/2025 | Cai | C12Q 1/6841 |
| 2001/0019835 A1 | 9/2001 | Usui | |
| 2001/0026918 A1 | 10/2001 | Collins et al. | |
| 2002/0172950 A1 | 11/2002 | Kenny et al. | |
| 2002/0177130 A1 * | 11/2002 | Gray | C12Q 1/6886 |
| | | | 435/6.16 |
| 2003/0087279 A1 | 5/2003 | Shao et al. | |
| 2003/0129611 A1 | 7/2003 | Bao et al. | |
| 2003/0152490 A1 | 8/2003 | Trulson et al. | |
| 2003/0170613 A1 | 9/2003 | Straus | |
| 2004/0171075 A1 | 9/2004 | Flynn et al. | |
| 2004/0229253 A1 | 11/2004 | Hyldig-Nielsen et al. | |
| 2005/0064435 A1 | 3/2005 | Su et al. | |

(Continued)

FOREIGN PATENT DOCUMENTS

| | | |
|---|---|---|
| CN | 105392898 A | 3/2016 |
| EP | 0611828 A1 | 8/1994 |

(Continued)

OTHER PUBLICATIONS

Choi et al., Programmable in situ amplification for multiplexed imaging of mRNA expression. Nature Biotechnology 28(11) : 1208 (Year: 2010).*

(Continued)

*Primary Examiner* — Anne M. Gussow
(74) *Attorney, Agent, or Firm* — SQUIRE PATTON BOGGS (US) LLP

(57) ABSTRACT

The present invention, among other things, provides technologies for detecting and/or quantifying nucleic acids in cells, tissues, organs or organisms. In some embodiments, through sequential barcoding, the present invention provides methods for high-throughput profiling of a large number of targets, such as transcripts and/or DNA loci.

47 Claims, 27 Drawing Sheets

(56)                References Cited

U.S. PATENT DOCUMENTS

| | | | |
|---|---|---|---|
| 2005/0069895 A1 | 3/2005 | Woudenberg et al. | |
| 2006/0275782 A1 | 12/2006 | Gunderson et al. | |
| 2008/0108094 A1* | 5/2008 | Holdenrieder | G01N 33/5308 |
| | | | 435/7.92 |
| 2008/0269068 A1 | 10/2008 | Church et al. | |
| 2009/0081688 A1 | 3/2009 | Luo et al. | |
| 2010/0047924 A1 | 2/2010 | Webster et al. | |
| 2010/0221708 A1 | 9/2010 | Yamada et al. | |
| 2010/0304994 A1 | 12/2010 | Wu et al. | |
| 2010/0323348 A1 | 12/2010 | Hamady et al. | |
| 2011/0104676 A1 | 5/2011 | Pierce et al. | |
| 2012/0020537 A1 | 1/2012 | Garcia et al. | |
| 2012/0021410 A1 | 1/2012 | Yin et al. | |
| 2012/0046178 A1 | 2/2012 | Van Den Boom et al. | |
| 2012/0142014 A1 | 6/2012 | Cai | |
| 2012/0301886 A1 | 11/2012 | Farrell et al. | |
| 2013/0109019 A1 | 5/2013 | Murillo et al. | |
| 2014/0031243 A1 | 1/2014 | Cai et al. | |
| 2014/0073520 A1 | 3/2014 | Cai et al. | |
| 2014/0099637 A1 | 4/2014 | Nolan et al. | |
| 2014/0171338 A1 | 6/2014 | Terbrueggen et al. | |
| 2014/0242581 A1 | 8/2014 | Johnson | |
| 2015/0225801 A1 | 8/2015 | Cai et al. | |
| 2016/0019334 A1 | 1/2016 | Cai et al. | |
| 2016/0369329 A1 | 12/2016 | Cai et al. | |
| 2018/0142307 A1 | 5/2018 | Cai et al. | |
| 2021/0017587 A1 | 1/2021 | Cai et al. | |
| 2023/0212658 A1* | 7/2023 | Cai | G01N 21/6458 |
| | | | 506/9 |
| 2023/0295697 A1 | 9/2023 | Cai et al. | |

FOREIGN PATENT DOCUMENTS

| | | | |
|---|---|---|---|
| EP | 2992115 | B1 | 3/2020 |
| JP | H09168399 | A | 6/1997 |
| JP | 2002-542793 | A | 12/2002 |
| JP | 2003-527075 | A | 9/2003 |
| WO | WO 03/027640 | A2 | 4/2003 |
| WO | WO 2003/083440 | A2 | 10/2003 |
| WO | WO 03/102239 | A2 | 12/2003 |
| WO | WO 2007/001986 | A2 | 1/2007 |
| WO | WO 2010/148039 | A2 | 12/2010 |
| WO | WO 2011/038403 | A1 | 3/2011 |
| WO | WO 2011/048184 | A1 | 4/2011 |
| WO | WO 2011/112634 | A2 | 9/2011 |
| WO | WO 2012/158967 | A1 | 11/2012 |
| WO | WO 2013/096851 | A1 | 6/2013 |
| WO | WO 2014/182528 | A2 | 11/2014 |
| WO | WO 2016/018960 | A1 | 2/2016 |

OTHER PUBLICATIONS

Hu et al., An antibody-based microarray assay for small RNA detection. Nucleic Acids Research 24(7) :e52 (Year: 2006).*
Keefe et al., Development of Five Dual-Color, Double-Fusion Fluorescence in Situ Hybridization Assays for the Detection of Common MLL Translocation Partners. J. of Molecular Diagnostics 12(4) :441 (Year: 2010).*
Schubert et al., Analyzing proteome topology and function by automated multidimensional fluorescence microscopy. Nature Biotechnology : doi: 10.1038/nbt1250 (Year: 2006).*
Tkachuk et al., Detection of bcr-abl Fusion in Chronic Myelogeneous Leukemia by in Situ Hybridization. Science 250 : 559 (Year: 1990).*
Summons to Attend Oral Proceedings under Rule 115(1) EPC dated Nov. 17, 2022 for European Patent Application No. 14795452.3, with updated listing of references; 13 pages.
Brief Communication dated Dec. 5, 2022 regarding videoconference for Oral Proceedings for European Patent Application No. 14795452.3; 1 page.
First Office Action dated Nov. 2, 2022 for Chinese Patent Application No. 201910951092.4; with English translation (Machine Translation); 16 pages.
Miner, et al: "Molecular barcodes detect redundancy and contamination in the hairpin-bisulfite PCR", Nucleic Acids Research; published online Sep. 30, 2004; vol. 32, No. 17; e35.
Opponent's Final Submissions for Oral Proceedings for European Patent Application No. 14795452.3 filed Apr. 14, 2023; 39 pages.
Nederlof, et al: "Multiple Fluorescence In Situ Hybridization", Cytometry 1990; vol. 11, pp. 1126-1131.
Office Action dated Feb. 24, 2023 for Korean Patent Application No. 10-2022-7005979; with English translation, 15 pages.
Communication Pursuant to Article 94(3)EPC dated Mar. 28, 2023 forwarding the Examination Report for European Patent Application No. 17837577.0; 5 pages.
Collins, et al: "A Branched DNA signal amplification assay for quantification of nucleic acid targets below 100 molecules/ml", Nucleic Acids Research 1997; vol. 25(15), pp. 2979-2984.
Notification of Reasons for Refusal dispatched May 9, 2023 for Japanese Patent Application No. 2022-074240; with English translation, 13 pages.
Examination Report for Canadian Patent Application No. 3,032,649 dated Nov. 19, 2024; 4 pages.
Apr. 22, 2024 Notification of Appeal Number; Commencement of Proceedings before the Board of Appeal for EP2992115; 7 pages.
Jun. 10, 2024 Internal EPO Communication regarding Withdrawal of Appeal for EP2992115; 4 pages.
Jun. 12, 2024 Withdrawal of Appeal for EP2992115; 4 pages.
Jun. 13, 2024 Closure of Appeal Proceedings EP2992115; 1 page.
Jun. 14, 2024 Communication Pursuant to Rule 82(2) EPC for EP2992115; 4 pages.
Notice of Reasons for Refusal mailed Dec. 15, 2020 for Japanese Patent Application No. 2019-189650, English translation 10 pages.
Communication of a notice of Opposition mailed Dec. 18, 2020 for European Patent No. EP2992115, 148 pages.
Communication of notices of Opposition (R.79(1) EPC) mailed Dec. 21, 2020 for European Patent No. EP2992115, 1 page.
Consolidated list of references for notice of Opposition mailed Dec. 18, 2020 for European Patent No. EP2992115, 2 pages.
Notice of Reasons for Rejection/Notice to File a Response mailed Dec. 29, 2020 for Korean Patent Application No. 10-2015-7033924, with English translation, 9 pages.
Almstrand, et al: "New methods for analysis of spatial distribution and coaggregation of microbial populations in complex biofilms", Applied and Environmental Microbiology; Oct. 2013; vol. 79(19), pp. 5978-5987.
Almstrand, et al: D21 Supplement—additional documents (from Consolidated list of references for notice of Opposition mailed Dec. 18, 2020).
Choi, et al: "Next Generation in Situ Hybridization Chain Reaction: higher gain, lower cost, greater durability", ACS Nano; May 27, 2014; vol. 8(5), pp. 4284-4294.
Daphnis, et al: "Detailed FISH analysis of day 5 human embryos reveals the mechanisms leading to mosaic aneuploidy", Human Reproduction 2005; Nov. 26, 2004; vol. 20(1), pp. 129-137.
Epstein, et al: "Reutilization fo previously hybridized slides for fluorescence in situ hybridization", Cytometry 1995; vol. 21, pp. 378-381.
Kitayama, et al: "Repeated fluorescence in situ hybridization by microwave-enhanced protocol", Pathology International 2006, vol. 56, pp. 490-493.
Kris, et al: "High-throughput, high-sensitivity analysis of gene expression in *Arabidopsis*", Plant Physiology; Jul. 2007; vol. 144, pp. 1256-1266.
Lubeck, et al: "Single-cell in situ RNA profiling by sequential hybridization", Nature Methods 2014; Mar. 28, 2014; vol. 11(4), pp. 360-361. (D2 from Consolidated list of references for notice of Opposition mailed Dec. 18, 2020).
Lubeck, et al: D2a Supplementary Information (from Consolidated list of references for notice of Opposition mailed Dec. 18, 2020); Figures 1-10 Supplementary Methods and Supplementary Note.
Lubeck, et al: D2b Excerpt from Nature Methods WEBSITE proving the publication date Mar. 28, 2014 for D2 and D2a (retrieved on Dec. 4, 2020 at https://www.nature.com/articles/nmeth.2892); 5 pages; (from Consolidated list of references for notice of Opposition mailed Dec. 18, 2020).

(56) References Cited

OTHER PUBLICATIONS

Mali, et al: "Barcoding cells using cell-surface programmable DNA-binding domains", Nature Methods; May 2013; vol. 10, No. 5, pp. 403-406.

Mokros, et al: "Identification of chromosomal fusion sites in Arabidopsis mutants using sequential bicolour BAC-FISH", Genome; Aug. 2006; vol. 49(8), pp. 1036-1042.

Player, et al: "Single-copy gene detection using branched DNA (bDNA) In Situ Hybridization", Journal of Histochemistry & Cytochemistry 2001; vol. 49(5), pp. 603-611.

Uher, et al: "Non-informative results and monosomies in PGD: the importance of a third round of re-hybridization", Reproductive Bio Medicine Online; Aug. 12, 2009; vol. 19(4), pp. 539-546.

VYSIS MultiVysion PGT Multi-color FISH Probe Kit, Abbott Laboratories; Sep. 2014 (D5a from Consolidated list of references for notice of Opposition mailed Dec. 18, 2020).

Wang, et al: "A novel in situ RNA analysis platform for Formalin-fixed, Paraffin-embedded tissues", The Journal of Molecular Diagnostics; Jan. 1, 2012; vol. 14(1); pp. 22-29.

Zhen, et al: "Poly-FISH: A technique of repeated hybridizations that improves cytogenetic analysis of fetal cells in maternal blood", Prenatal Diagnosis 1998; vol. 18, pp. 1181-1185.

Communication under Rule 164 EPC with supplementary partial European Search Report dated Jan. 29, 2020 issued for European Patent Application No. 17837577.0, 11 pages.

Office Action dated Mar. 6, 2020 issued for Canadian Patent Application No. 2,907,493, 7 pages.

Communication forwarding the extended European Search Report dated Feb. 7, 2020 issued for European Patent Application No. 19206244.6, 8 pages.

Choi, Harry M.T., et al., "Programmable in situ amplification for multiplexed imaging of mRNA expression", Nat Biotechnol, vol. 28, No. 11, pp. 1208-1212 (Nov. 2010).

Lubeck, Eric, et al., "Single-cell in situ RNA profiling by sequential hybridization", Nature Methods, vol. 1, No. 4, pp. 360-361 (Apr. 2014).

Lubeck, Eric, et al., "Single-cell systems biology by super-resolution imaging and combinatorial labeling", Nature Methods, vol. 9, No. 7, pp. 743-748 (Jul. 2012).

Muller, Stefan, et al., "A nonredundant multicolor bar code as a screening tool for rearrangements in neoplasia", Genes Chromosomes & Cancer, vol. 39, No. 1, pp. 59-70 (Jan. 2004).

Shah, et al., "In Situ Transcription Profiling of Single Cells Reveals Spatial Organization of Cells in the Mouse Hippocampus", J. Neuron., NeuroResource Oct. 19, 2019, vol. 92, No. 2, pp. 342-357.

Communication forwarding the extended European Search Report dated Jun. 26, 2020 issued for European Patent Application No. 17837577.0, 10 pages.

Goransson, et al. "A single molecule array for digital targeted molecular analyses", Nucleic Acids Research 2009; published online Nov. 25, 2008; vol. 39(1); e-7, pp. 1-9.

Khandjian, EW, "UV crosslinking RNA to nylon membrane enhances hybridization signals", Mol. Biol. Rep. 1986, vol. 11, pp. 107-115.

Eberle, et al: "Power to Detect Risk Alleles Using Genome-Wide Tag SNP Panels", PLOS Genetics; Oct. 2007; vol. 3(10), e170; pp. 1827-1837.

Fan, et al: "Illumina Universal Bead Arrays", Methods in Enzymology 2006; vol. 410, pp. 57-73.

Femino, et al: "Visualization of Single RNA Transcripts in Situ", Science; Apr. 24, 1998; vol. 280, pp. 585-590.

Gundersan, et al: "Decoding randomly ordered DNA arrays", Genome Research 2004; vol. 14, pp. 870-877.

Kivioja, et al: "Counting absolute numbers of molecules using unique molecular identifiers", Nature Methods; Jan. 2012 (published online Nov. 20, 2011); vol. 9(1), pp. 72-74.

Kuhn, et al: "A novel, high-performance random array platform for quantitative gene expression profiling", Genome Research 2004; downloaded Jul. 28, 2021; vol. 14, pp. 2347-2356.

Levsky, et al: "Single-cell gene expression profiling", Science; Aug. 2, 2002; vol. 297, pp. 836-840.

Muller, et al: "Cross-species colour segmenting: A novel tool in Human Karyotype analysis", Cytometry 1998; vol. 33, pp. 445-452.

Muller, et al: "Towards unlimited colors for fluorescence in-situ hybridization (FISH)", Chromosome Research 2002; vol. 10, pp. 223-232.

Shiroguchi, et al: "Digital RNA sequencing minimizes sequence-dependent bias and amplification noise with optimized single-molecule barcodes", PNAS; Jan. 24, 2012; vol. 109(4), pp. 1347-1352.

Weremowicz, et al: "Validation of DNA probes for preimplantation genetic diagnosis (PGD) by fluorescence in situ hybridization (FISH) R1", Prenat. Diag.; Nov. 2006; vol. 26(11), pp. 1042-1050.

First Office Action and Search Report issued Jan. 4, 2022 for Chinese Patent Application No. 201780061639.2, with English translation, 51 pages.

Notice of Reasons for Refusal issued Nov. 2, 2021 for Japanese Patent Application No. 2019-189650, with English translation, 5 pages.

Final Preliminary Rejection dated Aug. 6, 2021 issued for Korean Patent Application No. 10-2015-7033924, with English translation, 7 pages.

Communication Pursuant to 94(3) EPC dated Aug. 2, 2021 issued for European Patent Application No. 19206244.6, 5 pages.

Ahern, H., The Scientist 9(15); 20 (Year 1995).

Giestas, et al., "Multiplexed spectral coding for simultaneous detection of DNA hybridization reactions based on FRET", Sensors and Actuators B: Chemical 134: 136 (Year 2008).

Lassauniere, et al., "A novel multiplex real-time RT-PCR assay with FRET hybridization probes for the detection and quantitation of 13 respiratory viruses", J. of Virological Methods 165: 265-260 (Year 2010).

Examination Report dated Mar. 26, 2021 issued for Canadian Patent Application No. 2,907,493; 5 pages.

Rejection Decision dated Jun. 27, 2024 for Chinese Patent Application No. 201910951092.4; 6 pages with English translation.

Final Office Action mailed Jan. 22, 2024 for U.S. Appl. No. 16/322,462; 35 pages.

EPO Communication Pursuant to 94(3) EPC dated Dec. 20, 2023 forwarding the Examination Report for European Patent Application No. 19206244.6; 6 pages.

Notice of Final Rejection dated Nov. 27, 2023 for Korean Patent Application No. 10-2022-7005979; with English translation, 7 pages.

Decision to Refuse dated Dec. 26, 2023 for Japanese Patent Application No. 2022-074240; with English translation, 13 pages.

EPO Communication dated Feb. 13, 2024 forwarding Interlocutory Decision in Opposition Proceedings for EP2992115; 112 pages.

Office Action for Canadian Patent Application No. 2,907,493 dated May 11, 2023; 5 pages.

U.S. Appl. No. 61/817,651 claimed in PCT/2014/036258, filed Apr. 30, 2013, Cai, et al.

U.S. Appl. No. 61/971,974 claimed in PCT/2014/036258, filed Mar. 28, 2014, Cai, et al.

Examination Report for Canadian Patent Application No. 3,032,649 dated Jul. 21, 2023; 4 pages.

Lee, et al., "Highly multiplexed subcellular RNA sequencing in situ", Science; Mar. 21, 2014; vol. 343(6177); pp. 1360-1363.

Apr. 14, 2023 Submission in Opposition Proceedings for EP2992115: Submission List, 2 pages.

Apr. 14, 2023 Submission in Opposition Proceedings for EP2992115: Letter to EPO Summary of Requests; 7 pages.

Apr. 14, 2023 Submission in Opposition Proceedings for EP2992115: Letter to EPO Attendee List for Oral Proceedings; 2 pages.

Apr. 14, 2023 Submission in Opposition Proceedings for EP2992115: Published Evidence 1; Takei, et al., Nature 2021; 53 pages.

Apr. 14, 2023 Submission in Opposition Proceedings for EP2992115: Published Evidence 2; Eng, et al., Nature 2019; 37 pages.

Apr. 14, 2023 Submission in Opposition Proceedings for EP2992115: Published Evidence 3; Shah, et al., Neuron 2016; 31 pages.

Apr. 14, 2023 Submission in Opposition Proceedings for EP2992115: Published Evidence 4; Shah, et al., Cell 2018; 35 pages.

(56)            References Cited

OTHER PUBLICATIONS

Apr. 14, 2023 Submission in Opposition Proceedings for EP2992115: New First Auxiliary Request 1 through New Twelfth Auxiliary Request (clean and marked); 71 pages.

Apr. 14, 2023 EPO Acknowledgment of Receipt (Submission No. 11947234) for written submissions filed for EP2992115; 2 pages.

Jun. 14, 2023 Opponent additional submission in advance of Oral Proceedings; 23 pages.

Jun. 14, 2023 Opponent additional submission in Opposition Proceedings made following summons to attend Oral Proceedings; 2 pages.

Jun. 14, 2023 EPO Acknowledgment of Receipt (Submission No. 12129203) for written submissions filed by opponent; 1 pages.

Jun. 14, 2023 Letter to EPO; Request For Adjournment of Oral Proceedings; 1 page.

Jun. 22, 2023 Summons to Oral Proceedings canceled (adjournment granted); 1 page.

Jun. 26, 2023 Postponement; Summons to Attend Oral Proceedings pursuant to Rule 115(1) EPC; 6 pages.

Oct. 5, 2023 Submission for Oral Proceedings by Opponent; Letter to EPO; EPO Acknowledgment of Receipt (Submission No. 12497872); Opponent's reply to examination report in opposition proceedings for EP2992115; 5 pages.

Oct. 6, 2023 Submission in Opposition Proceedings for EP2992115: Letter to EPO; EPO Form 1038; 1 page.

Oct. 6, 2023 Submission in Opposition Proceedings for EP2992115: Letter to EPO; EPO Form 1038 Description of Documents filed; 2 pages.

Oct. 6, 2023 Submission in Opposition Proceedings for EP2992115: Letter to EPO; Attendee List for Oral Proceedings; 2 pages.

Oct. 6, 2023 Submission in Opposition Proceedings for EP2992115: Letter to EPO; Summary of Requests; 17 pages.

Oct. 6, 2023 Submission in Opposition Proceedings for EP2992115: D31 Declaration by Michael B. Elowitz, 16 pages.

Oct. 6, 2023 Submission in Opposition Proceedings for EP2992115: D32 Declaration by Arjun Raj, 14 pages.

Oct. 6, 2023 Submission in Opposition Proceedings for EP2992115: D33 Precautions for Handling of RNA.

Oct. 6, 2023 Submission in Opposition Proceedings for EP2992115: Main Request (clean); 3 pages.

Oct. 6, 2023 Submission in Opposition Proceedings for EP2992115: Main Request (marked); 3 pages.

Oct. 6, 2023 Submission in Opposition Proceedings for EP2992115: New Auxiliary Request 1 through New Auxiliary Request 21 (clean and marked); 136 pages.

Oct. 6, 2023 EPO Acknowledgment of Receipt (Submission No. 12505217) for written submissions filed for EP2992115; 1 page.

Oct. 6, 2023 EPO Acknowledgment of Receipt (Submission No. 12505057) for written submissions filed for EP2992115; 3 pages.

Blanco, Ana, et al., "A FRET-based assay for characterization of alternative splicing events using peptide nucleic acid fluorescence in titu hybridization", Nucleic Acids Research, vol. 37, No. 17, e116 (Jun. 26, 2009).

Eng, et al., Profiling the transcriptome with RNA SPOTs Nature Methods Published Online Nov. 13, 2017; doi:10.1038/NMETH. 4500, 6 pages.

Fernandez-Suarez, Marta, et al., "Fluorescent probes for super-resolution imaging in living cells", Molecular Cell Biology, vol. 9, pp. 929-943 (Dec. 2008).

Flagella, et al., A multiplex branched DNA assay for parallel quantitative gene expression profiling, Analytical Biochemistry, Mar. 2006, vol. 352, pp. 50-60.

Ioannou, D., et al., "Multicolour interphase cytogenetics: 24 chromosome probes, 6 colours, 4 layers", Molecular and Cellular Probes, vol. 25, pp. 199-205 (Aug. 2011).

Levesque, Marshall J., et al., "Single-chromosome transcriptional profiling reveals chromosomal gene expression regulation", Nature Methods, vol. 10, No. 3, pp. 246-248 (Mar. 2013).

Levesque, Marshall J., et al., "Visualizing SNVs to quantify allele-specific expression in single cells", Nature Methods, vol. 10, No. 9, pp. 865-867 (Sep. 2013).

Liehr, T., et al., "Multicolor FISH probe sets and their applications", Histology and Histopathology, vol. 19, pp. 229-237 (Year: 2004).

Linton, et al., Microarray Gene Expression Analysis of Fixed Archival Tissue Permits Molecular Classification and Identification of Potential Therapeutic Targets in Diffuse Large B-Cell Lymphoma, Journal Of Molecular Diagnostics, May 2012, vol. 14, No. 3, pp. 223-232.

Lu, Jing, et al., "Quantification of mIRNA Abundance in single cells using locked nucleic acid-FISH and enzyme-labeled fluorescence", Methods in Molecular Biology 680:77 (Year: 2011).

Moffitt, Jeffrey R., et al., "High-throughput single-cell gene-expression profiling with multiplexed error-robust fluorescence in situ hybridization", PNAS Sep. 27, 2016, vol. 113, No. 39, p. 11046 - 11051.

Pon, et al., Tandem oligonucleotide synthesis using linker phosphoramidites, Nucleic Acids Research, Apr. 6, 2005, vol. 33, No. 6, pp. 1940-1948.

Shah, et al., Dynamics and Spatial Genomics of the Nascent Transcriptome by Intron seqFISH Cell (2018) doi.org/10.1016/j.cell.2018.05.035, 15 pages.

Sinclair, et al., Improved Sensitivity of Bcr-A Bl Detection: A Triple Probe Three-Color Fluorescence In Situ Hybridization System, *Blood*, Aug. 15, 1997, vol. 90, No. 4, pp. 1395-1402.

Theodosiou, Zenonas, et al., "Automated analysis of FISH and immunohistochemistry images: a review", Cytometry Part A, vol. 71A, pp. 439-450 (Year: 2007).

Urdea, et al., A comparison of non-radioisotopic hybridization assay methods using fluorescent, chemilluminescent and enzyme labeled synthetic oligodeoxyribonucleotide probes, *Nucleic Acids Research* 1988, vol. 16, No. 11, pp. 4937-4956.

Velculescu, et al., "Analysis of human transcriptomes", Nature Dec. 1999, vol. 23, pp. 387-388.

Bagasra, "Protocols for the in situ PCR-amplification and detection of mRNA and DNA sequences", Nature Protocols; published online Nov. 1, 2007; vol. 2 (11); pp. 2782.

\* cited by examiner

Fig. 2 a

FISH probes with purple dye

DNase I mRNA mRNA
Hyb 1

Rehyb

Same probes with blue dye mRNA mRNA
Hyb 2

DNase I and rehyb

N hybs

Barcode # scales as $F^N$

Same probes with green dye mRNA
Hyb N b

Composite four-color FISH images

Hybridization 1 – probe set 1

5 μm

Hybridization 2 – probe set 2

5 μm

Hybridization 3 – probe set 1

MULTIPLEX LABELING OF MOLECULES BY SEQUENTIAL HYBRIDIZATION BARCODING

CROSS-REFERENCE TO RELATED APPLICATIONS

This application is a continuation of U.S. patent application Ser. No. 16/572,511, filed on Sep. 16, 2019, which is a continuation of U.S. patent application Ser. No. 14/435,735, filed on Apr. 14, 2015, and entitled "Multiplex Labeling of Molecules by Sequential Hybridization Barcoding," which is a National Stage entry of International Application No. PCT/US2014/36258, and entitled "Multiplex Labeling of Molecules by Sequential Hybridization Barcoding," which in turn claims priority to U.S. Provisional Application No. 61/817,651, filed on Apr. 30, 2013, and entitled "Multiplex Labeling of Molecules in Single Cells by Sequential Hybridization Barcoding," and U.S. Provisional Application No. 61/971,974, filed on Mar. 28, 2014, and entitled "Multiplex Labeling of Molecules in Single Cells by Sequential Hybridization Barcoding," each of which is hereby incorporated by reference herein in its entirety.

STATEMENT REGARDING FEDERALLY SPONSORED RESEARCH OR DEVELOPMENT

This invention was made with government support under Grant No. OD008530 and HD075605 awarded by the National Institutes of Health. The government has certain rights in the invention.

BACKGROUND OF THE INVENTION

Transcription profiling of cells are essential for many purposes. Microscopy imaging which can resolve multiple mRNAs in single cells can provide valuable information regarding transcript abundance and localization, which are important for understanding the molecular basis of cell identify and developing treatment for diseases. Therefore, there is a need for new and improved methods for profile transcripts in cells by, for example, microscopy imaging.

SUMMARY OF THE INVENTION

The present invention provides certain insights into challenges or defects associated with existing technologies for profiling transcripts or DNA loci in cells, particularly for single cells. Moreover, the present invention provides new technologies for achieving effective such profiling, including of single cells. Provided technologies are broadly useful, including for example for profiling of isolated cells, cells in tissues, cells in organs, and/or cells in organisms.

For example, the present invention provides the insight that existing technologies such as single cell RNA-seq or qPCR require single cells to be isolated and put into multi-well format, which is a multiple step process that can be cost prohibitive, labor intensive and prone to artifacts. Furthermore, the present invention recognizes that existing in situ sequencing technologies that use enzymatic reactions to convert the mRNA into a DNA template first can be highly inefficient (for example in the mRNA to DNA conversion process), so that, often, only a small fraction of the RNAs are converted and detected. The present invention provides the particular insight that one major downside of such low efficiency, which is estimated at 1% for RT and 10% for PLA, is that it can introduce significant noise ad bias in the gene expression measurements. The present invention further recognizes that existing spectral mRNA barcoding technologies that utilize single molecule fluorescence in situ hybridization (smFISH) require distinct fluorophores for scale up, and may be limited in the number of barcodes that can be generated. smFISH also requires splitting probes into barcoding subsets during hybridization. Because smFISH often uses two or more colors for a target, it produces high density of objects in the image, which can increase the complexity of data analysis.

Among other things, the present inventions provides new technologies for profiling, for example, transcripts and/or DNA loci, that overcome one or more or all of the problems associated with methods prior to the present invention. In some embodiments, the present invention provides methods for detecting multiple targets, e.g., transcripts or DNA loci, in a cell through a sequential barcoding scheme that permits multiplexing of different targets.

In some embodiments, the present invention provides methods, comprising steps of:

(a) performing a first contacting step that involves contacting a cell comprising a plurality of nucleic acids with a first plurality of detectably labeled oligonucleotides, each of which targets a nucleic acid and is labeled with a detectable moiety, so that the composition comprises at least:

(i) a first oligonucleotide targeting a first nucleic acid and labeled with a first detectable moiety; and (ii) a second oligonucleotide targeting a second nucleic acid and labeled with a second detectable moiety;

(b) imaging the cell after the first contacting step so that interaction by oligonucleotides of the first plurality with their targets is detected;

(c) performing a second contacting step that involves contacting the cell with a second plurality of detectably labeled oligonucleotides, which second plurality includes oligonucleotides targeting overlapping nucleic acids that are targeted by the first plurality, so that the second plurality comprises at least:

(i) a third oligonucleotide, optionally identical in sequence to the first oligonucleotide, targeting the first nucleic acid; and (ii) a fourth oligonucleotide, optionally identical in sequence to the second oligonucleotide, targeting the second nucleic acid, wherein the second plurality differs from the first plurality in that at least one of the oligonucleotides present in the second plurality is labeled with a different detectable moiety than the corresponding oligonucleotide targeting the same nucleic acid in the first plurality, so that, in the second plurality:

(iii) the third oligonucleotide is labeled with the first detectable moiety, the second detectable moiety or a third detectable moiety; and (iv) the fourth oligonucleotide is labeled with the first detectable moiety, the second detectable moiety, the third detectable moiety, or a fourth detectable moiety, wherein either the third oligonucleotide is labeled with a different detectable moiety than was the first oligonucleotide, or the fourth oligonucleotide is labeled with a different detectable moiety than was the second oligonucleotide, or both;

(d) imaging the cell after the second contacting step so that interaction by oligonucleotides of the second plurality with their targets is detected; and (e) optionally repeating the contacting and imaging steps, each time with a new plurality of detectably labeled oligonucleotides comprising oligonucleotides that target overlapping nucleic acids targeted by the first and second pluralities, wherein each utilized plurality differs from each other utilized plurality, due to at least one difference in detectable moiety labeling of oligonucleotides targeting the same nucleic acid.

In some embodiments, the present invention (e.g., as represented in FIG. 1), provides methods comprising steps of:

(a) performing a first contacting step that involves contacting a cell comprising a plurality of transcripts and DNA loci with a first plurality of detectably labeled oligonucleotides, each of which targets a transcript or DNA locus and is labeled with a detectable moiety, so that the composition comprises at least:

(i) a first oligonucleotide targeting a first transcript or DNA locus and labeled with a first detectable moiety; and (ii) a second oligonucleotide targeting a second transcript or DNA locus and labeled with a second detectable moiety;

(b) imaging the cell after the first contacting step so that recognition by oligonucleotides of the first plurality with their targets is detected;

(c) performing a second contacting step that involves contacting the cell with a second plurality of detectably labeled oligonucleotides, which second plurality includes oligonucleotides targeting overlapping transcripts and/or DNA loci that are targeted by the first plurality, so that the second plurality comprises at least:

(i) a third oligonucleotide, optionally identical in sequence to the first oligonucleotide, targeting the first transcript or DNA locus; and (ii) a fourth oligonucleotide, optionally identical in sequence to the second oligonucleotide, targeting the second transcript or DNA locus, wherein the second plurality differs from the first plurality in that at least one of the oligonucleotides present in the second plurality is labeled with a different detectable moiety than the corresponding oligonucleotide targeting the same transcript or DNA locus in the first plurality, so that, in the second plurality:

(iii) the third oligonucleotide is labeled with the first detectable moiety, the second detectable moiety or a third detectable moiety; and (iv) the fourth oligonucleotide is labeled with the first detectable moiety, the second detectable moiety, the third detectable moiety, or a fourth detectable moiety, wherein either the third oligonucleotide is labeled with a different detectable moiety than was the first oligonucleotide, or the fourth oligonucleotide is labeled with a different detectable moiety than was the second oligonucleotide, or both;

(d) imaging the cell after the second contacting step so that recognition by oligonucleotides of the second plurality with their targets is detected; and (e) optionally repeating the contacting and imaging steps, each time with a new plurality of detectably labeled oligonucleotides comprising oligonucleotides that target overlapping transcripts or DNA loci targeted by the first and second pluralities, wherein each utilized plurality differs from each other utilized plurality, due to at least one difference in detectable moiety labeling of oligonucleotides targeting the same transcript or DNA locus.

In some embodiments, a nucleic acid targeted by a detectably labeled oligonucleotide is or comprises a transcript and/or DNA locus. In some embodiments, a nucleic acid targeted by a detectably labeled oligonucleotide is or comprises a transcript. In some embodiments, a nucleic acid targeted by a detectably labeled oligonucleotide is a transcript. In some embodiments, a nucleic acid targeted by a detectably labeled oligonucleotide is or comprises a DNA locus. In some embodiments, a nucleic acid targeted by a detectably labeled oligonucleotide is a DNA locus. In some embodiments, each plurality of detectably labelled oligonucleotides used in a contacting step targets the same transcripts and/or DNA locus.

In some embodiments, a plurality of detectably labeled oligonucleotides utilized in a contacting step is referred to as a set of detectably labeled oligonucleotides. In some embodiments, targets of a set of detectably labeled oligonucleotides are referred to as a set of targets. In some embodiments, a target in a set is or comprises a transcript. In some embodiments, a target in a set is a transcript. In some embodiments, each target in a set is or comprises a transcript. In some embodiments, each target in a set is transcript. In some embodiments, a target in a set is or comprises a DNA locus. In some embodiments, a target in a set is a DNA locus. In some embodiments, each target in a set is or comprises a DNA locus. In some embodiments, each target in a set is DNA locus.

In some embodiments, provided methods optionally comprise a step of removing a plurality of detectably labeled oligonucleotides after an imaging step. In some embodiments, provided methods comprises a step of removing a plurality of detectably labeled oligonucleotides after each imaging step. In some embodiments, the step of removing comprises contacting a plurality of detectably labeled oligonucleotides with an enzyme that digests a detectably labeled oligonucleotide. In some embodiments, the step of removing comprises contacting the plurality of detectably labeled oligonucleotides with a DNase. In some embodiments, a step of removing comprises contacting a plurality of detectably labeled oligonucleotides with an RNase. In some embodiments, a step of removing comprises photobleaching.

In some embodiments, each set comprises two or more detectably labeled oligonucleotides targeting the same transcript and/or DNA locus. In some embodiments, two or more detectably labeled oligonucleotides in a set targeting the same transcript and/or DNA locus produce the same detectable signal. In some embodiments, all detectably labeled oligonucleotides in a set targeting the same transcript and/or DNA locus produce the same detectable signal. In some embodiments, wherein the detectably labeled oligonucleotides are labeled with fluorophore, a detectable signal is a certain color. In some embodiments, all detectably labeled oligonucleotides in a set targeting the same transcript and/or DNA locus are labelled with fluorophores providing the same detectable color.

In some embodiments, two or more detectably labeled oligonucleotides in a set targeting the same transcript and/or DNA locus have the same detectable label. In some embodiments, all detectably labeled oligonucleotides in a set targeting the same transcript and/or DNA locus have the same detectable label. In some embodiments, all detectably labeled oligonucleotides targeting the same transcript and/or DNA locus have the same fluorophore.

In some embodiments, the present invention provides compositions useful for conducting provided methods.

In some embodiments, the present invention provides compositions comprising a plurality of detectably labeled oligonucleotides, each of which targets a nucleic acid and is labeled with a detectable moiety, so that the composition comprises at least:

(i) a first oligonucleotide targeting a first nucleic acid and labeled with a first detectable moiety; and (ii) a second oligonucleotide targeting a second nucleic acid and labeled with a second detectable moiety.

In some embodiments, the present invention provides a kit comprising a plurality of detectably labeled oligonucleotides, each of which targets a nucleic acid and is labeled with a detectable moiety, so that the kit comprises at least:

(i) a first oligonucleotide targeting a first nucleic acid and labeled with a first detectable moiety;

(ii) a second oligonucleotide targeting a second nucleic acid and labeled with a second detectable moiety.

(iii) a third oligonucleotide, optionally identical in sequence to the first oligonucleotide, targeting the first nucleic acid and labeled with the first, the second or a third detectable moiety; and (iv) a fourth oligonucleotide, optionally identical in sequence to the second oligonucleotide, targeting the nucleic acid, and labeled with the first, the second, the third or a fourth detectable moiety, wherein either the third oligonucleotide is labeled with a different detectable moiety than the first oligonucleotide, or the fourth oligonucleotide is labeled with a different detectable moiety than the second oligonucleotide, or both.

In some embodiments, a detectable moiety is or comprises a fluorophore.

In some embodiments, a plurality of detectably labeled oligonucleotides target two or more nucleic acids ("targets"). In some embodiments, a target is or comprises a transcript. In some embodiments, a target is a transcript. In some embodiments, a target is an RNA. In some embodiments, a target is mRNA. In some embodiments, a target is tRNA. In some embodiments, a target is rRNA. In some embodiments, a target is a non-coding RNA. In some embodiments, a target is or comprises a DNA locus. In some embodiments, a transcript is a DNA locus. In some embodiments, a target is a locus of a transcript. In some embodiments, different transcripts of a DNA sequence, such as splicing variants of a gene, constitutes different targets, wherein one or more of the variant can be independently targeted and detected or quantified. In some embodiments, the present invention provides methods, compositions or kits to detect individual splicing variants. In some embodiments, the present invention provides methods, compositions, or kits for detecting single nucleotide polymorphisms (SNPs).

In some embodiments, provided methods quantify a target, e.g., a transcript or a DNA locus.

In some embodiments, oligonucleotides targeting the same target have the same set of sequences, i.e., when applied at different steps, the differences among the oligonucleotides are within the moieties, not the sequences.

Definitions

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, word length=12 to obtain nucleotide sequences homologous to nucleic acid molecules of the invention. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Oligonucleotide: the term "oligonucleotide" refers to a polymer or oligomer of nucleotide monomers, containing any combination of nucleobases, modified nucleobases, sugars, modified sugars, phosphate bridges, or modified bridges.

Oligonucleotides of the present invention can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Predetermined: By predetermined is meant deliberately selected, for example as opposed to randomly occurring or achieved. A composition that may contain certain individual oligonucleotides because they happen to have been generated through a process that cannot be controlled to intentionally generate the particular oligonucleotides is not a "predetermined" composition. In some embodiments, a predetermined composition is one that can be intentionally reproduced (e.g., through repetition of a controlled process).

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Subject: As used herein, the term "subject" or "test subject" refers to any organism to which a provided compound or composition is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

BRIEF DESCRIPTION OF THE DRAWINGS

FIG. 12. Re-Hybridization of Nanog mRNA in Mouse Embryonic Stem Cells (mESCs). Re-Hybridization of Nanog mRNA in Mouse Embryonic Stem Cells (mESCs). Probes were stripped off by 30 minutes of DNase I incubation at a concentration of 3 Units/µL. Nanog Alexa 647 probes were re-hybridized for 12 hours and imaged. Images were 2D maximum projections created from z stacks of 11 images taken every 1.5 µm.

FIG. 21. Hybridization Chain Reaction (HCR) Re-hybridization Using Exonuclease III (ExoIII). (a) Schematic representation of exoIII digestion of bridging strands and HCR polymers. ExoIII digests bridging strands and HCR polymers from the 3' to 5' direction into dNMP's leaving behind intermediate probe strands bound to targets, e.g., mRNAs. A new bridging strand can then by hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

DETAILED DESCRIPTION OF CERTAIN EMBODIMENTS

Among other things, the present invention provides new methods, compositions and/or kits for profiling nucleic acids (e.g., transcripts and/or DNA loci) in cells.

In some embodiments, the present invention provides methods for profiling nucleic acids (e.g., transcripts and/or DNA loci) in cells. In some embodiments, provide methods profile multiple targets in single cells. Provided methods can, among other things, profile a large number of targets (transcripts, DNA loci or combinations thereof), with a limited number of detectable labels through sequential barcoding.

Figure 1:
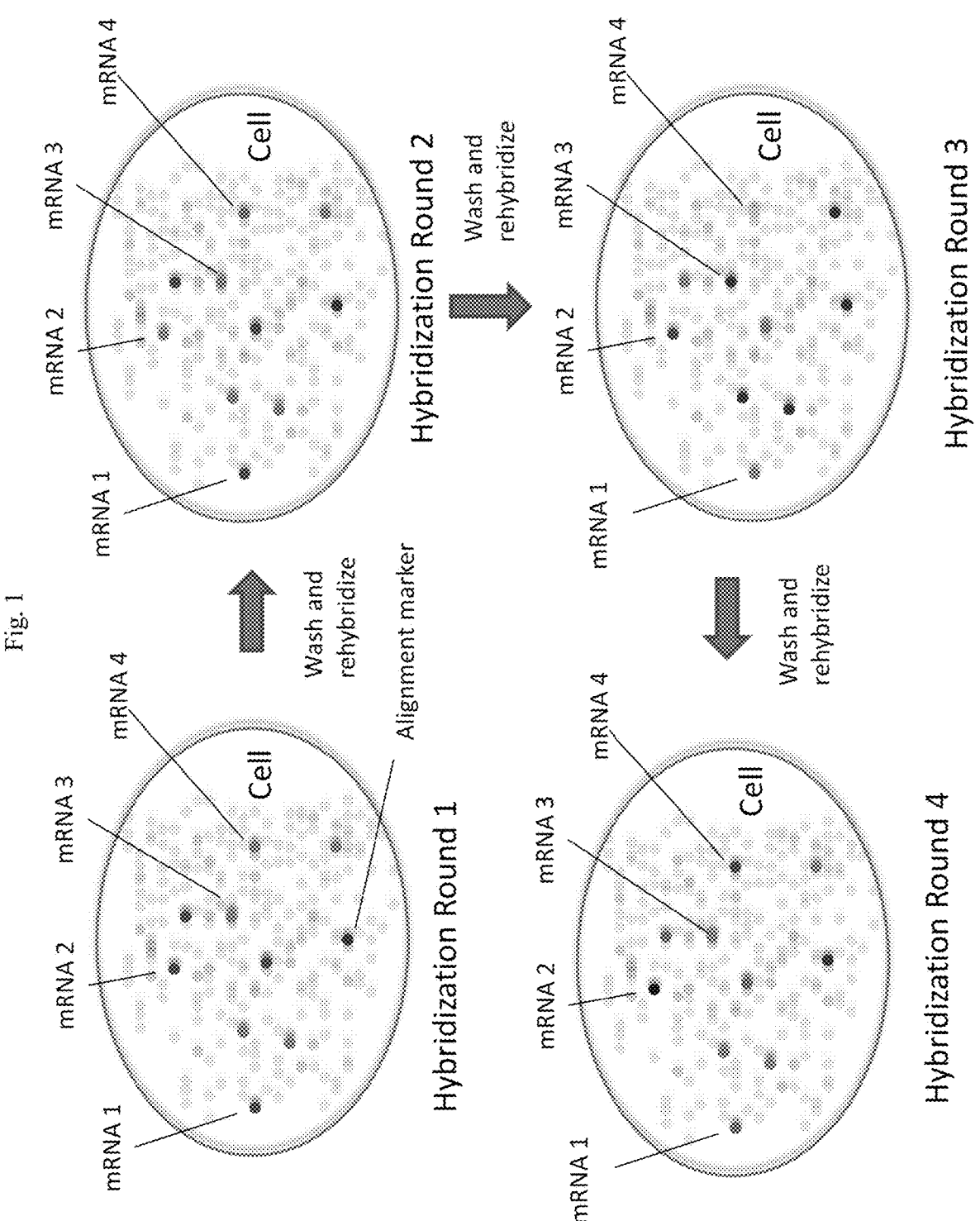
FIG. 1. Methodologies provided by the present disclosure are represented in FIG. 1.

FIG. 1 depicts methodologies in accordance with the present invention. As depicted, the present invention provides methodologies in which multiple rounds of hybridization (contacting steps) with labeled probes profiles nucleic acids (e.g., mRNAs) present in cells. Specifically, as depicted in FIG. 1, sets of probes that hybridize with nucleic acid targets in cells are provided, wherein probes (i.e., detectably labeled oligonucleotides that hybridize with different targets) are labeled within a single set and, furthermore, at least one probe is differently labeled in different sets.

In some embodiments, the present invention (e.g., as represented in FIG. 1), provides methods comprising steps of:

(a) performing a first contacting step that involves contacting a cell comprising a plurality of transcripts and DNA loci with a first plurality of detectably labeled oligonucleotides, each of which targets a transcript or DNA locus and is labeled with a detectable moiety, so that the composition comprises at least:

(i) a first oligonucleotide targeting a first transcript or DNA locus and labeled with a first detectable moiety; and (ii) a second oligonucleotide targeting a second transcript or DNA locus and labeled with a second detectable moiety;

(b) imaging the cell after the first contacting step so that hybridization by oligonucleotides of the first plurality with their targets is detected;

(c) performing a second contacting step that involves contacting the cell with a second plurality of detectably labeled oligonucleotides, which second plurality includes oligonucleotides targeting overlapping transcripts and/or DNA loci that are targeted by the first plurality, so that the second plurality comprises at least:

(i) a third oligonucleotide, optionally identical in sequence to the first oligonucleotide, targeting the first transcript or DNA locus; and (ii) a fourth oligonucleotide, optionally identical in sequence to the second oligonucleotide, targeting the second transcript or DNA locus, wherein the second plurality differs from the first plurality in that at least one of the oligonucleotides present in the second plurality is labeled with a different detectable moiety than the corresponding oligonucleotide targeting the same transcript or DNA locus in the first plurality, so that, in the second plurality:

(iii) the third oligonucleotide is labeled with the first detectable moiety, the second detectable moiety or a third detectable moiety; and (iv) the fourth oligonucleotide is labeled with the first detectable moiety, the second detectable moiety, the third detectable moiety, or a fourth detectable moiety, wherein either the third oligonucleotide is labeled with a different detectable moiety than was the first oligonucleotide, or the fourth oligonucleotide is labeled with a different detectable moiety than was the second oligonucleotide, or both;

(d) imaging the cell after the second contacting step so that hybridization by oligonucleotides of the second plurality with their targets is detected; and (e) optionally repeating the contacting and imaging steps, each time with a new plurality of detectably labeled oligonucleotides comprising oligonucleotides that target overlapping transcripts or DNA loci targeted by the first and second pluralities, wherein each utilized plurality differs from each other utilized plurality, due to at least one difference in detectable moiety labeling of oligonucleotides targeting the same transcript or DNA locus.

As used herein, a detectably labeled oligonucleotide is labeled with a detectable moiety. In some embodiments, a detectably labeled oligonucleotide comprises one detectable moiety. In some embodiments, a detectably labeled oligonucleotide comprises two or more detectable moieties. In some embodiments, a detectably labeled oligonucleotide has one detectable moiety. In some embodiments, a detectably labeled oligonucleotide has two or more detectable moiety.

In some embodiments, a detectable moiety is or comprises a fluorophore. Exemplary detectably labeled oligonucleotides labeled with fluorophores includes but are not limited to probes for fluorescence in situ hybridization (FISH). Widely known and practiced by persons having ordinary skill in the art, FISH is used to, among other things, to detect and localize the presence or absence of specific DNA sequences or RNA targets. Methods for designing and preparing detectably labeled oligonucleotides labeled are widely known in the art, including but not limited to those described in US patent application publication US 20120142014. Due to limitations such as fluorophore availability, FISH, however, can only be used to profile a limited number of targets in a given experiment. Through sequential barcoding to multiplex different targets, provided methods of the present invention can profile a large number of targets, up to $F^N$, wherein F is the number of types of detectable moieties (in the case of FISH, fluorophores) and N is the number of contacting steps (in the case of FISH, hybridization). For example, when F is four and N is 8, almost the entire transcriptome ($4^8=65,536$) can be profiled. In some embodiments, F is at least 2. In some embodiments, F is 3. In some embodiments, F is 4. In some embodiments, F is 5. In some embodiments, F is 6. In some embodiments, F is 7. In some embodiments, F is 8. In some embodiments, F is 9. In some embodiments, F is 10. In some embodiments, F is 11. In some embodiments, F is 12. In some embodiments, F is 13. In some embodiments, F is 14. In some embodiments, F is 15. In some embodiments, F is greater than 15. In some embodiments, N is 2. In some embodiments, N is greater than 2. In some embodiments, N is 3. In some embodiments, N is greater than 3. In some embodiments, N is 4. In some embodiments, N is greater than 4. In some embodiments, N is 5. In some embodiments, N is greater than 5. In some embodiments, N is 6. In some embodiments, N is greater than 6. In some embodiments, N is 7. In some embodiments, N is greater than 7. In some embodiments, N is 8. In some embodiments, N is greater than 8. In some embodiments, N is 9. In some embodiments, Nis greater than 9. In some embodiments, N is 10. In some embodiments, N is greater than 10. In some embodiments, a plurality of detectably labeled oligonucleotides target at least 100 targets.

In a contacting step, a detectably labeled oligonucleotide can be labeled prior to, concurrent with or subsequent to its binding to its target. In some embodiments, a detectably labeled oligonucleotide, such as a fluorophore-labeled oligonucleotide, is labeled prior to its binding to its target. In some embodiments, a detectably labeled oligonucleotide is labeled concurrent with its binding to its target. In some embodiments, a detectably labeled oligonucleotide is labeled subsequent to its binding to its target. In some embodiments, a detectably labeled oligonucleotide is labeled subsequent to hybridization through orthogonal amplification with hybridization chain reactions (HCR) (Choi, H M., *Nat Biotechnol.* 2010 November; 28(11):1208-12). In some embodiments, a detectably labeled oligonucleotide comprises a moiety, e.g., a nucleic acid sequence, that one or more moieties that can provide signals in an imaging step can be directly or indirectly linked to the oligonucleotide.

In some embodiments, the same type of labels can be attached to different probes for different targets. In some embodiments, probes for the same target have the same label in a plurality of detectably labeled oligonucleotides used in a contacting step (a set of detectably labeled oligonucleotides). Each target, after rounds of contacting and imaging, has its own unique combination of labels (sequential barcoding), so that information, e.g., quantitative and/or spatial information, can be obtained for a target. For example, when fluorophores are used to label detectably labeled oligonucleotides, after N steps, a target would have a sequential barcode of $F_1F_2 \ldots F_N$, wherein $F_n$ is the color of fluorophore used for the target in the n-th imaging. One target can be differentiated from another by a difference in their barcodes (e.g., RedRedBlueRed compared to RedRedRed-Blue).

In some embodiments, labels of the present invention is or comprise one or more fluorescent dyes, including but not limited to fluorescein, rhodamine, Alexa Fluors, DyLight fluors, ATTO Dyes, or any analogs or derivatives thereof.

In some embodiments, labels of the present invention include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some embodiments, labels of the present invention include but are not limited to ATTO dyes; Acridine dyes (e.g., Acridine orange, Acridine yellow); Alexa Fluor; 7-Amino actinomycin D; 8-Anilinonaphthalene-1-sulfonate; Auramine-rhodamine stain; Benzanthrone; 5,12-Bis(phenylethynyl)naphthacene; 9,10-Bis(phenyl ethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl) anthracene; 2-Chloro-9,10-diphenylanthracene; Coumarin;

Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), Texas Red, TSQ, Umbelliferone, or Yellow fluorescent protein.

In some embodiments, labels of the present invention include but are not limited to Alexa Fluor family of fluorescent dyes (Molecular Probes, Oregon). Alexa Fluor dyes are widely used as cell and tissue labels in fluorescence microscopy and cell biology. The excitation and emission spectra of the Alexa Fluor series cover the visible spectrum and extend into the infrared. The individual members of the family are numbered according roughly to their excitation maxima (in nm). Certain Alexa Fluor dyes are synthesized through sulfonation of coumarin, rhodamine, xanthene (such as fluorescein), and cyanine dyes. In some embodiments, sulfonation makes Alexa Fluor dyes negatively charged and hydrophilic. In some embodiments, Alexa Fluor dyes are more stable, brighter, and less pH-sensitive than common dyes (e.g. fluorescein, rhodamine) of comparable excitation and emission, and to some extent the newer cyanine series. Exemplary Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some embodiments, labels of the present invention comprise one or more of the DyLight Fluor family of fluorescent dyes (Dyomics and Thermo Fisher Scientific). Exemplary DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some embodiments, a detectable moiety is or comprises a nanomaterial. In some embodiments, a detectable moiety is or compresses a nanoparticle. In some embodiments, a detectable moiety is or comprises a quantum dot. In some embodiments, a detectable moiety is a quantum dot. In some embodiments, a detectable moiety comprises a quantum dot. In some embodiments, a detectable moiety is or comprises a gold nanoparticle. In some embodiments, a detectable moiety is a gold nanoparticle. In some embodiments, a detectable moiety comprises a gold nanoparticle.

One of skill in the art understands that, in some embodiments, selection of label for a particular probe in a particular cycle may be determined based on a variety of factors, including, for example, size, types of signals generated, manners attached to or incorporated into a probe, properties of the cellular constituents including their locations within the cell, properties of the cells, types of interactions being analyzed, and etc.

For example, in some embodiments, probes are labeled with either Cy3 or Cy5 that has been synthesized to carry an N-hydroxysuccinimidyl ester (NHS-ester) reactive group. Since NETS-esters react readily with aliphatic amine groups, nucleotides can be modified with aminoalkyl groups. This can be done through incorporating aminoalkyl-modified nucleotides during synthesis reactions. In some embodiments, a label is used in every 60 bases to avoid quenching effects.

A detectably labeled oligonucleotide can hybridize with a target, e.g., a transcript or DNA locus. In some embodiments, a target is or comprises a transcript. In some embodiments, a target is a transcript. In some embodiments, a transcript is an RNA. In some embodiments, a transcript is an mRNA. In some embodiments, a transcript is tRNA. In some embodiments, a transcript is rRNA. In some embodiments, a transcript is snRNA. In some embodiments, an RNA is a non-coding RNA. Exemplary non-coding RNA types are widely known in the art, including but not limited to long non-coding RNA (lncRNA), microRNA (miRNA), short interfering RNA (siRNA), piwi-interacting RNA (piRNA), small nucleolar RNA (snoRNA) and other short RNAs. In some embodiments, an RNA is lncRNA. In some embodiments, an RNA is miRNA. In some embodiments, an RNA is piRNA. In some embodiments, an RNA is snoRNA.

In some embodiments, a target is or comprises a DNA locus. In some embodiments, when a target is a DNA locus, a detectably labeled oligonucleotide optionally comprises one or more RNA nucleotide or RNA segments. A detectably labeled oligonucleotide comprises RNA sequences can be selectively removed, for example, through RNA-specific enzymatic digestion, after imaging without degrading the DNA target. Exemplary enzymes that specifically degrade RNA but not DNA include but are not limited to various RNase, such as RNase A and RNase H.

In some embodiments, a detectably labeled oligonucleotide directly hybridizes to its target, e.g., a transcript or DNA locus. In some embodiments, a detectably labeled oligonucleotide specifically interacts with (recognizes) its target through binding or hybridization to one or more intermediate, e.g., an oligonucleotide, that is bound, hybridized, or otherwise specifically linked to the target. In some embodiments, an intermediate oligonucleotide is hybridized against its target with an overhang such that a second oligonucleotide with complementary sequence ("bridge oligonucleotide" or "bridge probe") can bind to it. In some embodiments, an intermediate targets a nucleic acid and is optionally labeled with a detectable moiety, and comprises an overhang sequence after hybridization with the target. In some embodiments, an intermediate comprises a sequence that hybridizes to a target, an overhang sequence, and optionally a detectable moiety. In some embodiments, an intermediate comprises a sequence that hybridizes to a target and an overhang sequence. In some embodiments, an intermediate does not have a detectable moiety. In some embodiments, a second oligonucleotide is a detectably labeled oligonucleotide. In some embodiments, a second detectably labeled oligonucleotide is labeled with a dye. In some embodiments, a detectably labeled oligonucleotide is labeled with an HCR polymer. In some embodiments, intermediate oligonucleotides bound to targets are preserved through multiple contacting, removing and/or imaging steps; sequential barcodes are provided through combinations of detectable labels that are linked to intermediate oligonucleotides through bridge probes in the contacting and imaging steps. For example, when detectably labeled oligonucleotides are used as bridge probes, barcodes are provided by detectably labeled oligonucleotides that hybridize with intermediate oligonucleotides through their overhang sequences. After an imaging step, bridge oligonucleotides are optionally removed as described herein. In some embodiments, one intermediate oligonucleotide is employed for a target. In some embodiments, two or more intermediate oligonucleotides are employed for a target. In some embodiments, three or more intermediate oligonucleotides are employed for a target. In some embodiments, four or more intermediate oligonucleotides are employed for a target. In some embodiments, five or more intermediate oligonucleotides are employed for a target. In some embodiments, six or more intermediate oligonucleotides are employed for a target. In some embodiments, seven or more intermediate oligonucleotides are employed for a target. In some embodiments, eight or more intermediate oligonucleotides are employed for a target. In some embodiments, nine or more intermediate oligonucleotides are employed for a target. In some embodiments, 10 or more intermediate oligonucleotides are employed for a target. In some embodiments, 11 or more intermediate oligonucleotides are employed for a target. In some embodiments, 12 or more intermediate oligonucleotides are employed for a target. In some embodiments, 13 or more intermediate oligonucleotides are employed for a target. In some embodiments, 13 or more intermediate oligonucleotides are employed for a target. In some embodiments, 15 or more intermediate oligonucleotides are employed for a target. In some embodiments, 16 or more intermediate oligonucleotides are employed for a target. In some embodiments, 17 or more intermediate oligonucleotides are employed for a target. In some embodiments, 18 or more intermediate oligonucleotides are employed for a target. In some embodiments, 19 or more intermediate oligonucleotides are employed for a target. In some embodiments, 20 or more intermediate oligonucleotides are employed for a target. In some embodiments, 21 or more intermediate oligonucleotides are employed for a target. In some embodiments, 22 or more intermediate oligonucleotides are employed for a target. In some embodiments, 23 or more intermediate oligonucleotides are employed for a target. In some embodiments, 24 or more intermediate oligonucleotides are employed for a target. In some embodiments, 25 or more intermediate oligonucleotides are employed for a target. In some embodiments, 30 or more intermediate oligonucleotides are employed for a target. In some embodiments, 40 or more intermediate oligonucleotides are employed for a target. In some embodiments, 50 or more intermediate oligonucleotides are employed for a target.

In some embodiments, each intermediate oligonucleotide hybridizes with a different sequence of a target. In some embodiments, each intermediate oligonucleotide of a target comprises the same overhang sequence. In some embodiments, each detectably labeled oligonucleotide for a target comprises the same sequence complimentary to the same overhang sequence shared by all intermediate oligonucleotides of the target. In some embodiments, an intermediate oligonucleotide comprises a sequence complimentary to a target, and a sequence complimentary to a detectably labeled oligonucleotide.

In some embodiments, provided methods further comprises steps of:
(f) performing a contacting step that involves contacting a cell comprising a plurality of nucleic acids with a plurality of intermediate oligonucleotides, each of which:

(i) targets a nucleic acid and is optionally labeled with a detectable moiety; and (ii) comprises an overhang sequence after hybridization with the target; and (g) optionally imaging the cell so that interaction between the intermediate oligonucleotides with their targets is detected.

In some embodiments, step (f) and optionally step (g) are performed before step (a). In some embodiments, step (f) is performed step (a). In some embodiments, a removing step preserves intermediate oligonucleotides.

In some embodiments, provided technologies are used to profile different transcripts formed as a result of splicing variation, RNA editing, oligonucleotide modification, or a combination thereof. In some embodiments, a target is an RNA splicing variant. In some embodiments, provided technologies profile one or more splicing variants of a gene, e.g., locations and quantities of one or more splicing variant of a gene. In some embodiments, provided methods or compositions profile different splicing variants. In some embodiments, an exon that contains one or more variants is targeted and barcoded by sequential hybridization and barcoding. In some embodiments, a splicing variant contains one or more distinguishable sequences resulted from splicing, and such sequences are targeted. In some embodiments, by targeting exons and/or distinguishable sequences, provided technologies can profile one or more specific splicing variants, or an entire splicing repertoire of an mRNA. As widely known in the art, mRNA splicing are important to numerous biological processes and diseases, for example, neurological diseases like autism or Down syndrome. Molecules responsible for cell-to-cell adhesion and synpatogenesis are spliced and their defects are known to generate miswiring in the brain and cause diseases.

In some embodiments, detectably labeled oligonucleotides target sequence modifications caused by sequence editing, chemical modifications and/or combinations thereof. In some embodiments, a modified nucleic acid target, optionally after a conversion process, hybridizes with one or more different complementary sequences compared to an un-modified target, and is profiled using one or more oligonucleotides that selectively hybridizes with the modified nucleic acid. In some embodiments, a target is an RNA through by RNA editing (Brennicke, A., A. Marchfelder, et al. (1999). "RNA editing". *FEMS Microbiol Rev* 23 (3): 297-316). In some embodiments, provided technologies profiles different RNA variants formed by RNA editing. In some embodiments, provided technologies profile modified oligonucleotide. In some embodiments, provided technologies profiles methylated RNA (Song C X, Yi C, He C. Mapping recently identified nucleotide variants in the genome and transcriptome. Nat Biotechnol. 2012 November; 30(11):1107-16). In some embodiments, provided technologies profile methylated DNA. In some embodiments, a target is single-nucleotide polymorphism (SNP).

In some embodiments, by profiling a target, provided technologies provide, among other things, quantitative and/or positioning information of a target, in some cases, in single cells, a tissue, an organ, or an organism. In some embodiments, profiling of transcripts can be used to qualitatively and/or quantitatively define the spatial-temporal patterns of gene expression within cells, tissues, organs or organisms.

In some embodiments, each detectably labeled oligonucleotide in a set has a different target, e.g., a transcript or DNA locus. In some embodiments, two or more detectably labeled oligonucleotides in a set have the same target. In some embodiments, two or more detectably labeled oligonucleotides target the same transcript. In some embodiments, two or more detectably labeled oligonucleotides target the same DNA locus. In some embodiments, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90 or 100 detectably labeled oligonucleotides the same target. In some embodiments, two or more detectably labeled oligonucleotides target the same target. In some embodiments, five or more detectably labeled oligonucleotides target the same target. In some embodiments, 10 or more detectably labeled oligonucleotides target the same target. In some embodiments, 15 or more detectably labeled oligonucleotides target the same target. In some embodiments, 20 or more detectably labeled oligonucleotides target the same target. In some embodiments, 25 or more detectably labeled oligonucleotides target the same target. In some embodiments, 30 or more detectably labeled oligonucleotides target the same target. In some embodiments, 35 or more detectably labeled oligonucleotides target the same target. In some embodiments, 40 or more detectably labeled oligonucleotides target the same target. In some embodiments, 45 or more detectably labeled oligonucleotides target the same target. In some embodiments, 50 or more detectably labeled oligonucleotides target the same target. In some embodiments, 60 or more detectably labeled oligonucleotides target the same target. In some embodiments, 70 or more detectably labeled oligonucleotides target the same target. In some embodiments, 80 or more detectably labeled oligonucleotides target the same target. In some embodiments, 90 or more detectably labeled oligonucleotides target the same target. In some embodiments, 100 or more detectably labeled oligonucleotides target the same target. In some embodiments, about 1-10 detectably labeled oligonucleotides target the same target. In some embodiments, about 5-15 detectably labeled oligonucleotides target the same target. In some embodiments, about 10-20 detectably labeled oligonucleotides target the same target. In some embodiments, about 15-25 detectably labeled oligonucleotides target the same target. In some embodiments, about 20-30 detectably labeled oligonucleotides target the same target. In some embodiments, about 25-35 detectably labeled oligonucleotides target the same target. In some embodiments, about 30-40 detectably labeled oligonucleotides target the same target. In some embodiments, about 35-45 detectably labeled oligonucleotides target the same target. In some embodiments, about 40-50 detectably labeled oligonucleotides target the same target. In some embodiments, about 45-55 detectably labeled oligonucleotides target the same target. In some embodiments, about 50-70 detectably labeled oligonucleotides target the same target. In some embodiments, about 60-80 detectably labeled oligonucleotides target the same target. In some embodiments, about 70-90 detectably labeled oligonucleotides target the same target. In some embodiments, about 80-100 detectably labeled oligonucleotides target the same target.

In some embodiments, among other things, using multiple detectably labeled oligonucleotides for the same target increases signal intensity. In some embodiments, each detectably labeled oligonucleotide in a set targeting the same target interacts with a different portion of a target.

In some embodiments, all detectably labeled oligonucleotides for a target in a set have the same detectable moieties. In some embodiments, all detectably labeled oligonucleotides are labeled in the same way. In some embodiments, all the detectably labeled oligonucleotides for a target have the same fluorophore.

In some embodiments, detectably labeled oligonucleotides for a target are positioned within a targeted region of a target. A targeted region can have various lengths. In some embodiments, a targeted region is about 20 bp in length. In some embodiments, a targeted region is about 30 bp in length. In some embodiments, a targeted region is about 40 bp in length. In some embodiments, a targeted region is about 50 bp in length. In some embodiments, a targeted region is about 60 bp in length. In some embodiments, a targeted region is about 80 bp in length. In some embodiments, a targeted region is about 100 bp in length. In some embodiments, a targeted region is about 150 bp in length. In some embodiments, a targeted region is about 200 bp in length. In some embodiments, a targeted region is about 250 bp in length. In some embodiments, a targeted region is about 300 bp in length. In some embodiments, a targeted region is about 350 bp in length. In some embodiments, a targeted region is about 400 bp in length. In some embodiments, a targeted region is about 450 bp in length. In some embodiments, a targeted region is about 500 bp in length. In some embodiments, a targeted region is about 600 bp in length. In some embodiments, a targeted region is about 700 bp in length. In some embodiments, a targeted region is about 800 bp in length. In some embodiments, a targeted region is about 900 bp in length. In some embodiments, a targeted region is about 1,000 bp in length. In some embodiments, detectably labeled oligonucleotides for a target are positioned in proximity to each other on the target.

As understood by a person having ordinary skill in the art, different technologies can be used for the imaging steps. Exemplary methods include but are not limited to epifluorescence microscopy, confocal microscopy, the different types of super-resolution microscopy (PALM/STORM, SSIM/GSD/STED), and light sheet microscopy (SPIM and etc).

Exemplary super resolution technologies include but are not limited to I$^5$M and 4Pi-microscopy, Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof. For examples: Chi, 2009 "Super-resolution microscopy: breaking the limits, Nature Methods 6(1):15-18; Blow 2008, "New ways to see a smaller world," Nature 456:825-828; Hell, et al., 2007, "Far-Field Optical Nanoscopy," *Science* 316: 1153; R. Heintzmann and G. Ficz, 2006, "Breaking the resolution limit in light microscopy," *Briefings in Functional Genomics and Proteomics* 5(4):289-301; Garini et al., 2005, "From micro to nano: recent advances in high-resolution microscopy," *Current Opinion in Biotechnology* 16:3-12; and Bewersdorf et al., 2006, "Comparison of I$^5$M and 4Pi-microscopy," 222(2):105-117; and Wells, 2004, "Man the Nanoscopes," *JCB* 164(3):337-340.

In some embodiments, electron microscopes (EM) are used.

In some embodiments, an imaging step detects a target. In some embodiments, an imaging step localizes a target. In some embodiments, an imaging step provides three-dimensional spatial information of a target. In some embodiments, an imaging step quantifies a target. By using multiple contacting and imaging steps, provided methods are capable of providing spatial and/or quantitative information for a large number of targets in surprisingly high throughput. For example, when using F detectably different types of labels, spatial and/or quantitative information of up to F$^N$ targets can be obtained after N contacting and imaging steps.

In some embodiments, provided methods comprise additional steps before or after a contacting and/or an imaging step. In some embodiments, provided methods comprise a step of removing a plurality of detectably labeled oligonucleotides after each imaging step. In some embodiments, a step of removing comprises degrading the detectably labeled oligonucleotides. In some embodiments, a step of removing does not significantly degrade a target, so that a target can be used for the next contacting and/or imaging step(s) if desired. In some embodiments, a step of removing comprises contacting the plurality of detectably labeled oligonucleotides with an enzyme that digests a detectably labeled oligonucleotide. In some embodiments, a step of removing comprises contacting the plurality of detectably labeled oligonucleotides with a DNase or RNase. For example, in some embodiments, a detectably labeled oligonucleotide comprises a DNA sequence, and a DNase is used for its degradation; in some other embodiments, a detectably labeled oligonucleotide comprises an RNA sequence, and an RNase is used for its degradation. In some embodiments, a step of removing comprises degrading a detectable moiety. In some embodiments, a step of removing comprises photobleaching.

In some embodiments, targets of one set of detectably labeled oligonucleotides are also targets of another set. In some embodiments, targets of one set of detectably labeled oligonucleotides overlap with those of another set. In some embodiments, the overlap is more than 10%. In some embodiments, the overlap is more than 20%. In some embodiments, the overlap is more than 30%. In some embodiments, the overlap is more than 40%. In some embodiments, the overlap is more than 50%. In some embodiments, the overlap is more than 60%. In some embodiments, the overlap is more than 70%. In some embodiments, the overlap is more than 80%. In some embodiments, the overlap is more than 90%. In some embodiments, the overlap is more than 91%. In some embodiments, the overlap is more than 92%. In some embodiments, the overlap is more than 93%. In some embodiments, the overlap is more than 94%. In some embodiments, the overlap is more than 90%. In some embodiments, the overlap is more than 95%. In some embodiments, the overlap is more than 96%. In some embodiments, the overlap is more than 97%. In some embodiments, the overlap is more than 98%. In some embodiments, the overlap is more than 99%. In some embodiments, the overlap is more than 99.5%. In some embodiments, the overlap is more than 99.6%. In some embodiments, the overlap is more than 99.7%. In some embodiments, the overlap is more than 99.8%. In some embodiments, the overlap is more than 99.9%. In some embodiments, the overlap is 100%. In some embodiments, targets of one set of detectably labeled oligonucleotides are the same as targets of another set. In some embodiments, each set of detectably labeled oligonucleotides targets the same targets.

In some embodiments, a third detectably labeled oligonucleotide in a second contacting step targeting the first transcript or DNA locus (the first target) optionally has an identical sequence to the first detectably labeled oligonucleotide targeting the first transcript or DNA locus. In some embodiments, the sequences are identical. In some embodiments, the sequences are different. Similarly, in some embodiments, a fourth detectably labeled oligonucleotide in a second contacting step targeting the second transcript or DNA locus (the first target) optionally has an identical sequence to the second detectably labeled oligonucleotide targeting the first transcript or DNA locus. In some embodiments, the sequences are identical. In some embodiments, the sequences are different.

In some embodiments, the second plurality differs from the first plurality in that at least one of the oligonucleotides present in the second plurality is labeled with a different detectable moiety than the corresponding oligonucleotide targeting the same transcript or DNA locus in the first plurality. In some embodiments, each plurality of detectably labeled oligonucleotides is different from another, in that at least one of the oligonucleotides present in a plurality is labeled with a different detectable moiety than the corresponding oligonucleotide targeting the same transcript or DNA locus in another plurality.

In some embodiments, a detectably labeled oligonucleotide has the structure of $[S]-[L]$, wherein $[S]$ is an oligonucleotide sequence, $[L]$ is a detectable moiety or a combination of detectable moieties. In some embodiments, $[L]$ comprises multiple units of detectable labels, e.g., fluorophores, each of which independently associates with one or more nucleotidic moieties of an oligonucleotide sequence, e.g., $[S]$. In some embodiments, each detectable label attached to the same detectably labeled oligonucleotide provides the same detectable signal. In some embodiments, all detectable labels attached to the same oligonucleotide sequence are the same.

In some embodiments, oligonucleotides targeting the same target have the same set of sequences among two or more sets of detectably labeled oligonucleotides, i.e., the differences, if any, among the detectably labeled oligonucleotides are within the detectable moieties, not the sequences. For example, in one set of detectably labeled oligonucleotides, the detectably labeled oligonucleotides targeting a first target all have the same detectable moiety, or combination of detect moieties $[L]_1$:

$[S]_1-[L]_1, [S]_2-[L]_1, \ldots, [S]_n-[L]_1$, wherein n is the number of detectably labeled oligonucleotides for a target, e.g., an integer of 3-50;

In another set of detectably labeled oligonucleotides, wherein oligonucleotides targeting the same target are differently labeled, the oligonucleotides targeting the same target are having the same set of oligonucleotide sequences $([S]_1, [S]_2, \ldots, [S]_n)$ yet a different $[L]_2$:

$[S]_1-[L]_2, [S]_2-[L]_2, \ldots, [S]_n-[L]_2$, wherein $[L]_1$ is detectably different than $[L]_2$.

To exemplify certain embodiments of the present invention, a two-step, two-label, 4-target $(F^N=2^2=4)$ process, wherein all detectably labeled oligonucleotides targeting the same target in each set independently have the same detectable moiety, is provided below:

Step 1. Contacting the targets with the first plurality (P1) of detectably labeled oligonucleotides:

Target T1: $[S]_{P1-T1-1}[L]_1$, $[S]_{P1-T1-2}[L]_1$, $[S]_{P1-T1-3}[L]_1, \ldots, [S]_{P1-T1-P1T1}[L]_1$, wherein P1T1 is the number of detectably labeled oligonucleotides targeting T1 in the first plurality, and $[L]_1$ is the first detectable label;

Target T2: $[S]_{P1-T2-1}[L]_1$, $[S]_{P1-T2-2}[L]_1$, $[S]_{P1-T2-3}[L]_1, \ldots, [S]_{P1-T2-P1T2}[L]_1$, wherein P1T2 is the number of detectably labeled oligonucleotides targeting T2 in the first plurality;

Target T3: $[S]_{P1-T1-1}[L]_2$, $[S]_{P1-T3-2}[L]_2$, $[S]_{P1-T3-3}[L]_2, \ldots, [S]_{P1-T3-P1T3}[L]_2$, wherein P1T3 is the number of detectably labeled oligonucleotides targeting T3 in the first plurality, and $[L]_2$ is a detectably different label than $[L]_1$;

Target T4: $[S]_{P1-T4-1}[L]_2$, $[S]_{P1-T4-2}[L]_2$, $[S]_{P1-T4-3}[L]_2, \ldots, [S]_{P1-T4-P1T4}[L]_2$, wherein P1T4 is the number of detectably labeled oligonucleotides targeting T4 in the first plurality.

Step 2: Imaging;

Step 3: Removing P1 from the targets;

Step 4: Contacting the targets with the second plurality (P2) of detectably labeled oligonucleotides:

Target T1: $[S]_{P2-T1-1}[L]_1$, $[S]_{P2-T1-2}[L]_1$, $[S]_{P2-T1-3}[L]_1, \ldots, [S]_{P2-T1-P2T1}[L]_1$, wherein P2T1 is the number of detectably labeled oligonucleotides targeting T1 in the second plurality;

Target T2: $[S]_{P2-T2-1}[L]_2$, $[S]_{P2-T2-2}[L]_2$, $[S]_{P2-T2-3}[L]_2, \ldots, [S]_{P2-T2-P2T2}[L]_2$, wherein P2T2 is the number of detectably labeled oligonucleotides targeting T2 in the second plurality;

Target T3: $[S]_{P2-T3-1}[L]_1$, $[S]_{P2-T3-2}[L]_1$, $[S]_{P2-T3-3}[L]_1, \ldots, [S]_{P2-T3-P2T3}[L]_1$, wherein P2T3 is the number of detectably labeled oligonucleotides targeting T3 in the second plurality;

Target T4: $[S]_{P2-T4-1}[L]_2$, $[S]_{P2-T4-2}[L]_2$, $[S]_{P2-T4-3}[L]_2, \ldots, [S]_{P2-T4-P2T4}[L]_2$, wherein P2T4 is the number of detectably labeled oligonucleotides targeting T4 in the second plurality.

Step 5: Imaging.

After the two imaging steps, each target has its own unique sequential barcode:

T1: $[L]_1[L]_1$;

T2: $[L]_1[L]_2$;

T3: $[L]_2[L]_1$; and

T4: $[L]_2[L]_2$.

In some embodiments, additional barcodes, T1--, T2--, --T1, --T2 can also be used, wherein --indicates no signal for that step.

In the exemplified process above, each of P1T1, P1T2, P1T3, P1T4, P2T1, P2T2, P2T3 and P2T4 is independently a natural number (an integer greater than 0). In some embodiments, P1T1=P2T1. In some embodiments, P1T2=P2T2. In some embodiments, P1T3=P2T3. In some embodiments, P1T4=P2T4. In some embodiments, one detectably labeled oligonucleotide is used for a target. In some embodiments, two or more detectably labeled oligonucleotides are used for a target.

In some embodiments, detectably labeled oligonucleotides targeting the same target have the same set of sequences in each plurality. For example, for target T1 in the example above, each of $[S]_{P1-T1-1}$ to $[S]_{P1-T1-P1T1}$ independently has the same sequence as one of $[S]_{P2-T1-1}$ to $[S]_{P2-T1-P2T1}$, and each of $[S]_{P2-T1-1}$ to $[S]_{P2-T1-P2T1}$ independently has the same sequence as one of $[S]_{P1-T1-1}$ to $[S]_{P1-T1-P1T1}$. In some embodiments, detectably labeled oligonucleotides targeting the same target have different sets of sequences in each plurality.

In some embodiments, provided methods optionally comprise a step of removing a plurality of detectably labeled oligonucleotides after an imaging step. In some embodiments, provided methods comprise a removing step after an imaging step. In some embodiments, provided methods comprise a removing step after each imaging step but the last imaging step. In some embodiments, provided methods comprise a removing step after each imaging step.

A removing step in provided methods can serve one or more of a variety of purposes. In some embodiments, a removing step removes a plurality of detectably labeled oligonucleotides from targets so that targets are available for interacting with another plurality of detectably labeled oligonucleotides. In some embodiments, a removing step removes a plurality of detectably labeled oligonucleotides so that detectable moieties of one plurality of detectably labeled oligonucleotides do not interfere with detection of another plurality of detectably labeled oligonucleotides bound to targets. In some embodiments, a removing step removes at least 80% detectably labeled oligonucleotides. In some embodiments, a removing step removes at least 85% detectably labeled oligonucleotides. In some embodiments, a removing step removes at least 90% detectably labeled oligonucleotides. In some embodiments, a removing step removes at least 91% detectably labeled oligonucleotides. In some embodiments, a removing step removes at least 92% detectably labeled oligonucleotides. In some embodiments, a removing step removes at least 93% detectably labeled oligonucleotides. In some embodiments, a removing step removes at least 94% detectably labeled oligonucleotides. In some embodiments, a removing step removes at least 95% detectably labeled oligonucleotides. In some embodiments, a removing step removes at least 96% detectably labeled oligonucleotides. In some embodiments, a removing step removes at least 97% detectably labeled oligonucleotides. In some embodiments, a removing step removes at least 98% detectably labeled oligonucleotides. In some embodiments, a removing step removes at least 99% detectably labeled oligonucleotides. In some embodiments, a removing step removes at least 99.1% detectably labeled oligonucleotides. In some embodiments, a removing step removes at least 99.2% detectably labeled oligonucleotides. In some embodiments, a removing step removes at least 99.3% detectably labeled oligonucleotides. In some embodiments, a removing step removes at least 99.4% detectably labeled oligonucleotides. In some embodiments, a removing step removes at least 99.5% detectably labeled oligonucleotides. In some embodiments, a removing step removes at least 80% of the detectable signal. In some embodiments, a removing step removes at least 85% of the detectable signal. In some embodiments, a removing step removes at least 90% of the detectable signal. In some embodiments, a removing step removes at least 91% of the detectable signal. In some embodiments, a removing step removes at least 92% of the detectable signal. In some embodiments, a removing step removes at least 93% of the detectable signal. In some embodiments, a removing step removes at least 94% of the detectable signal. In some embodiments, a removing step removes at least 95% of the detectable signal. In some embodiments, a removing step removes at least 96% of the detectable signal. In some embodiments, a removing step removes at least 97% of the detectable signal. In some embodiments, a removing step removes at least 98% of the detectable signal. In some embodiments, a removing step removes at least 99% of the detectable signal. In some embodiments, a removing step removes at least 99.5% of the detectable signal. In some embodiments, a removing step removes 100% of the detectable signal. In some embodiments, after a removing step no signal can be detected by an imaging step.

A removing step optionally preserves targets (e.g., transcripts or DNA loci) for further use, for example, further detection or quantification by additional contacting and/or imaging steps. In some embodiments, a removing step preserves at least 80% targets. Percentage of preserved targets can be measured, for example, by comparing data collected before and after a removing step, optionally using the same contacting and imaging protocols. In some embodiments, a removing step preserves at least 85% targets. In some embodiments, a removing step preserves at least 90% targets. In some embodiments, a removing step preserves at least 91% targets. In some embodiments, a removing step preserves at least 92% targets. In some embodiments, a removing step preserves at least 93% targets. In some embodiments, a removing step preserves at least 94% targets. In some embodiments, a removing step preserves at least 95% targets. In some embodiments, a removing step preserves at least 96% targets. In some embodiments, a removing step preserves at least 97% targets. In some embodiments, a removing step preserves at least 98% targets. In some embodiments, a removing step preserves at least 99% targets.

Methods for removing detectably labeled oligonucleotides are widely known in the art. In some embodiments, a removing step comprising degrading a detectably labeled oligonucleotide. In some embodiments, a detectably labeled oligonucleotide is removed by enzymatic digestion. In some embodiments, a removing step comprising contacting a plurality of detectably labeled oligonucleotides with an enzyme that digests a detectably labeled oligonucleotide.

Suitable enzymes are widely used in the art. For example, depending on the type(s) of detectably labeled oligonucleotides and/or targets, either DNase or RNase can be used. In some embodiments, a detectably labeled oligonucleotide comprising a DNA sequence for detecting/quantifying a RNA target is digested by a DNase, e.g., DNase I. In some embodiments, a detectably labeled oligonucleotide comprising an RNA sequence for detecting/quantifying a DNA target is digested by a RNase. In some embodiments, a detectably labeled RNA oligonucleotide is used to target a DNA loci.

In some embodiments, a detectably labeled oligonucleotide interacts with its target through binding or hybridization to one or more intermediate, such as an oligonucleotide, that is bound, hybridized, or otherwise linked to the target. In some embodiments, a detectably labeled oligonucleotide interacts with a target through hybridization with an intermediate oligonucleotide hybridized to a target, wherein the intermediate oligonucleotide comprises a sequence complimentary to the target, and a sequence complementary to the detectably labeled oligonucleotide (overhang). In some embodiments, a removing step removes detectably labeled oligonucleotides, optionally keeping intermediate oligonucleotides intact. In some embodiments, a removing step removes detectably labeled oligonucleotides and keeps intermediate oligonucleotides intact. In some embodiments, detectably labeled oligonucleotides differ from intermediates in a chemical or enzymatic perspective, so that detectably labeled oligonucleotides can be selectively removed.

In some embodiments, intermediate DNA oligonucleotides are used to hybridize against DNA loci, with an overhang (e.g., 20 nt) such that a bridge oligonucleotide comprising an RNA sequence and with complementary sequence (e.g., RNA bridge probe) can bind. An RNA bridge probe can be labeled directly with a dye or a HCR polymer (which can also be DNA). After imaging, RNase can be used to digest away the RNA bridge probes, while leaving the DNA probe intact hybridized on the DNA loci. Such a method provides multiple advantages. For example, subsequent contacting steps only involve RNA bridge probes hybridizing against DNA oligonucleotides with overhangs, and avoid getting double stranded DNA to melt and hybridize with DNA oligonucleotides, which can be a difficult process. Further, the overhang can be made to be the same for all DNA oligonucleotides (e.g., 20-40) targeting the same gene, so that only one type of RNA bridge probe is needed per gene per round of hybridization. To switch colors on different hybridization (contacting steps), one can change RNA bridge probes with a different label or different HCR polymer. DNA bridge probes that can be specifically removed, e.g., with a specific enzyme restriction site like EcoRI on the bridge or the HCR hairpins, can also be used. Incubating the cells with the appropriate nuclease can digest away all detectable moieties without affecting the DNA loci and/or the probe hybridized on them.

In some embodiments, detectably labeled oligonucleotides comprises 5' phosphorylation and can be degraded by Lambda exonuclease, while intermediate oligonucleotides are not 5'-phosphorolated and cannot be degraded by Lambda exonuclease.

In some embodiments, a detectably labeled oligonucleotide comprises uracil. In some embodiments, detectably labeled oligonucleotides contain uracil, and can be degraded by USER™ enzyme (New England BioLabs, Ipswich, Massachusetts, Mass., US), while intermediate oligonucleotides contain no uracil and cannot be degraded by USER™ enzyme.

In some embodiments, an oligonucleotide hybridized against an overhang of an intermediate oligonucleotide has a recessed 3'-end when hybridized against the overhang. Detectably labeled oligonucleotides with recessed 3'-end when hybridized against intermediate oligonucleotides can be selectively digested by Exonuclease III. Intermediate oligonucleotides which do not have recessed 3'-ends, or whose 3'-ends are in RNA-DNA duplexes, can be kept intact due to the much weaker activities of exonuclease III toward them.

In some embodiments, when an enzyme is involved, a removing step is performed at a temperature that produces optimal results. In some embodiments, a removing step is performed at about 37° C. In some embodiments, a removing step is performed at room temperature. In some embodiments, digestion with Lambda exonuclease is conducted at about 37° C. In some embodiments, digestion with USER™ enzyme is conducted at about 37° C. In some embodiments, digestion with USER™ enzyme is conducted at room temperature. In some embodiments, digestion with Exonuclease III is conducted at about 37° C. In some embodiments, digestion with Exonuclease III is conducted at room temperature.

In some embodiments, use of an intermediate oligonucleotide and an overhang sequence for detectably labeled oligonucleotide binding provides a variety of advantages. In some embodiments, kinetics of hybridization between an overhang sequence and a detectably labeled oligonucleotide is faster than that between an intermediate oligonucleotide and a target. In some embodiments, all intermediate oligonucleotides for a target comprise the same overhang sequence, and all detectably labeled oligonucleotides for a target comprises the same complimentary sequence for binding to the same overhang sequence. In some embodiments, hybridization between a set of detectably labeled oligonucleotides and a set of intermediate oligonucleotides is up to about 20-40 times faster than that between a set of an intermediate oligonucleotides and a set of targets. In some embodiments, hybridization between detectably labeled oligonucleotides and intermediate oligonucleotides can be done in 30 minutes, compared to, in some cases, up to about 12 hours for hybridization between intermediate oligonucleotides and targets.

In some embodiments, strand displacement is used in a removing step to remove a detectably labeled oligonucleotide. In some embodiments, heat is used to dissociate a detectably labeled oligonucleotide in a removing step.

In some embodiments, a removing step comprises photobleaching. In some embodiments, photobleaching destroys a dye, such as a fluorophore, of a detectably labeled oligonucleotide.

In some embodiments, a first and a second sets of detectably labeled oligonucleotides target different sequences of each target, and a removing step after a first imaging step is optional. For example, one strategy is to target the same RNA with different DNA probes (detectably labeled DNA oligonucleotides), such that the first plurality of probes can target one set of sequences on the RNA, and the second plurality of probes target a different set of sequences on the same RNA. On the first hybridization (contacting), the first plurality of probes is used. They can then be imaged and optionally photobleached or digested by DNase, or other methods of destroying either the oligos or the dyes. The second set of probes can be hybridized and imaged without interferences from the first set of probes.

In some embodiments, provide methods optionally comprise HCR, light sheet microscopy, CLARITY, or combinations thereof. In some embodiments, provided methods allow direct profiling of targets in a tissue, an organ or an organism. In some embodiments, an organ is a brain. In some embodiments, provided methods allow direct imaging of transcripts in intact brains or tissues. In some embodiments, provided methods further comprise HCR. In some embodiments, provided methods further comprise light sheet microscopy. In some embodiments, provided methods further comprise CLARITY.

Provided methods offer many advantages over methods prior to the present invention. For example, in some embodiments, provided methods provide high-throughput at reasonable cost. In some embodiments, provided methods provide direct probing of target without transformation or amplification of a target. In some embodiments, provided methods enable quick scale up without the requirement of a large number of detectable labels. In some embodiments, provided methods can apply multiple labels to the same target and therefore increase signal intensity. In some embodiments, provided methods provide a combination of the advantages.

In some embodiments, the present invention provides compositions comprising a plurality of detectably labeled oligonucleotides, for, e.g., use in provided methods. Exemplary compositions include but are not limited to those described in exemplary method embodiments herein.

In some embodiments, the present invention provides compositions comprising a plurality of detectably labeled oligonucleotides, each of which targets a nucleic acid and is labeled with a detectable moiety, so that the composition comprises at least:

(i) a first oligonucleotide targeting a first nucleic acid and labeled with a first detectable moiety; and (ii) a second oligonucleotide targeting a second nucleic acid and labeled with a second detectable moiety.

In some embodiments, the present invention provides compositions comprising a plurality of detectably labeled oligonucleotides, each of which targets a transcript or DNA locus and is labeled with a detectable moiety, so that the composition comprises at least:

(i) a first oligonucleotide targeting a first transcript or DNA locus and labeled with a first detectable moiety; and (ii) a second oligonucleotide targeting a second transcript or DNA locus and labeled with a second detectable moiety.

In some embodiments, the present invention provides kits comprising a plurality of detectably labeled oligonucleotides, each of which targets a transcript or DNA locus and is labeled with a detectable moiety, so that the kit comprises at least:

(i) a first oligonucleotide targeting a first transcript or DNA locus and labeled with a first detectable moiety;

(ii) a second oligonucleotide targeting a second transcript or DNA locus and labeled with a second detectable moiety.

(iii) a third oligonucleotide, optionally identical in sequence to the first oligonucleotide, targeting the first transcript or DNA locus and labeled with the first, the second or a third detectable moiety; and (iv) a fourth oligonucleotide, optionally identical in sequence to the second oligonucleotide, targeting the second transcript or DNA locus, and labeled with the first, the second, the third or a fourth detectable moiety, wherein either the third oligonucleotide is labeled with a different detectable moiety than the first oligonucleotide, or the fourth oligonucleotide is labeled with a different detectable moiety than the second oligonucleotide, or both.

In some embodiments, detectably labeled oligonucleotides targeting the same target (transcript or DNA locus) in a composition are labeled with moieties providing the same detectable signal, or detectable signals that cannot be differentiated in an imaging step. In some embodiments, detectably labeled oligonucleotides targeting the same target in a composition are labeled with the same detectable moiety.

In some embodiments, a detectable moiety is or comprises a fluorophore. In some embodiments, a detectable moiety is a fluorophore. Exemplary fluorophores are widely known and used in the art, for example but not limited to fluorescein, rhodamine, Alexa Fluors, DyLight fluors, ATTO Dyes, or any analogs or derivatives thereof.

In some embodiments, a first and a second detectably labeled oligonucleotides target different target. In some embodiments, a first and a second detectably labeled oligonucleotides target the same target. In some embodiments, detectably labeled oligonucleotides in a composition or a kit targets two or more targets, e.g., transcripts and/or DNA loci. In some embodiments, detectably labeled oligonucleotides in a composition or a kit targets two or more transcripts. In some embodiments, detectably labeled oligonucleotides in a composition or a kit targets two or more DNA loci. In some embodiments, detectably labeled oligonucleotides in a composition or kit targets at least 4 targets. In some embodiments, detectably labeled oligonucleotides in a composition or kit targets at least 9 targets. In some embodiments, detectably labeled oligonucleotides in a composition or kit targets at least 16 targets. In some embodiments, detectably labeled oligonucleotides in a composition or kit targets at least 25 targets. In some embodiments, detectably labeled oligonucleotides in a composition or kit targets at least 36 targets. In some embodiments, detectably labeled oligonucleotides in a composition or kit targets at least 50 targets. In some embodiments, detectably labeled oligonucleotides in a composition or kit targets at least 100 targets. In some embodiments, detectably labeled oligonucleotides in a composition or kit targets at least 200 targets. In some embodiments, detectably labeled oligonucleotides in a composition or kit targets at least 500 targets. In some embodiments, detectably labeled oligonucleotides in a composition or kit targets at least 1,000 targets. In some embodiments, detectably labeled oligonucleotides in a composition or kit targets at least 5,000 targets. In some embodiments, detectably labeled oligonucleotides in a composition or kit targets at least 10,000 targets. In some embodiments, detectably labeled oligonucleotides in a composition or kit targets at least 50,000 targets. In some embodiments, detectably labeled oligonucleotides in a composition or kit targets at least 100,000 targets. In some embodiments, detectably labeled oligonucleotides in a composition or kit targets at least 1,000,000 targets.

In some embodiments, a first and a second oligonucleotides have different oligonucleotide sequences. In some embodiments, a first and a second detectable moieties are different. In some embodiments, a first and a second detectable moieties are the same.

In some embodiments, a first and a second oligonucleotides share less than 5% sequence identity. In some embodiments, a first and a second oligonucleotides share less than 10% sequence identity. In some embodiments, a first and a second oligonucleotides share less than 20% sequence identity. In some embodiments, a first and a second oligonucleotides share less than 30% sequence identity. In some embodiments, a first and a second oligonucleotides share less than 40% sequence identity. In some embodiments, a first and a second oligonucleotides share less than 50% sequence identity. In some embodiments, a first and a second oligonucleotides share less than 60% sequence identity. In some embodiments, a first and a second oligonucleotides share less than 65% sequence identity. In some embodiments, a first and a second oligonucleotides share less than 68% sequence identity. In some embodiments, a first and a second oligonucleotides share less than 70% sequence identity. In some embodiments, a first and a second oligonucleotides share less than 80% sequence identity. In some embodiments, a first and a second oligonucleotides share less than 90% sequence identity.

In some embodiments, each oligonucleotide shares less than 5% sequence identity with any other oligonucleotide. In some embodiments, each oligonucleotide shares less than 10% sequence identity with any other oligonucleotide. In some embodiments, each oligonucleotide shares less than 20% sequence identity with any other oligonucleotide. In some embodiments, each oligonucleotide shares less than 30% sequence identity with any other oligonucleotide. In some embodiments, each oligonucleotide shares less than 40% sequence identity with any other oligonucleotide. In some embodiments, each oligonucleotide shares less than 50% sequence identity with any other oligonucleotide. In some embodiments, each oligonucleotide shares less than 55% sequence identity with any other oligonucleotide. In some embodiments, each oligonucleotide shares less than 60% sequence identity with any other oligonucleotide. In some embodiments, each oligonucleotide shares less than 65% sequence identity with any other oligonucleotide. In some embodiments, each oligonucleotide shares less than 68% sequence identity with any other oligonucleotide. In some embodiments, each oligonucleotide shares less than 70% sequence identity with any other oligonucleotide. In some embodiments, each oligonucleotide shares less than 80% sequence identity with any other oligonucleotide. In some embodiments, each oligonucleotide shares less than 90% sequence identity with any other oligonucleotide.

In some embodiments, a composition or kit comprises two or more detectably labeled oligonucleotides targeting the same target. In some embodiments, 5, 10, 20, 30, 40, 50 or more detectably labeled oligonucleotides target the same target.

Detectably labeled oligonucleotides can be of various suitable lengths. In some embodiments, a detectably labeled oligonucleotide is 15 base pairs in length. In some embodiments, a detectably labeled oligonucleotide is 16 base pairs in length. In some embodiments, a detectably labeled oligonucleotide is 17 base pairs in length. In some embodiments, a detectably labeled oligonucleotide is 18 base pairs in length. In some embodiments, a detectably labeled oligonucleotide is 19 base pairs in length. In some embodiments, a detectably labeled oligonucleotide is 20 base pairs in length. In some embodiments, a detectably labeled oligonucleotide is 21 base pairs in length. In some embodiments, a detectably labeled oligonucleotide is 22 base pairs in length. In some embodiments, a detectably labeled oligonucleotide is 23 base pairs in length. In some embodiments, a detectably labeled oligonucleotide is 24 base pairs in length. In some embodiments, a detectably labeled oligonucleotide is 25 base pairs in length. In some embodiments, a detectably labeled oligonucleotide is 26 base pairs in length. In some embodiments, a detectably labeled oligonucleotide is 27 base pairs in length. In some embodiments, a detectably labeled oligonucleotide is 28 base pairs in length. In some embodiments, a detectably labeled oligonucleotide is 29 base pairs in length. In some embodiments, a detectably labeled oligonucleotide is 30 base pairs in length. In some embodiments, a detectably labeled oligonucleotide is at least 15 base pairs in length. In some embodiments, a detectably labeled oligonucleotide is at least 16 base pairs in length. In some embodiments, a detectably labeled oligonucleotide is at least 17 base pairs in length. In some embodiments, a detectably labeled oligonucleotide is at least 18 base pairs in length. In some embodiments, a detectably labeled oligonucleotide is at least 19 base pairs in length. In some embodiments, a detectably labeled oligonucleotide is at least 20 base pairs in length. In some embodiments, a detectably labeled oligonucleotide is at least 21 base pairs in length. In some embodiments, a detectably labeled oligonucleotide is at least 22 base pairs in length. In some embodiments, a detectably labeled oligonucleotide is at least 23 base pairs in length. In some embodiments, a detectably labeled oligonucleotide is at least 24 base pairs in length. In some embodiments, a detectably labeled oligonucleotide is at least 25 base pairs in length. In some embodiments, a detectably labeled oligonucleotide is at least 26 base pairs in length. In some embodiments, a detectably labeled oligonucleotide is at least 27 base pairs in length. In some embodiments, a detectably labeled oligonucleotide is at least 28 base pairs in length. In some embodiments, a detectably labeled oligonucleotide is at least 29 base pairs in length. In some embodiments, a detectably labeled oligonucleotide is at least 30 base pairs in length. In some embodiments, a detectably labeled oligonucleotide is at least 35 base pairs in length. In some embodiments, a detectably labeled oligonucleotide is at least 40 base pairs in length. In some embodiments, a detectably labeled oligonucleotide is at least 50 base pairs in length. In some embodiments, a detectably labeled oligonucleotide is about 15-25 base pairs in length. In some embodiments, a detectably labeled oligonucleotide is about 20-30 base pairs in length. In some embodiments, a detectably labeled oligonucleotide is about 25-35 base pairs in length. In some embodiments, a detectably labeled oligonucleotide is about 30-40 base pairs in length. In some embodiments, a detectably labeled oligonucleotide is about 35-45 base pairs in length. In some embodiments, a detectably labeled oligonucleotide is about 40-50 base pairs in length. In some embodiments, a detectably labeled oligonucleotide is about 15-30 base pairs in length. In some embodiments, a detectably labeled oligonucleotide is about 20-30 base pairs in length. In some embodiments, a detectably labeled oligonucleotide is about 15-35 base pairs in length. In some embodiments, a detectably labeled oligonucleotide is about 20-35 base pairs in length.

In some embodiments, a plurality of detectably labeled oligonucleotides contains two detectable moieties. In some embodiments, a plurality of detectably labeled oligonucleotides contains three detectable moieties. In some embodiments, a plurality of detectably labeled oligonucleotides contains four detectable moieties. In some embodiments, a plurality of detectably labeled oligonucleotides contains five detectable moieties. In some embodiments, a plurality of detectably labeled oligonucleotides contains six detectable moieties. In some embodiments, a plurality of detectably labeled oligonucleotides contains seven detectable moieties. In some embodiments, a plurality of detectably labeled oligonucleotides contains eight detectable moieties. In some embodiments, a plurality of detectably labeled oligonucleotides contains nine detectable moieties. In some embodiments, a plurality of detectably labeled oligonucleotides contains ten detectable moieties.

In some embodiments, a plurality of detectably labeled oligonucleotides comprises at least two detectable moieties. In some embodiments, a plurality of detectably labeled oligonucleotides comprises at least three detectable moieties. In some embodiments, a plurality of detectably labeled oligonucleotides comprises at least four detectable moieties. In some embodiments, a plurality of detectably labeled oligonucleotides comprises at least five detectable moieties. In some embodiments, a plurality of detectably labeled oligonucleotides comprises at least six detectable moieties. In some embodiments, a plurality of detectably labeled oligonucleotides comprises at least seven detectable moieties. In some embodiments, a plurality of detectably labeled oligonucleotides comprises at least eight detectable moieties. In some embodiments, a plurality of detectably labeled oligonucleotides comprises at least nine detectable moieties. In some embodiments, a plurality of detectably labeled oligonucleotides comprises at least ten detectable moieties.

In some embodiments, a composition further comprises:

(iii) a third oligonucleotide, optionally identical in sequence to the first oligonucleotide, targeting the first transcript or DNA locus; and (iv) a fourth oligonucleotide, optionally identical in sequence to the second oligonucleotide, targeting the second transcript or DNA locus wherein either the third oligonucleotide is labeled with a different detectable moiety than the first oligonucleotide, or the fourth oligonucleotide is labeled with a different detectable moiety than the second oligonucleotide, or both.

In some embodiments, a third oligonucleotide is identical in sequence to a first oligonucleotide. In some embodiments, a third oligonucleotide comprises a sequence overlapping with a first oligonucleotide. In some embodiments, a third oligonucleotide has less than 50% sequence identity with a first oligonucleotide. In some embodiments, a third oligonucleotide has less than 40% sequence identity with a first oligonucleotide. In some embodiments, a third oligonucleotide has less than 30% sequence identity with a first oligonucleotide. In some embodiments, a third oligonucleotide has less than 20% sequence identity with a first oligonucleotide. In some embodiments, a third oligonucleotide has less than 10% sequence identity with a first oligonucleotide. In some embodiments, a third oligonucleotide has less than 5% sequence identity with a first oligonucleotide.

In some embodiments, a fourth oligonucleotide is identical in sequence to a second oligonucleotide. In some embodiments, a fourth oligonucleotide comprises a sequence overlapping with a second oligonucleotide. In some embodiments, a fourth oligonucleotide has less than 50% sequence identity with a second oligonucleotide. In some embodiments, a fourth oligonucleotide has less than 40% sequence identity with a second oligonucleotide. In some embodiments, a fourth oligonucleotide has less than 30% sequence identity with a second oligonucleotide. In some embodiments, a fourth oligonucleotide has less than 20% sequence identity with a second oligonucleotide. In some embodiments, a fourth oligonucleotide has less than 10% sequence identity with a second oligonucleotide. In some embodiments, a fourth oligonucleotide has less than 5% sequence identity with a second oligonucleotide.

In some embodiments, a third oligonucleotide is labeled with a different detectable moiety than the first oligonucleotide. In some embodiments, a fourth oligonucleotide is labeled with a different detectable moiety than the second oligonucleotide.

In some embodiments, amount of a detectably labeled oligonucleotide in a plurality, composition, kit or method is pre-determined. In some embodiments, amounts of 5% detectably labeled oligonucleotides in a plurality, composition, kit or method are pre-determined. In some embodiments, amounts of 10% detectably labeled oligonucleotides in a plurality, composition, kit or method are pre-determined. In some embodiments, amounts of 20% detectably labeled oligonucleotides in a plurality, composition, kit or method are pre-determined. In some embodiments, amounts of 30% detectably labeled oligonucleotides in a plurality, composition, kit or method are pre-determined. In some embodiments, amounts of 40% detectably labeled oligonucleotides in a plurality, composition, kit or method are pre-determined. In some embodiments, amounts of 50% detectably labeled oligonucleotides in a plurality, composition, kit or method are pre-determined. In some embodiments, amounts of 60% detectably labeled oligonucleotides in a plurality, composition, kit or method are pre-determined. In some embodiments, amounts of 70% detectably labeled oligonucleotides in a plurality, composition, kit or method are pre-determined. In some embodiments, amounts of 80% detectably labeled oligonucleotides in a plurality, composition, kit or method are pre-determined. In some embodiments, amounts of 90% detectably labeled oligonucleotides in a plurality, composition, kit or method are pre-determined.

In some embodiments, amounts of at least 5 detectably labeled oligonucleotides in a plurality, composition, kit or method are pre-determined. In some embodiments, amounts of at least 10 detectably labeled oligonucleotides in a plurality, composition, kit or method are pre-determined. In some embodiments, amounts of at least 20 detectably labeled oligonucleotides in a plurality, composition, kit or method are pre-determined. In some embodiments, amounts of at least 30 detectably labeled oligonucleotides in a plurality, composition, kit or method are pre-determined. In some embodiments, amounts of at least 40 detectably labeled oligonucleotides in a plurality, composition, kit or method are pre-determined. In some embodiments, amounts of at least 50 detectably labeled oligonucleotides in a plurality, composition, kit or method are pre-determined. In some embodiments, amounts of at least 60 detectably labeled oligonucleotides in a plurality, composition, kit or method are pre-determined. In some embodiments, amounts of at least 70 detectably labeled oligonucleotides in a plurality, composition, kit or method are pre-determined. In some embodiments, amounts of at least 80 detectably labeled oligonucleotides in a plurality, composition, kit or method are pre-determined. In some embodiments, amounts of at least 90 detectably labeled oligonucleotides in a plurality, composition, kit or method are pre-determined. In some embodiments, amounts of at least each detectably labeled oligonucleotides in a plurality, composition, kit or method is pre-determined.

In some embodiments, two or more detectably labeled oligonucleotides are provided for one target. In some embodiments, total amount of all detectably labeled oligonucleotides for a target is pre-determined. In some embodiments, total amount of all detectably labeled oligonucleotides for a target is pre-determined, wherein the amount of each of the detectably labeled oligonucleotide for the target is independently and optionally pre-determined. In some embodiments, total amount of all detectably labeled oligonucleotides for each of a plurality of targets is independently pre-determined. In some embodiments, a plurality of targets has at least two targets. In some embodiments, a plurality of targets has at least five targets. In some embodiments, a plurality of targets has at least 10 targets. In some embodiments, a plurality of targets has at least 50 targets. In some embodiments, a plurality of targets has at least 100 targets. In some embodiments, a plurality of targets has at least 500 targets. In some embodiments, a plurality of targets has at least 1,000 targets.

In some embodiments, a target of a plurality, composition, kit or method is pre-determined. In some embodiments, at least 10 targets of a plurality, composition, kit or method are pre-determined. In some embodiments, at least 50 targets of a plurality, composition, kit or method are pre-determined. In some embodiments, at least 100 targets of a plurality, composition, kit or method are pre-determined. In some embodiments, at least 1,000 targets of a plurality, composition, kit or method are pre-determined. In some embodiments, up to $F^N$ targets of a plurality, composition, kit or method are pre-determined, wherein F is the number of detectable moieties in a pluralities, and N is the number of imaging steps.

Methods for synthesizing detectably labeled oligonucleotides are widely known and practiced in the art, for example, see Lubeck, E. & Cai, L. Nat. Methods 9, 743-48 (2012). Oligonucleotides are also commercially available from various vendors. In some embodiments, the present invention provides methods for preparing detectably labeled oligonucleotides. In some embodiments, the present invention provides methods for preparing intermediate oligonucleotides. In some embodiments, the present invention provides methods for preparing bridge oligonucleotides.

In some embodiments, the present invention provides methods for preparing a target nucleic acid having a first sequence, comprising steps of:

1) providing a first nucleic acid comprising the first sequence, wherein the first sequence is flanked by nicking endonuclease sites at both ends;

2) amplifying the first nucleic acid or part of the first nucleic acid to provide a second nucleic acid comprising the first sequence and the flanking nicking endonuclease sites; and 3) contacting the second nucleic acid with one or more nicking endonuclease corresponding to the flanking nicking endonuclease sites.

In some embodiments, a target nucleic acid having a first sequence is single-stranded. In some embodiments, an amplifying step comprises polymerase chain reaction (PCR). In some embodiments, provided methods further comprise a step of denaturing, wherein double-stranded second nucleic acid is denatured and the two strands become single-stranded. In some embodiments, provided methods further comprise isolating the nucleic acid having a first sequence. In some embodiments, a second nucleic acid is optionally modified before contacting with nicking endonucleases. In some embodiments, provided methods further comprise labeling a nucleic acid having a first sequence.

In some embodiments, the two flanking endonuclease sites are the same. In some embodiments, one nicking endonuclease corresponding to the same nicking endonuclease sites is used. In some embodiments, the two flanking endonuclease sites are different. In some embodiments, two nicking endonucleases, each of which independently corresponds to a nicking endonuclease site, are used.

Figure 25:
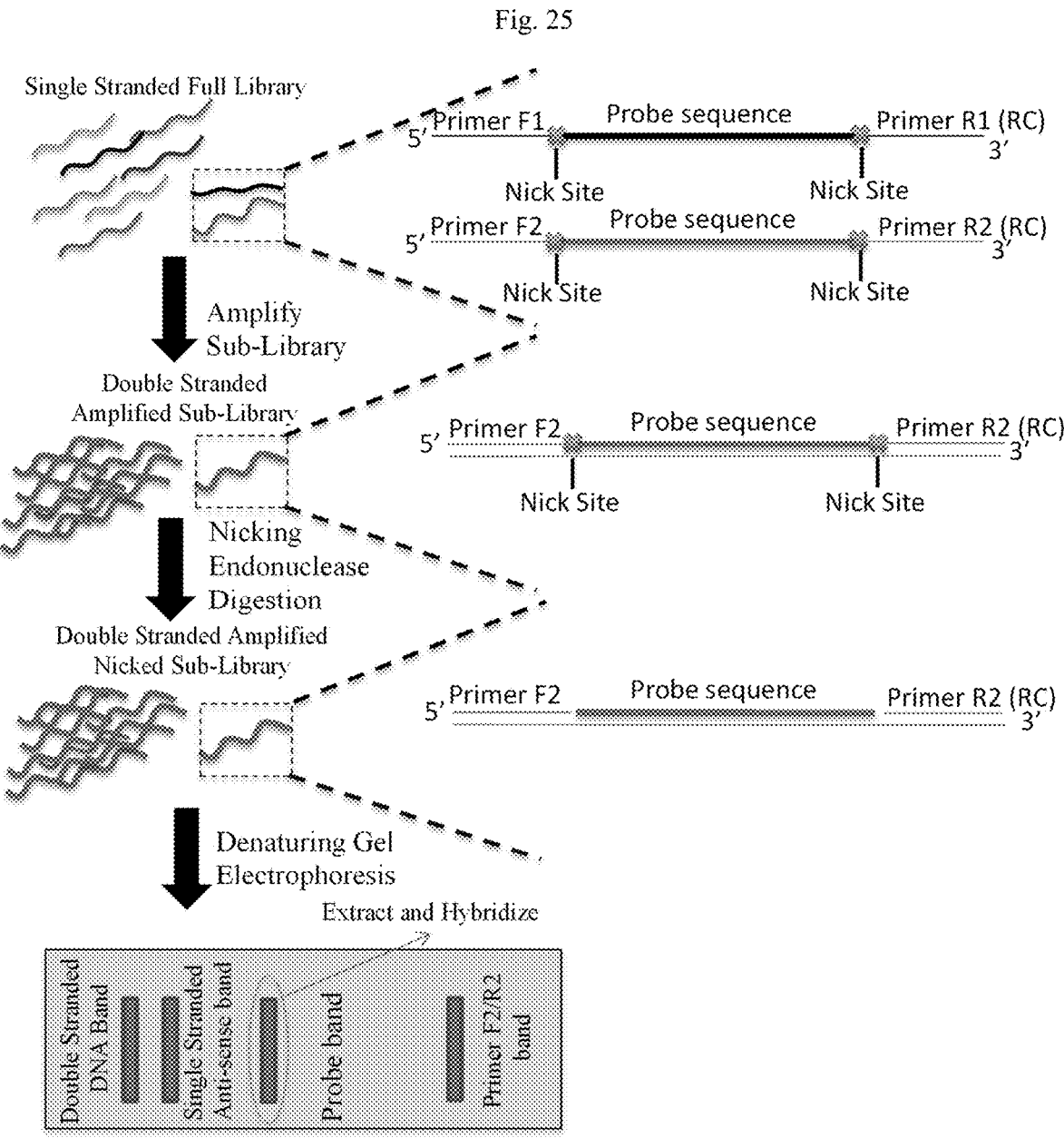
FIG. 25. Exemplary oligonucleotide preparation. The original oligonucleotide (as exemplified in this Figure, probe) library contains several probe sub-libraries. Each sub-library has a specific set of primers that can be used to amplify the sub-library using PCR. Once the desired sub-library is amplified, the product is incubated with a nicking enzyme. The enzyme cleaves the phosphodiester bond on the probe strand at its recognition site. Denaturing the resulting product and running it on a denaturing gel allows the desired probe sequence to be released. The probe band can then be cut out of the gel and extracted. The extracted product can be used for hybridization.

In some embodiments, oligonucleotides of provided technologies are generated from oligonucleotide pools. In some embodiments, such pools are available commercially. An initial DNA oligonucleotide pool in some embodiments consists of up to 12,000 or more different single stranded sequences organized into subsets. Each sequence is designed such that nicking endonuclease sites and a forward and reverse primer sequence flank a desired sequence (e.g., a probe sequence). The forward and reverse primer sequences specify to which subset with the desired sequence belongs. The primer pair can be used to amplify the subset using polymerase chain reaction (PCR). The product of the PCR reaction is isolated and digested by the nicking endonucleases. The incubation time with the nicking enzyme varies based on the amount of enzyme used and the amount of DNA recovered. In some embodiments, about 10 units of enzyme digest about 1 μg of DNA in about 1 hour. The sample is then purified and reconstituted in a buffer, e.g., 2× loading buffer (96% formamide/20 mM EDTA) and water to make a final loading buffer (48% formamide/10 mM EDTA), and denatured, e.g., by heating to 95° C. to completely denature the DNA. The denatured DNA is purified and the desired product isolated. In some embodiments, purification and/or isolation comprise electrophoresis. An exemplary process is illustrated in FIG. 25.

In some embodiments, the present invention provides a method for preparing a target nucleic acid having a first sequence, comprising steps of:
1) providing a first nucleic acid comprising the first sequence or its complimentary sequence, wherein the first sequence or its complementary sequence is flanked by at least one restriction site;
2) amplifying the first nucleic acid or part of the first nucleic acid to provide a second nucleic acid comprising the first sequence and the at least one flanking restriction site; and
3) contacting the second nucleic acid with a restriction enzyme corresponding to the at least one flanking restriction site to provide a third nucleic acid comprising a recessed end;
4) contacting the third nucleic acid with a nuclease to selectively digest the strand comprising the complementary sequence, if any, while keeping the strand comprising the first sequence.

In some embodiments, the first sequence or its complementary sequence is independently flanked by a restriction site at each end.

In some embodiments, the present invention provides a method for preparing a target nucleic acid having a first sequence, comprising steps of:
1) providing a first nucleic acid comprising the first sequence or its complimentary sequence, wherein the first sequence or its complementary sequence is flanked by restriction sites at both ends;
2) amplifying the first nucleic acid or part of the first nucleic acid to provide a second nucleic acid comprising the first sequence and the flanking restriction sites; and
3) contacting the second nucleic acid with restriction enzymes corresponding to the flanking restriction sites to provide a third nucleic acid comprising a recessed end;
4) contacting the third nucleic acid with a nuclease to selectively digest the strand comprising the complementary sequence, if any, while keeping the strand comprising the first sequence.

In some embodiments, a target nucleic acid having a first sequence is single-stranded. In some embodiments, an amplifying step comprises PCR. In some embodiments, provided methods further comprise isolating the nucleic acid having a first sequence. In some embodiments, a second nucleic acid is optionally modified before contacting with restriction enzymes. In some embodiments, a third nucleic acid is optionally modified before contacting with a nuclease. In some embodiments, a nuclease is exonuclease III, which preferentially degrade a strand with 3'-recessed ends, and can preserve a strand with a 5' recessed ends. In some embodiments, a restriction enzyme creates a 5'-recessed end. In some embodiments, a restriction enzyme creates a 3'-recessed end. In some embodiments, the complementary sequence has a 3' recessed end after restriction digestion. In some embodiments, the strand comprising the complementary sequence has a 3' recessed end after restriction digestion, and the strand comprising a first sequence has a 5' recessed end after restriction digestion. In some embodiments, provided methods further comprise labeling a nucleic acid having a first sequence.

In some embodiments, single stranded oligonucleotides, e.g., probes for seqFISH or intermediate oligonucleotides, can be generated using nuclease digestion, such as exoIII nuclease digestion. Instead of two nick sites on the amplification (e.g., PCR) products, two restriction sites can be used flanking the probe and/or adaptor sequence. In some embodiments, one restriction site leaves a 3' recessed end while the other leaves a 5' recessed ends. For example, EcoRI and BamHI leave 5' recessed ends, while BmtI and PacI leave 3' recessed ends. Such restriction enzymes are widely known and used in the art. Exonuclease III degrades the 3' recessed ends preferentially, and preserve the strand with the 5' recessed ends. This provides another mechanism to generate single stranded probes from oligonucleotide pools using PCR and restriction nucleases.

In some embodiments, a provided target nucleic acid is DNA. In some embodiments, a target nucleic acid has the same sequence a first sequence. In some embodiments, a target nucleic acid is an intermediate oligonucleotide, comprising a first sequence that hybridizes to a target, e.g., a transcript or a DNA locus, and a second sequence that hybridizes to a second oligonucleotide, e.g., a detectably labeled oligonucleotide. In some embodiments, a target nucleic acid is an intermediate oligonucleotide, comprising a first sequence that hybridizes to a target, and a second sequence that hybridizes with a detectably labeled oligonucleotide labeled by HCR. In some embodiments, a target nucleic acid is a bridge probe.

In some embodiments, provided methods are used for diagnosis of a disease, wherein the disease is related to an abnormal number of a transcript or a DNA locus. In some embodiments, provided methods are used for selecting subjects for a treatment. In some embodiments, provided methods are used for monitoring a treatment regimen. In some embodiments, a cell in provide methods is from a subject. In some embodiments, a cell in provide methods is a mammalian cell. In some embodiments, a cell in provide methods is a human cell. In some embodiments, a cell in provide methods is from a subject. In some embodiments, a cell in provide methods is from an animal. In some embodiments, a cell in provide methods is from a human subject. In some embodiments, a cell in provide methods is isolated from a human subject. In some embodiments, a cell in provide methods is from a diseased tissue, or a tissue that is susceptible to a disease. Being capable of detecting and quantifying a number of targets at the same time, provided methods provides significant advantages for diagnosis, treatment monitoring and patient stratification.

In some embodiments, provided technologies optionally comprises profiling proteins, neural activities, and/or structural arrangements. In some embodiments, provided methods comprise profiling proteins in the same sample. In some embodiments, provided methods comprise profiling neural activities in the same sample. In some embodiments, provided method comprise profiling structural arrangement.

As exemplified herein, provided technologies work for a wide variety of samples. For example, HCR-seqFISH worked in brain slices and that SPIMs can robustly detect single mRNAs in CLARITY brain slices. In some embodiments, provided technologies are useful for profiling targets in mouse models of neurodegenerative diseases, or human brains. No other technology prior to the present invention can deliver the same quality and quantity of data.

Exemplification

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

In Situ Profiling of Nucleic Acids by Sequential Hybridization and Barcoding

Figure 2:
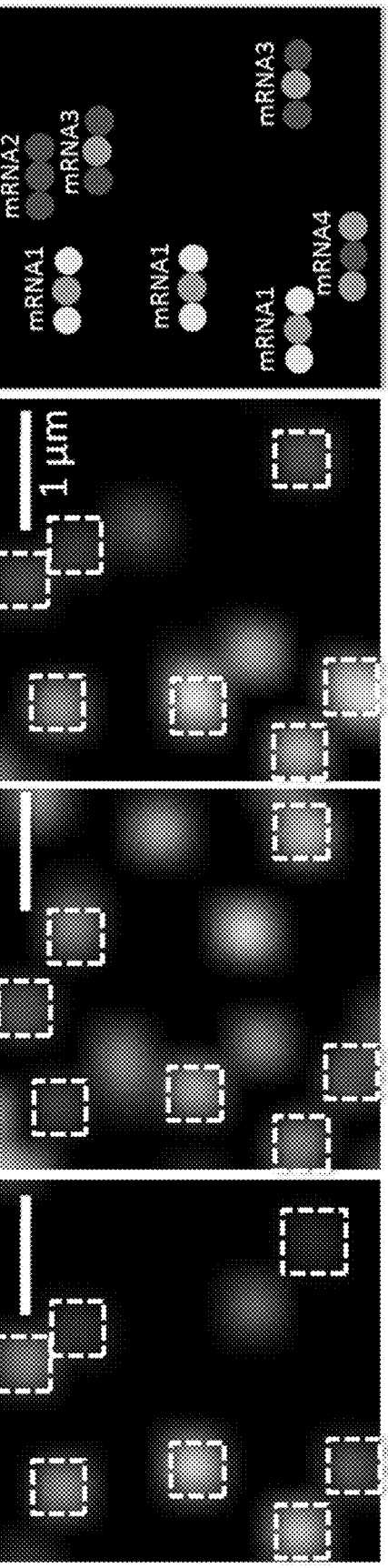
FIG. 2. Exemplary sequential barcoding of provided methods. (a) Schematic of sequential barcoding. In each round of hybridization, multiple probes (e.g., 24) were hybridized on each transcript, imaged and then stripped by DNase I treatment. The same probe sequences could be used in different rounds of hybridization, but probes were coupled to different fluorophores. (b) Composite four-color FISH Data from 3 rounds of hybridizations on multiple yeast cells. Twelve genes were encoded by 2 rounds of hybridization, with the third hybridization using the same probes as hybridization 1. The boxed regions were magnified in the bottom right corner of each image. The matching spots were shown and barcodes were extracted. Spots without co-localization, without the intention to be limited by theory, could be due to nonspecific binding of probes in the cell as well as mis-hybridization. The number of each barcode were quantified to provide the abundances of the corresponding transcripts in single cells. (c) Exemplary barcodes. mRNA 1: Yellow-Blue-Yellow; mRNA 2: Green-Purple-Green; mRNA 3: Purple-Blue-Purple; and mRNA 4: Blue-Purple-Blue.

As described in the non-limiting examples herein, nucleic acids in cells, for example, mRNAs, were profiled by provided methods through sequential rounds of contacting, imaging and removing steps (FIGS. 2 (*a*) and 3). As the transcripts are fixed in cells, the corresponding fluorescent spots remain in place during multiple rounds of hybridization, and can be aligned to read out a fluorophore sequence. This sequential barcode is designed to uniquely identify an mRNA.

During each round of hybridization, each transcript was targeted by a set of detectably labeled oligonucleotides, in this case, FISH probes labeled with a single type of fluorophore. The sample was imaged and then treated it with DNase I to remove the FISH probes. In a subsequent round the mRNA was hybridized with FISH probes with the same set of oligonucleotide sequences, but now labeled with a different dye. The number of barcodes available scales as $F^N$, where F is the number of fluorophores and N is the number of hybridization rounds. For example, with 4 dyes, 8 rounds of hybridization can cover almost the entire transcriptome ($4^8=65,536$).

Figure 4:
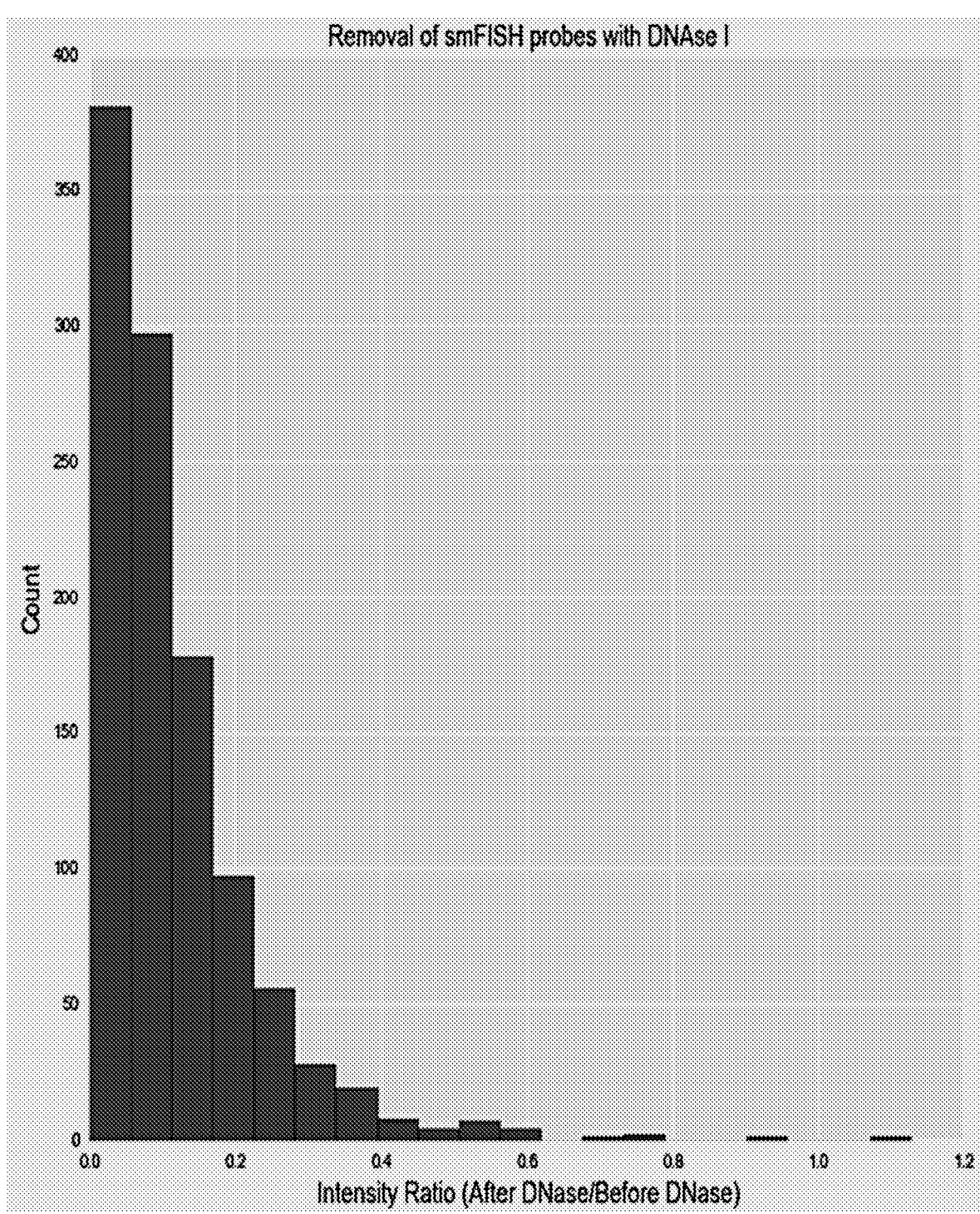
FIG. 4. DNase I efficiently removes smFISH probes bound to mRNA. DNase I efficiently removes smFISH probes bound to mRNA. Spots were imaged before and after a 4 hour DNase I treatment in anti-bleaching buffer. The mean, median and STD of the intensity ratio after treatment were 11.5%, 8.3% and 11%. The ratio of the spot intensities after and before DNase I treatment was plotted for each spot. n=1084 spots.
Figure 5:
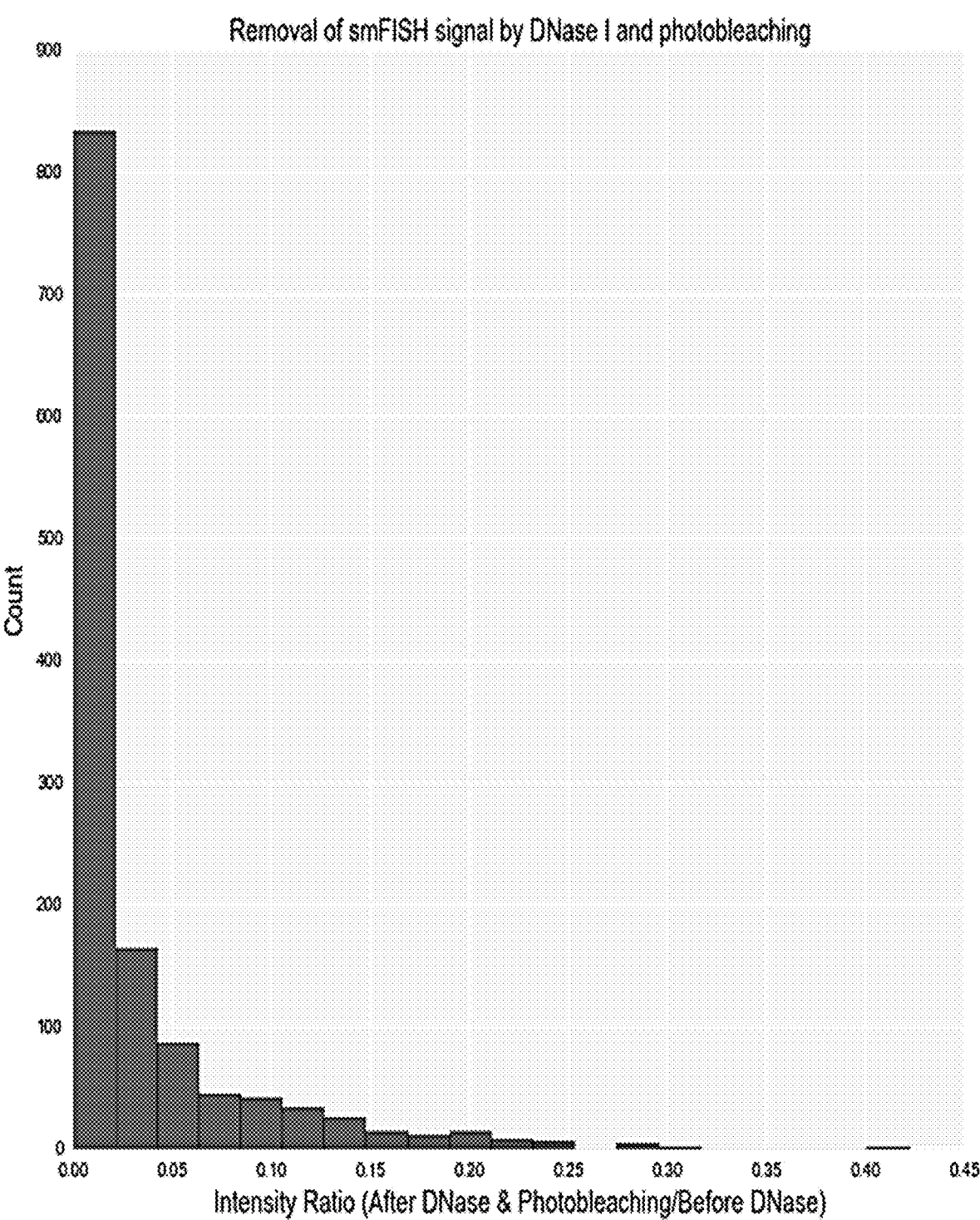
FIG. 5. Photobleaching removes residual intensity following DNase I treatment. Photobleaching removed residual intensity following DNase I treatment. Spots were bleached by 10 seconds of excitation following a 4 hour DNase I treatment. The mean, median and STD of the intensity ratio after bleaching were 0.03%, 0.01% and 0.049%. The ratio of the spot intensities after and before DNase I treatment was plotted for each spot. n=1286 spots.
Figure 6:
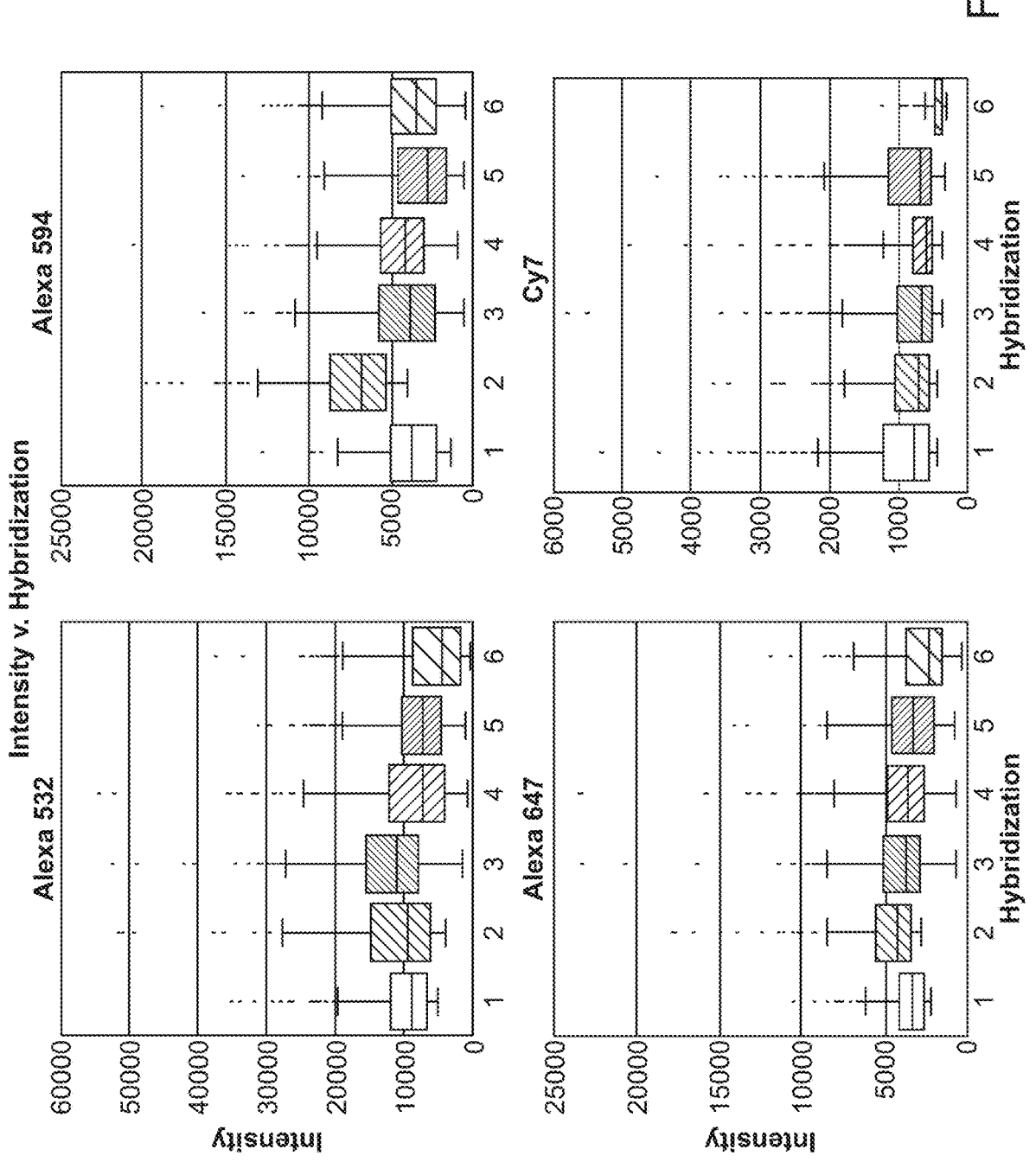
FIG. 6. mRNAs are stable over multiple rounds of re-hybridization. mRNAs were stable over multiple rounds of re-hybridization. The intensity distributions of smFISH spots were plotted over 6 hybridizations. Two hybridizations were repeated 3 times to make 6 total hybridizations. Spots were identified by their co-localization with spots in the next identical hybridization. For each boxplot the number of spots counted was between 191 and 1337.
Figure 7:
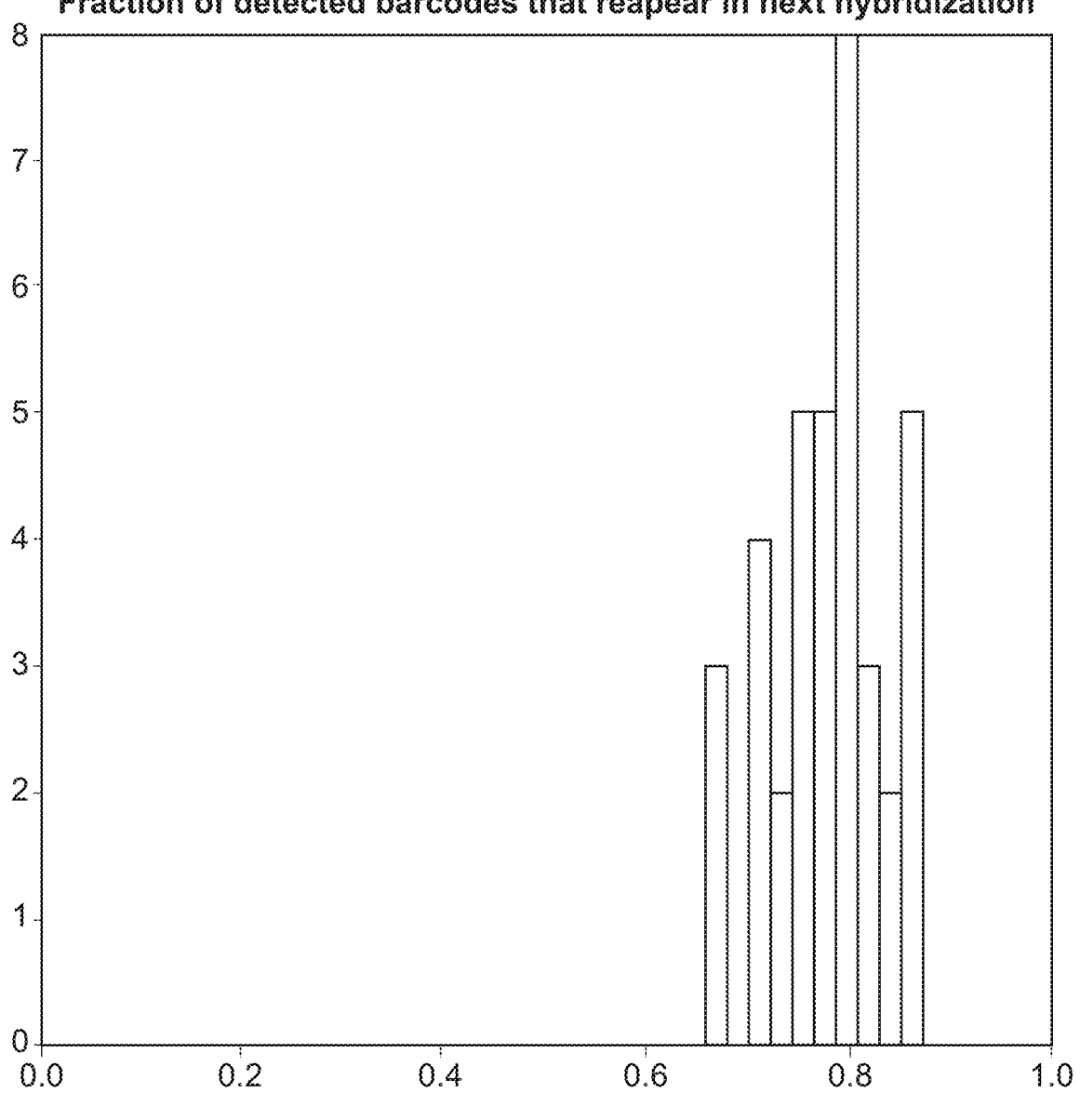
FIG. 7. Fraction of barcodes identified from first two rounds of hybridization that reoccur in following round of hybridization per cell. Fraction of barcodes identified from first two rounds of hybridization that reoccur in following round of hybridization per cell. Barcodes were identified by co-localization through all three hybridizations. 77.9±5.6% of barcodes reoccur. n=37 cells.
Figure 8:
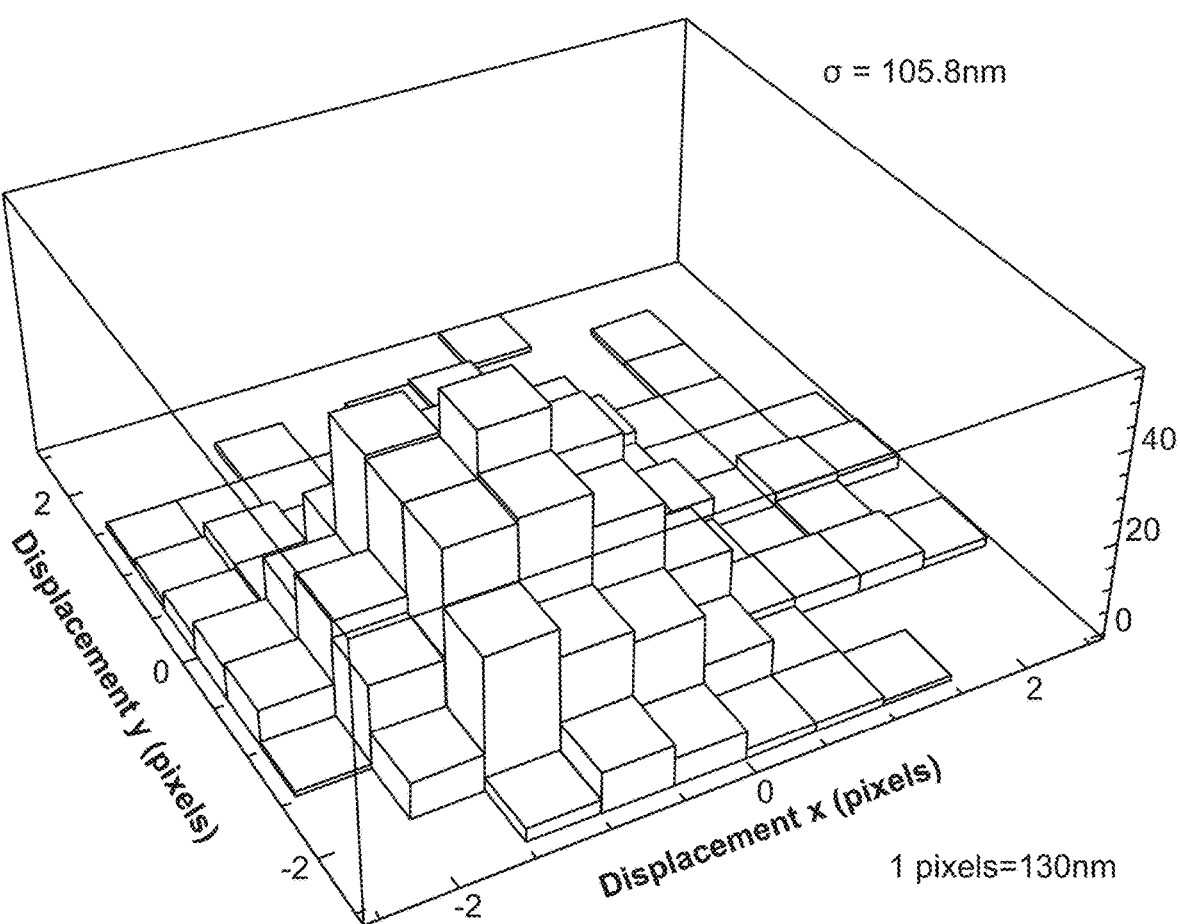
FIG. 8. Point-wise displacement between FISH points in Hybridizations 1 and 3. Point-wise displacement between FISH points in Hybridizations 1 and 3. FISH dots in the Cy5 images in Hybridization 1 and 3 were extracted, fitted with 2D Gaussians. The point-wise displacements were shown in the 3D histogram. The standard deviation was 105.8 nm, indicating that mRNAs can be localized to 100 nm between 2 rounds of hybridizations. n=1199 spots.
Figure 9:
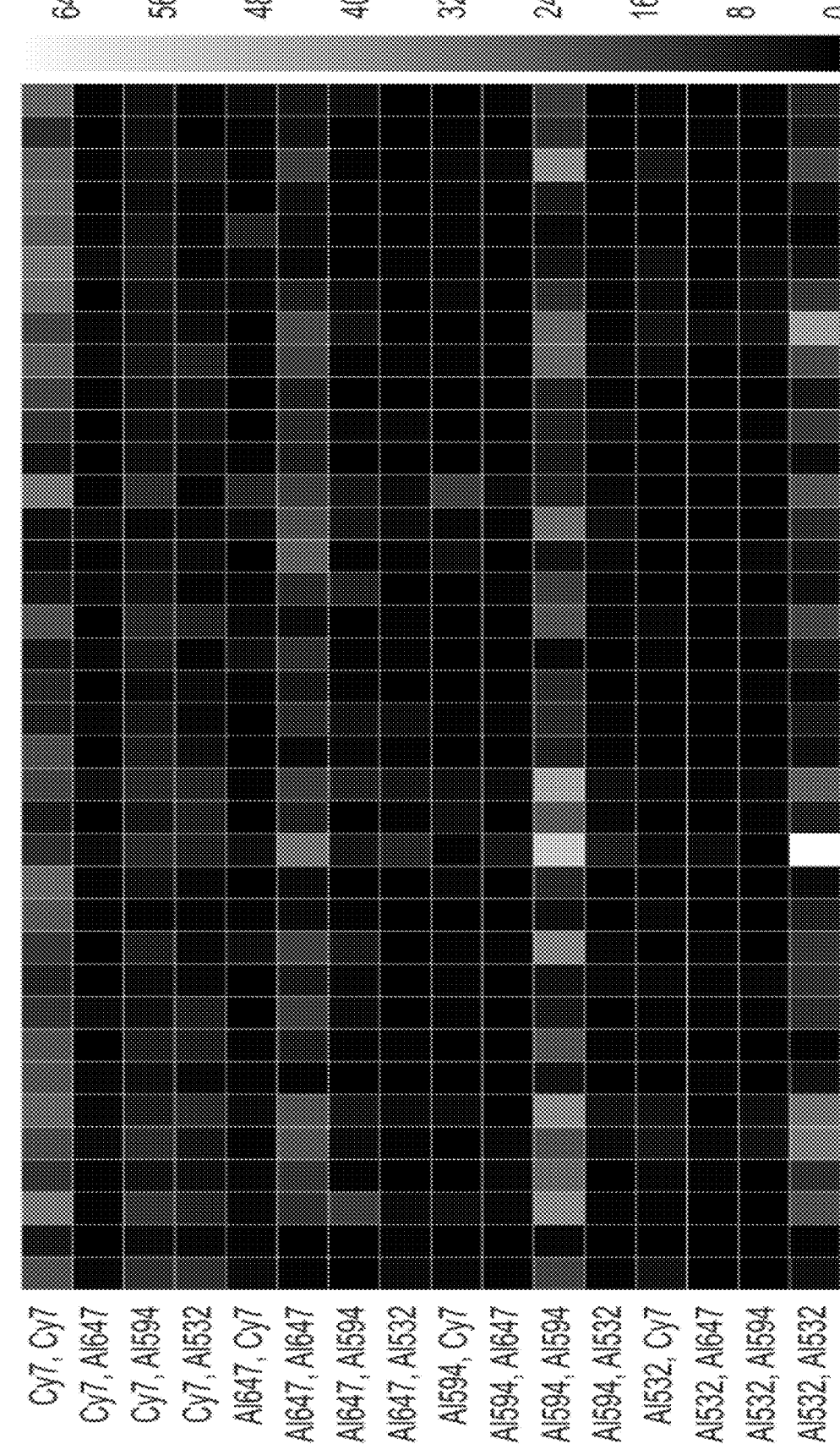
FIG. 9. Barcodes identified between repeat hybridizations of the same probe set (hybridization 1 and 3). Barcodes identified between repeat hybridizations of the same probe set (hybridization 1 and 3). Barcodes were identified by co-localization between the hybridizations. Each column corresponds to an individual cell. Each row corresponds to a specific barcode identified between hybridization 1 and 3. Bolded row names correspond to repeated color barcodes that should co-localize between hybridization 1 and 3. Non-bolded row names correspond to false positive barcodes. For example, a large number of barcodes were detected for (Alexa 532, Alexa 532), indicating co-localization of spots in the Alexa 532 channels. n=37 cells. Al532=Alexa 532. Al594=Alexa 594. Al647=Alexa 647.
Figure 10:
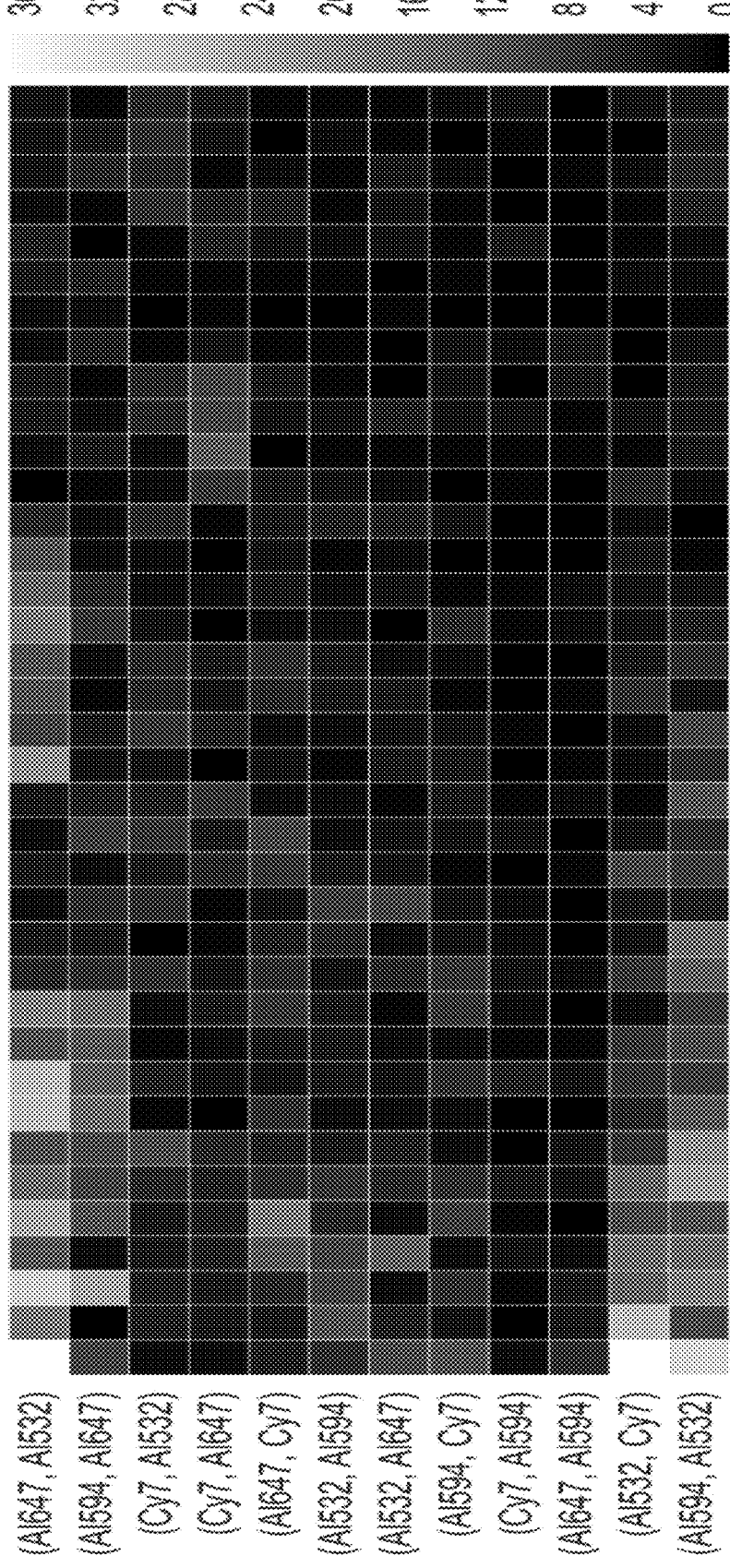
FIG. 10. Single cell mRNA levels from barcode extraction. Single cell mRNA levels from barcode extraction. Barcodes were identified by co-localization between hybridizations 1 and 2. Each column corresponds to an individual cell. n=37 cells. Al532=Alexa 532. Al594=Alexa 594. Al647=Alexa 647. From top to bottom: YLR194c, CMK2, GYP7, PMC1, NPT1, SOK2, UIP3, RCN2, DOA1, HSP30, PUN1 and YPS1.
Figure 11:
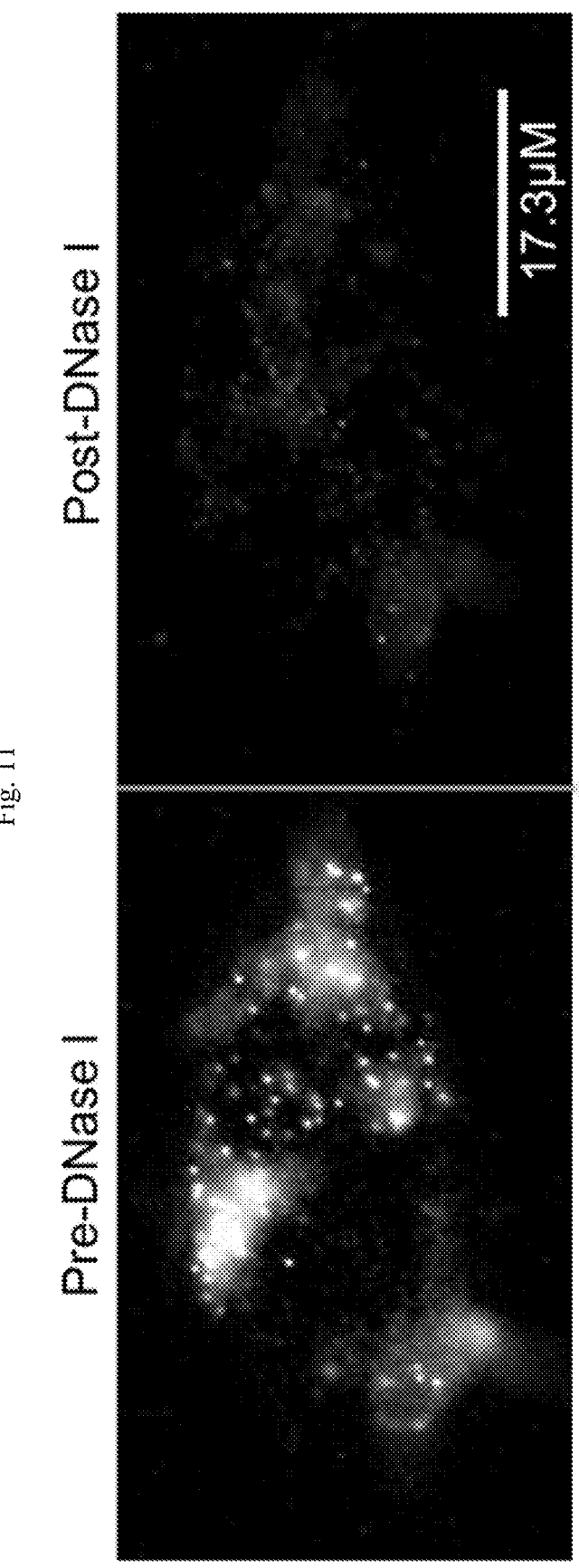
FIG. 11. DNase I stripping of Nanog Alexa 647 probes in mouse embryonic stem cells (mESCs). DNase I stripping of Nanog Alexa 647 probes in mouse embryonic stem cells (mESCs). Forty-eight probes targeting Nanog were hybridized in mESCs. Probes were stripped off by 30 minutes of DNase I incubation at a concentration of 3 Units/µL.
Figure 12:
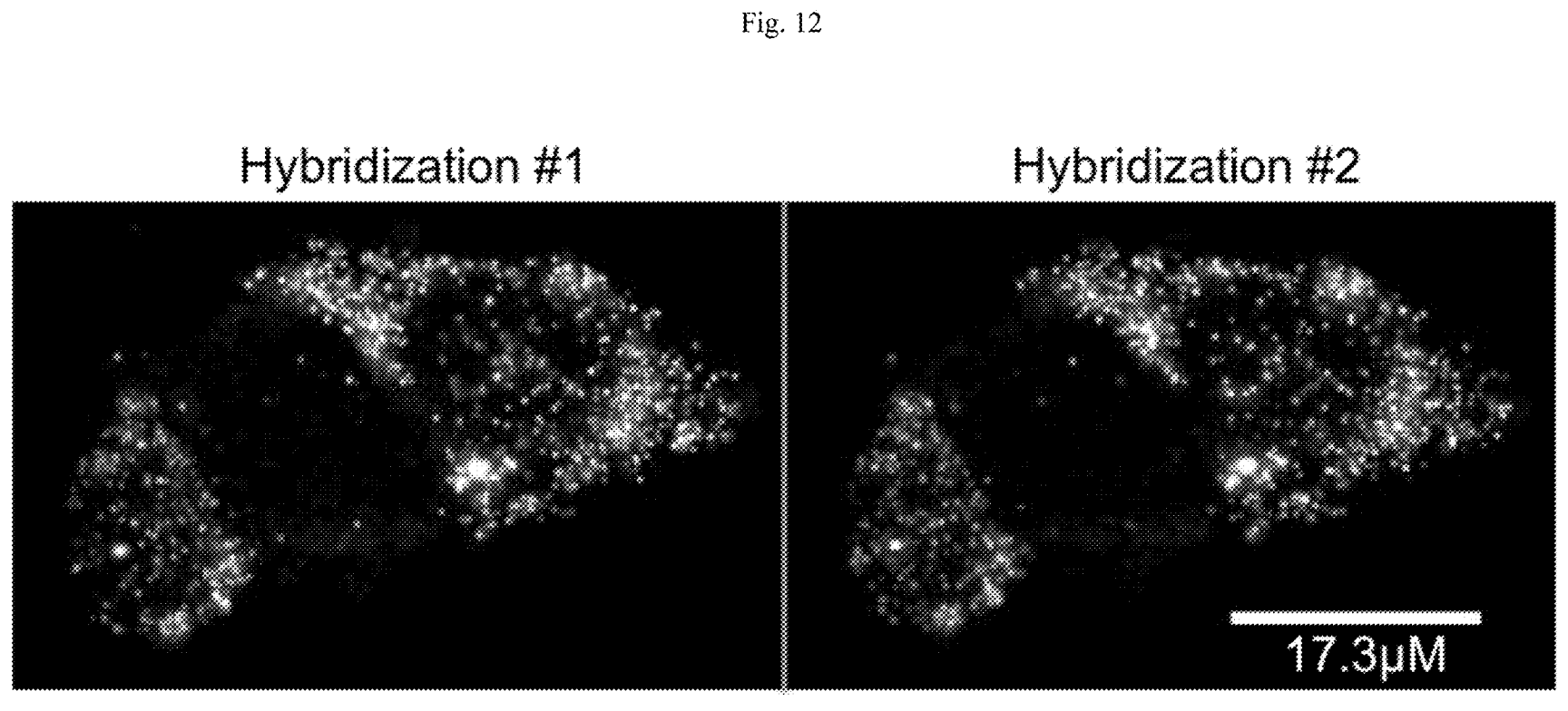

As a demonstration, 12 genes were barcoded in single yeast cells with 4 dyes and 2 rounds of hybridization ($4^2=16$, with 4 barcodes left out; each hybridization was conducted for 3 cycles). Cells were immobilized on glass surfaces. The DNA probes were hybridized, imaged, and then removed by DNase I treatment ($88.5\pm11.0\%$ (SE) efficiency, FIG. 4). The remaining signal was photobleached (FIG. 5). Even after 6 hybridizations, mRNAs were observed at $70.9\pm21.8\%$ (SE) of the original intensity (FIG. 6). It was observed that $77.9\pm5.6\%$ (SE) of the spots that co-localized in the first two hybridizations also co-localize with the third hybridization (FIGS. 7 and 8). The mRNA abundances were quantified by counting the occurrence of corresponding barcodes in the cell (FIGS. 9 and 10, n=37 cells). It was shown that mRNAs can be stripped and re-hybridized efficiently in mammalian cells (FIGS. 11 and 12). As demonstrated here, provided methods have many advantages over methods known prior to the present invention. For example, provided methods scale up quickly; with even two dyes the coding capacity is in principle unlimited ($2^N$). During each contacting step, all available detectably labeled oligonucleotides, in this example, FISH probes, against a target can be used, increasing the brightness of the signals. Readouts of provided methods are also robust and enable full Z-stacks on native samples. Provided methods can take advantage of the high hybridization efficiency of detectably labeled oligonucleotides, such as FISH probes (>95% of the mRNAs are detected; Lubeck, E. & Cai, L. *Nat. Methods* 9, 743-48 (2012)). Applicant notes that detectably labeled oligonucleotides, for example FISH probes, can also be designed to resolve a large number of splice-isoforms, SNPs, as well as chromosome loci (Levesque, M. J. & Raj, A. *Nat Meth* 10, 246-248 (2013)) in single cells. In combination with super-resolution methods (Lubeck, E. & Cai, L. *Nat. Methods* 9, 743-48 (2012)), provided methods enable a large number of targets, for example the transcriptome, to be directly imaged at single cell resolution in complex samples, such as the brain.

Methods and Procedures

Sample Preparation: MDN1-GFP yeast cells were grown in YPD supplemented with 50 mM $CaCL_2$ to OD 0.3. Cells were fixed in 1% Formaldehyde 5% Acetic Acid for 5 minutes, rinsed 3x in Buffer B and spheroplasted for 1 hour at 30° C. Cells were stored in 70% EtOH at −20° C. for up to two weeks.

Coverslips were prepared by sonicating 3x with alternating solutions of 1M NaOH and 100% EtOH followed by a final round of sonication in acetone. A 2% solution of (3-Aminopropyl) triethoxysilane (Sigma 440140) was prepared in acetone and the cleaned coverslips were immediately submerged in it for two minutes. Amine-modified coverslips were rinsed and stored in ultra-pure water at room temperature.

Fixed yeast cells were pre-treated with a 0.5 U/μL solution of DNase I (Roche 04716728001) for 30 minutes at 23° C. Following treatment, yeast cells were adhered to coated coverslips by physically compressing a dilute solution of yeast between two amine-modified coverslips. The coverslips were then carefully pealed apart and immediately submerged in a 1% formaldehyde solution for 2.5 minutes. Following fixation coverslips were dried and a flow cell was constructed by adhering an adhesive coated flow cell to the coverslip (GraceBio Labs SA84-0.5-SecureSeal). Fluo-Sphere 365 nm fluorescent beads were added to the coverslip to measure drift over multiple hybridizations (Life F8805). Flow cells were stored at 4° C. covered with parafilm.

Preparation of Detectably Labeled Oligonucleotides: Probes were prepared according to the method in Lubeck, E. & Cai, L. *Nat. Methods* 9, 743-48 (2012). For each target, 24 probes were used. All 24 probes for each set of genes were coupled to one of the four dyes used, Alexa 532, 594, Cy5 and Cy7.

Hybridization: Flow cells were hybridized at a concentration of 2 nM/probe overnight in a hybridization buffer of 10% Dextran Sulfate (Sigma D8906), 10% formamide, and 2×SSC. Following hybridization, samples were washed in a 30% formamide, 0.1% Triton-X 100 buffer pre-heated to 37° C. before adding to room temperature samples for 10 minutes. Samples were washed several times with 2×SSC to remove diffusing probes.

Imaging: Samples were immersed in an anti-bleaching buffer (Swoboda, M. *ACS Nano* 6, 6364-69 (2012)): 20 mM Tris-HCL, 50 mM NaCl, 0.8% glucose, saturated Trolox (Sigma: 53188-07-1), pyranose oxidase (Sigma P4234) at an $OD_{405\ nm}$ of 0.05, and catalase at a dilution of 1/1000 (Sigma: 9001-05-2).

Probe Displacement: Following imaging, cells were washed in DNase I buffer (Roche) and allowed to sit in 0.5 U/μL DNase I (Roche) for 4 hours. To inhibit DNase cells were washed 2× with 30% formamide, 0.1% Trition-X 100, 2×SSC. Following DNase treatment cells were imaged once more in anti-bleaching buffer to determine DNase I probe stripping rates. To remove remaining probe signal, samples were bleached with 10 seconds of excitation in all imaging channels and imaged once more with standard excitation times to record residual signal.

Re-hybridization: Samples were re-hybridized on the microscope according to the previously outlined conditions. Samples were covered with parafilm during hybridization on the scope to prevent evaporation.

At least six rounds of hybridizations were carried out on the same sample. Each round of hybridization took place overnight on the microscope, with DNase treatment and imaging occurring during the day. In the iterative hybridization scheme applied in this correspondence, two rounds of hybridization were used to barcode the mRNAs. The barcode scheme was then repeated, such that hyb1 and hyb3 were performed using the same probes, while hyb2 and hyb4 were done with another set of probes. The co-localization between hyb1 and hyb3 gave a calibration for transcripts that were detected, while hyb1 and hyb2 yielded the barcoding data.

Data Analysis: Data analysis was carried out with ImageJ, Python and Matlab. Since the sample drifted during the experiments, the raw images were aligned using cross-correlation based registration method that was determined from the DAPI channel of each imaging position. The drift-correction was then propagated to the other 4 color channels corresponding to the same position. The images were then deconvolved to decrease the overlap between adjacent FISH spots. Spots overlaps in individual channels were rarely observed, but spots in different channels could overlap in their point spread functions (PSFs) when the images were overlaid. The raw data were processed based on an iterative Lucy-Richardson algorithm (Lucy, L. B. *The Astronomical Journal.* 79, 745 (1974) and Richardson, W. H. *J. Opt. Soc. Am.* 62, 55-59 (1972)). The PSF of the microscope was estimated by averaging the measured bead images (~200 nm diameter) in the DAPI channel of the microscope. Using this measured point spread function with the Lucy-Richardson algorithm, we performed maximum-likelihood estimation of fluorescent emitter distribution in the FISH images after computing this process over ~20 iterations. The output of this deconvolution method provides resolved FISH data and increases the barcode assignment fidelity.

Dots corresponding to FISH signals in the images were identified using a local maximum function. Dots below a threshold were discarded for further analysis. The value of the threshold was determined by optimizing the co-localization between hyb1 and hyb3 images, which were hybridized with the same probe sets. The maximum intensity pixel for each PSF was used as a proxy for the location of that mRNA molecule.

The barcodes were extracted automatically from the dots corresponding to mRNAs in hyb1 and hyb2. The algorithm calculated the pairwise distances between each point identified in hyb1 with all the points identified in hyb2. For each point in hyb1, the closest neighbor in hyb2 was identified. If that distance were 0 or 1 pixel and the closest neighbor of the point in hyb2 were also the original point in hyb1, then the barcode pair was confirmed. The symmetrical nearest neighbor requirements decreased the false assignment of barcodes. To reduce false positives in cy7, points detected in hyb1 cy7 were required to reappear in hyb3 in cy7.

In this non-limiting example, Applicant removed probes with DNase I due to its low cost and rapid activity. Applicant notes that any method that removes probes from mRNA and leaves it intact could be used in provided barcoding approaches, for example but not limited to, strand-displacement (Duose, D. Y. *Nucleic Acids Research,* 40, 3289-3298 (2012)) and high temperature or formamide washes. Applicant notes that DNase I does not require probe redesigns from standard smFISH probes, and does not perturb the sample with harsh washes.

In some embodiments, a rapid loss of DAPI signal from dsDNA within seconds was observed, while smFISH probes took a substantially longer period of time (10s of minutes) to be degraded. Without the intention to be limited by theory, the efficiency of DNase I probe removal could be low relative to the dsDNA cleavage rate. The removal process was still observed in a short amount of time.

In certain experiments, 11.5% of the fluorescent signal remained on mRNA after DNase I treatment. The remaining signal was reduced almost to zero by bleaching. Applicant notes that more complete removal of signal and/or probes can be achieved prior to photobleaching, so that more mRNAs are available for the following rounds of hybridization. Applicant notes that photobleaching is not necessary for barcoding, but in some embodiments, it does simplify the process by removing residual signal that might give false positives in further rounds of barcoding. Some of the 11.5% of residual probes bound to mRNA may inhibit further rounds of hybridization. Applicant notes that residual probes were not significantly inhibiting progressive rounds of hybridization as presented data showed a minor drop in hybridization efficiency for 5 hybridizations.

Profiling of Nucleic Acids in Brain Tissues

Transcription profiling of cells in intact brain slices are essential for understanding the molecular basis of cell identity. However, prior to the present invention it was technically difficult to quantitatively profile transcript abundance and localization in single cells in the anatomical context of native neural networks. The cortical somatic sensory sub-networks are used as an example to demonstrate the feasibility and utility of exemplary provided technologies, for example, using in situ sequencing by FISH (seqFISH) and connectomics to profile multiple genes in distinct neuronal populations within different functional domains, such as those in the primary somatic sensory (SSp), primary somato-motor (MOp), secondary somatomotor (MOs), and supplementary somatosensory (SSs) cortical areas.

As described extensively herein, in some embodiments, the present invention provides technologies to profile gene expression in single cells via in situ "sequencing" by FISH, e.g., as illustrated by FIGS. 1 and 2. To detect individual mRNAs, single molecule fluorescence in situ hybridization (smFISH) was used with 20mer oligonucleotide probes complementary to the mRNA sequence (Fan, Y., Braut, S A, Lin, Q., Singer, R H, Skoultchi, A I. Determination of transgenic loci by expression FISH. Genomics. 2001 Oct. 2; 71(1): 66-9; Raj A, Peskin C S, Tranchina D, Vargas D Y, Tyagi S. Stochastic mRNA synthesis in mammalian cells. PLoS Biol. 2006 October; 4(10):e309). By putting 24 such fluorophore labeled probes on an mRNA, single transcripts in cells become readily detectable in situ. It was shown that almost all mRNAs that can be detected are observed by smFISH (Lubeck, E. L. Cai. Single cell systems biology by super-resolution imaging and combinatorial labeling. Nature Methods 9, 743-48 (2012)). Provided methods are highly quantitative and preserve the spatial information within a tissue sample without physically isolating single cells or using homogenates.

Figure 3:
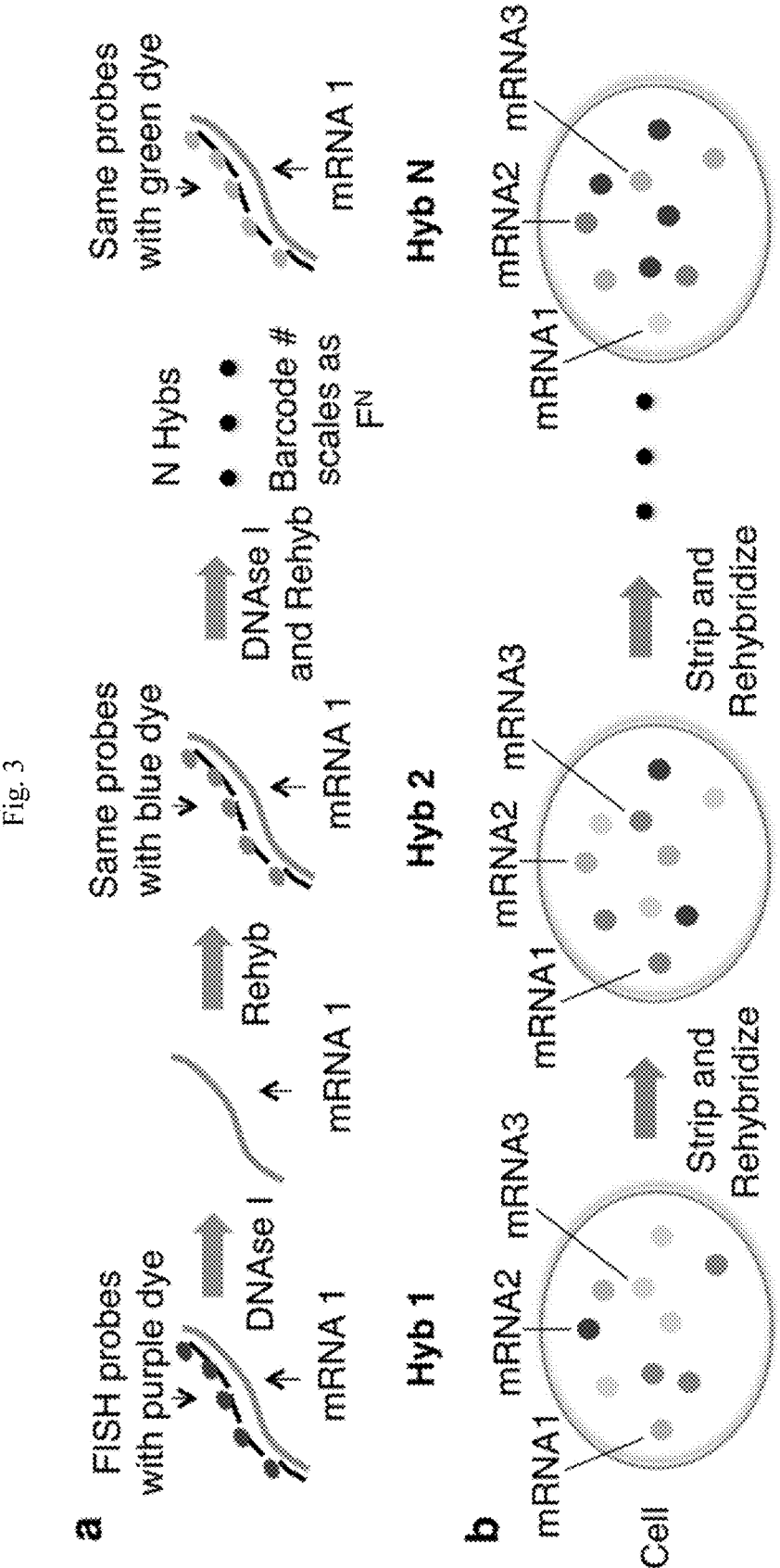
FIG. 3. Schematic of sequential hybridization and barcoding. (a) Schematic of sequential hybridization and barcoding. (b) Schematic of the FISH images of the cell. In each round of hybridization, the same spots were detected, but the dye associated with the transcript changes. The identity of an mRNA was encoded in the temporal sequence of dyes hybridized.

In some embodiments, to distinguish different mRNA species, mRNAs are barcoded with detectably labeled oligonucleotides, such as FISH probes using sequential rounds of hybridization. During a round of hybridization, each transcript is targeted by a set of multiple, for example, 24 FISH probes, labeled with a single type of fluorophore. The sample is imaged and the FISH probes are removed by enzymatic digestion. Then the mRNA is hybridized in a subsequent round with the same FISH probes, but now labeled with, in some cases, a different dye. As the transcripts are fixed in cells, the fluorescent spots corresponding to single mRNAs remain in place during multiple rounds of hybridization, and can be aligned to read out a color sequence. Each mRNA species is therefore assigned a unique barcode. The number of each transcript in a given cell can be determined by counting the number of the corresponding barcode. An exemplary process is illustrated in FIG. 1, 2, or 3.

Provided technologies can take advantage of the high hybridization efficiency of FISH (>95% of the mRNAs are detected). In some embodiments, base pair resolution is not needed to identify a transcript, although can be achieved if desired. The number of barcodes available with provided methods scales as $F^N$, where F is the number of distinct fluorophores and N is the number of hybridization rounds. With 5 distinct dyes and 3 rounds of hybridization, 125 unique nucleic acids can be profiled. Almost the entire transcriptome can be covered by 6 rounds of hybridization ($5^6=15,625$), for example, using super-resolution microscopy which resolves all of the transcripts in a cell. In some embodiments, conventional microscopy, such as conventional epi-fluorescence microscopy which is simple and robust to implement, is used to detect fewer but still large number of targets, for example, at 100 genes multiplex.

Probes can be stripped and rehybridized to the same mRNA in multiple cycles of hybridization (FIG. 2). Many commercially available fluorophores work robustly, such as Alexafluor 488, 532, 594, 647, 700, 750, and 790, giving at least 7 colors for barcoding. Even at the end of 6 rounds of hybridizations, probes can be re-hybridized to the stripped mRNA with 70.9±21.8% (FIG. 6) of the original intensity. As a demonstration, barcoded 12 genes were barcoded in single yeast cells with 4 dyes and 2 rounds of hybridization ($4^2=16$, FIG. 3, c).

There is sufficient optical space in cells to perform multiple, e.g., 100 gene multiplex, as 12 genes multiplex images only occupied 5% of the optical space in each fluorescent channel. Although the composite image of all 4 fluorescent channels in FIG. 3 appears dense, spots in each fluorescent channel are sparsely distributed. Each spot can be fitted with a 2 dimensional Gaussian profile to extract its centroid positions and further reduce the overlaps with spots in other fluorescent channels. It was shown that the same spots realign to 100 nm between different rounds of hybridization (FIG. 8).

In some embodiments, a 100 genes multiplex can be performed quickly with 3 rounds of hybridization. In some embodiments, each hybridization cycle involves about 4 hours of hybridization, about 1 hour of imaging and about 1 hour of DNase treatment and washing, the time length of each can be optionally and independently varied. In some embodiments, 3 rounds of hybridization take approximately 18 hours. In some embodiments, imaging time is the rate limiting step, rather than the hybridization time, because one brain slice can be imaged while another slice on the same microscope is hybridizing. In some embodiments, a single microscope can multiplex up to 8 slices simultaneously and obtain 100 gene data on all 8 slices at the end of the 3 cycles of hybridization in 18 hours.

In some embodiments, a 10 mm×5 mm×10 μm brain slice containing $10^6$ cells can be imaged and analyzed in 35 minutes on microscopes. In some embodiments, a single field of view (FOV) on a microscope is 0.5 mm×0.5 mm×2 μm with a 20× air objective and 13 mm×13 mm camera chip. In some embodiments, each FOV is exposed and read out in 100 msec. In some embodiments, scanning the sample in xyz and in the different color channels introduces a time delay of 200 msec between snapshots. In some embodiments, an entire brain slice can be imaged in 2000 sec or 35 minutes. With 3 rounds of hybridization needed for the 100 gene multiple, the total imaging time is 105 minutes. In some embodiments, an entire mouse brain can be imaged in 30 days on one microscope. When multiple microscope is used, the time frame can be further shortened. In some embodiments, provided methods can image an entire mouse brain with 500 slices with a cost less than $25,000.

Compared with other methods known prior to the present invention, provided technologies provide a variety of advantages. Among other things, provided technologies is quantitative, preserve spatial information and inexpensively scales up to a whole tissue, organ and/or organism.

Comparison with single cell RNA-seq prior to the present invention. Unlike single cell RNA-seq or qPCR, which require single cells to be isolated and put into a 96 well format, provided methods, such as seqFISH, can scan a large number of cells in their native anatomical context with automated microscopy at little additional cost. To achieve the same level of throughput with a microfluidics device would be economically impossible and labor intensive. In some embodiments, major cost of provided technologies is the initial cost of probe synthesis, which is offset by the fact that once probes are synthesized, they can be used in many, e.g., 1000 to 10,000 or even more reactions.

Provided methods such as seqFISH are based on single molecule FISH and can measure low copy number transcripts with absolute quantitation. The data obtained with this method is highly quantitative and enables high quality statistical analysis. In comparison, current single cell qPCR and RNA-seq experiments are limited in quantitative powers with biases from reverse transcription (RT) and PCR amplification errors.

Comparison with other in situ sequencing method prior to the present invention. One major advantage of the smFISH approach is that almost all mRNAs that are targeted can be observed. It was determined that the efficiency of each FISH probes binding on a mRNA is 50-60% (Lubeck, E. & Cai, L. *Nat. Methods* 9, 743-48 (2012); Levesque, M. J. & Raj, A. *Nat Meth* 10, 246-248 (2013)). Targeting multiple, e.g., 24-48 probes per mRNAs ensures that at least 10 probes are hybridized on almost every mRNA, providing good signals over the non-specific background. Directly probing the mRNA with FISH probes is highly specific and ensures that all transcripts are detected.

In contrast, many other in situ sequencing methods, instead of targeting the mRNA directly, use enzymatic reactions to convert the mRNA into a DNA template first, before detecting the DNA template by sequencing reactions. However, the mRNA to DNA conversion process is highly inefficient, and only a small fraction of the RNAs are converted and detected. One exemplary major downside of low efficiency, which is estimated at 1% for reverse transcription (RT) and 10% for padlock ligation (PLA), is that it can introduce significant noise and bias in the gene expression measurements.

Given the typical cell size of (10-20 $\mu m^3$), there are approximately 25,000 diffraction limited spots in the cell. In some embodiments, this is the available real estate for transcript detection in single cells. In seqFISH, a chosen set of genes, such as transcription factors (TFs) and cell adhesion molecules (CAMs), can be imaged and quantitated with high accuracy. If target genes with average copy numbers of 100 transcripts per gene are chosen, a highly quantitative 100-200 gene profiling experiment can be performed. In contrast, with many other in situ sequencing methods, most of that real estate is used to sequence ribosomal RNAs as well as house-keeping genes; genes of interest, such as those specific for neuronal cell identity, are severely under-represented and poorly detected.

In some embodiments, provided methods use hybridization chain reaction (HCR) (Choi, et al., Programmable in situ amplification for multiplexed imaging of mRNA expression *Nature Biotechnol,* 28, 1208-1212, (2010)) to amplify FISH signal that allows large FOV imaging with 20× air objectives, but at the same time preserves the high detection efficiency of smFISH.

Comparison with super-resolution barcoding method of multiplexing RNA prior to the present invention. In some embodiments, provided methods have many advantages compared to spectral barcoding of mRNAs by smFISH prior to the present invention (Femino et al., Visualization of single RNA transcripts in situ. Science. 1998 Apr. 24; 280(5363):585-90; Kosman et al., Multiplex detection of RNA expression in *Drosophila* embryos. Science. 2004 Aug. 6; 305(5685):846; Levsky et al., Single-cell gene expression profiling. Science. 2002 Aug. 2; 297(5582):836-40; Lubeck et al., Single cell systems biology by super-resolution imaging and combinatorial labeling. Nature Methods 9, 743-48 (2012); and Levesque et al., Nat Meth 10, 246-248 (2013)), in which the probes against a particular mRNA are split up into subsets which are labeled with different dyes. Among other things, provided technologies do not require many distinct fluorophores to scale up; with even two dyes, the coding capacity is huge, and repeated barcodes can be used (e.g., Red-Red-Red). In comparison, spectral barcoding of RNA prior to the present invention is limited in the number of barcodes that can be generated (~30). In provided methods, during each round of hybridization, all the detectably labeled oligonucleotides such as FISH probes against a transcript can be used at once instead of splitting probes into subsets. Among other things, provided technologies provide improved robustness of barcode readout, as the signal on each mRNA is stronger. Compared to methods prior to the present invention, density of objects in the image is lower as each mRNA can have fewer colors, in some embodiments, a single color, during each round of hybridization instead of at least 3 colors in the spectral barcoding schemes prior to the present invention. If desirable, the lower image density can greatly simplifies data analysis and allows more genes to be multiplexed before super-resolution microscopy is necessary. Applicant notes that certain spectral barcoding methods, probes, and/or super-resolution microscopy, can be used, and can be useful embodiments, in provided embodiments. To profile the transcriptome with provided technologies such as seqFISH, in some embodiments, super-resolution microscopy is used to resolve the millions of transcripts in the cells.

Besides transcriptional profiling, provided technologies can resolve multiple alternative splicing choices and RNA editing on the same mRNA molecule. Alternative spliced isoforms are difficult to probe by sequencing methods as the sequencing reads are usually too short to correlate the exon choices within the same transcript. Provided methods such as seqFISH allow direct visualization of the entire repertoire of splice isoforms within individual cells in brain slices. Similarly, smFISH methods of detecting single nucleotide polymorphisms (SNPs) can be adapted to seqFISH to image edited transcripts in neurons or other cell types.

In some embodiments, provided technologies provide efficient and cost effective pipelines for gene profiling in situ by sequential FISH (seqFISH), and integrate seqFISH and connectomics to profile somatic motor neurons in the cortex to identify combinatorial molecular markers that correspond to cell identity.

Quantitative In Situ Gene Expression Mapping in Brain

Light sheet microscopy is applied to directly image CLARITY cleared brains slices. In some embodiments, a mouse brain is mapped in 1 month per machine. In some embodiments, a mouse brain is mapped in one week with 4-5 machines.

Amplification: Amplification of FISH signals allows large FOV imaging of brain slices with 20× low NA objectives. In some embodiments, provided methods use detectably labeled oligonucleotides labeled with hybridization chain reaction (HCR) (Choi et al., 2010) to increase the signal-to-background and/or preserve the specificity and multiplexing capabilities of FISH methods. With this approach, nucleic acid probes complementary to mRNA targets trigger chain reactions in which metastable fluorophore-labeled nucleic acid hairpins self-assemble into tethered fluorescent amplification polymers. Using orthogonal HCR amplifiers carrying spectrally distinct fluorophores, in situ amplification can be performed simultaneously for all channels.

In some embodiments, detectably labeled oligonucleotides with HCR (HCR probes) contain a 20-nt domain complementary to the target mRNA plus a 40-nt HCR initiator. The hybridization of probes is performed under stringency of 10% formamide followed by the amplification step at a permissive condition. Conditions like concentration of hairpins can be optimized to achieve optimal results; Applicant notes that, in certain cases, higher concentrations of hairpins increase reaction rate. Every HCR probe can be amplified to a diffraction-limited spot. In some embodiments, FISH signal is amplified by approximately 10-20 times within a diffraction-limited spot size. Spot brightness can be further enhanced while maintaining a diffraction-limited spot size by, for example, incorporating multiple HCR initiators within each probe and/or labeling each HCR amplification hairpin with multiple fluorophores.

Figure 13:
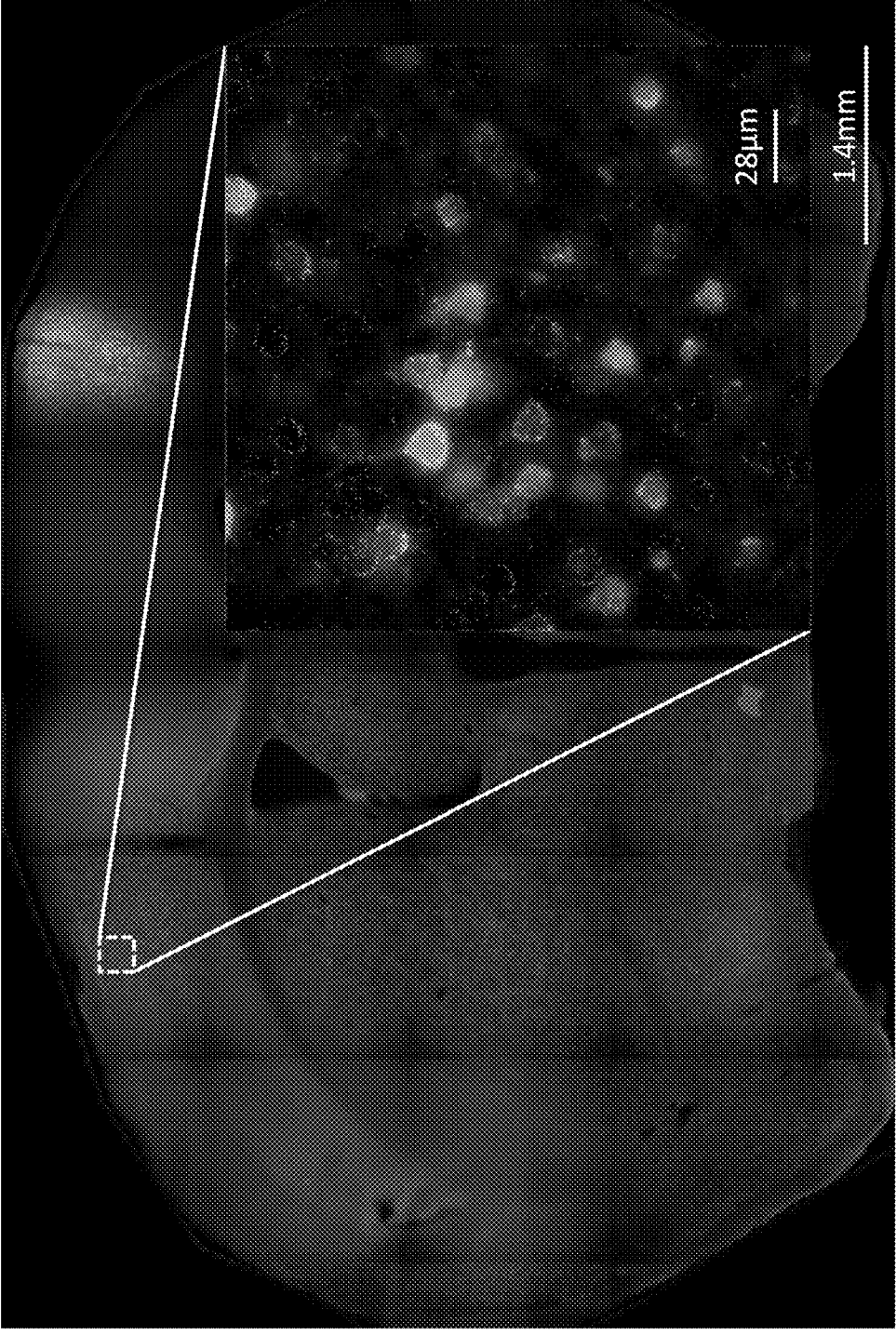
FIG. 13. HCR detection of β-actin (red) in the cortex and visualized with retrograde tracers (fluorogold, green) in a 100 µm coronal section. An entire coronal section was imaged at both 10× and 60× (magnified inset). In the 60× image, individual red dots correspond to single β-actin mRNA molecules. β-actin expression can be quantified by counting fluorescent foci while simultaneously detecting a distal sub-population of neurons tagged with the retrograde tracer (green).
Figure 14:
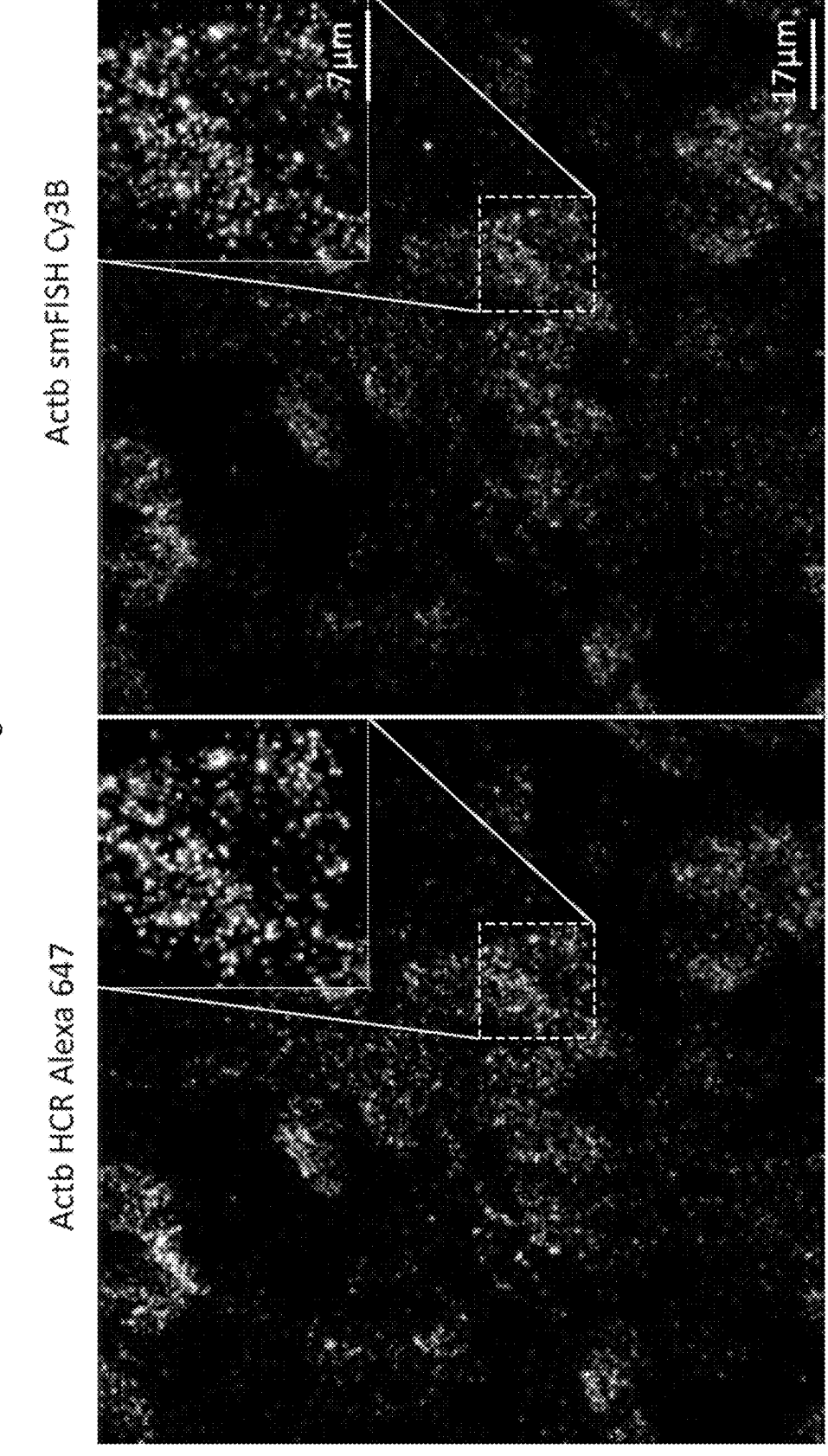
FIG. 14. Detectably labeled oligonucleotides labeled with HCR were as specific as smFISH probes directly labeled with fluorophores in detecting single molecules of RNA in 20 µm brain slices. HCR probes (left) and smFISH probes (right) targeted β-actin simultaneously and co-localized. Note the improved S/N of the HCR.

HCR amplified signals were observed from mRNAs directly in brain slices. When targeted to the same mRNA, HCR probes colocalize with smFISH dots with 90% rate, but are 10-20 times brighter (FIG. 14). This allows HCR probes to be readily detected above the autofluorescence of the brain (FIG. 13). The high colocalization rate proves that HCR is as specific as smFISH and most transcripts are detected.

Figure 15:
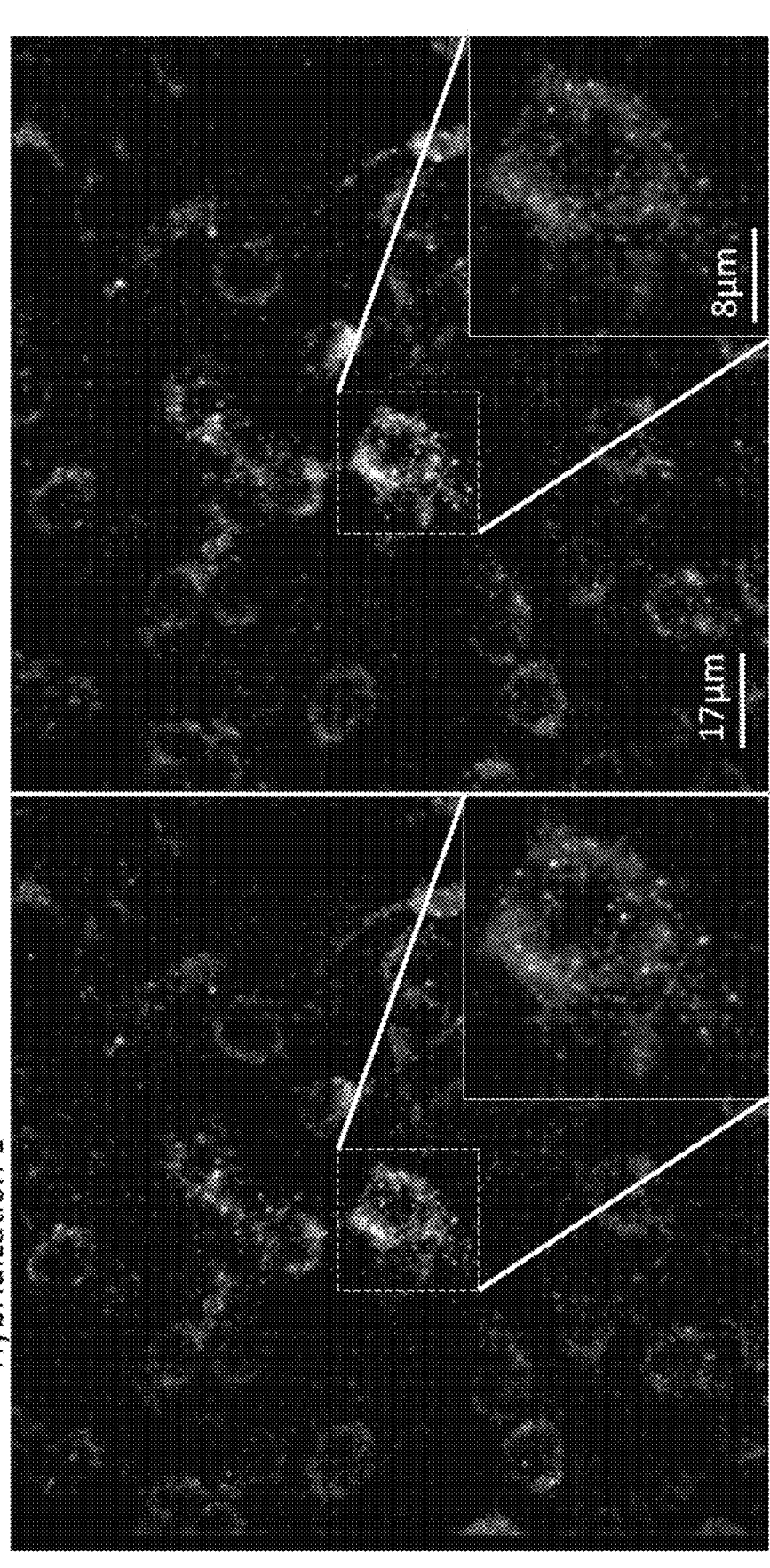
FIG. 15. Detectably labeled oligonucleotides labeled with HCR rehybridized well in 20 µm brain slices. HCR spots in hyb1 and hyb2 colocalized, with DNase treatment in between two hybridizations. This showed that HCR can be fully integrated with the seqFISH protocol.

HCR probes are readily stripped and rehybridized, and can be fully integrated with the seqFISH protocol described herein. FIG. 15 showed the same genes targeted by HCR in brain slices in two different rounds of hybridization. The good colocalization between the two hybridizations shows that HCR-seqFISH works robustly to barcode mRNAs in brain.

HCR protocols work on the same time scale as smFISH hybridization and do not increase the cycle time of the assay. The initial hybridization step in HCR is similar to smFISH in time, while the second amplification step occurs in 30 minutes to 1 hour. Alternative methods of hybridizing RNA probes to the transcripts, and optionally using alternative types of hairpins to amplify the signal can further reduce cycle time. In some embodiments, HCR removes the need to purchase amine labeled oligo probes. Among other things, HCR can potentially decrease the cost of the reagents by approximately one half, to e.g., $10,000 per brain.

Automation. Automation of both hardware and software can be applied to efficiently scale up, for example, to map 100 genes and/or reduce human labor and/or errors. In some embodiments, key pieces of technology are integrated to generate a pipeline and/or optimize workflow for tissue and/or organ imaging, such as imaging of brain slices. Among other things, automated fluidics, image acquisition and/or integrated analysis can be independently and optionally combined with fast hybridization cycle time and imaging time.

Hardware. In some embodiments, an automated system requires minimum intervention from users and can perform the image acquisition automatically once the user has set up the experiments. In some embodiments, each sequencer consists of or comprises an automated epi-fluorescence microscope to perform the imaging and an automated fluidics system to perform the sequential hybridizations. In some embodiments, compressed air is used to push reagents into a 1 cm×1 cm well with cells and tissues fixed on the bottom coverslip. Without the intention to be limited by theory, Applicant notes that, in some embodiments, because of the high viscosity of the hybridization buffer, a compressed air driven system eliminates dead volume and also can be precisely controlled to deliver defined volumes of reagents. In some embodiments, a separate vacuum line is used to purge the chamber. In some embodiments, work flow of a provided protocol is similar to existing DNA sequencers at the time of the present invention, which is well known in the art.

In some embodiments, during each cycle of hybridization, a machine automatically hybridizes samples with probes, washes with buffer to remove excess probes, and/or scans the brain slices for imaging. In some embodiments, wherein DNase is used in a removing step, after imaging DNase is flown in to remove the probes. After extensive wash, another round of hybridization can proceed afterwards. During hybridization time, a microscope moves to a different location on the stage to image another brain slice that has been hybridized and washed already. In such a way, a camera is acquiring images most of the time, while other samples on the stage are being hybridized.

Software. In some embodiments, software is used, for example, to automate the control process and analysis of data. In some embodiments, codes are written in Micromanager, a free software supported by the National Institute of Health, to control a microscope as well as fluidics elements. In some embodiments, valves, stages, light sources, cameras and/or microscopes are controlled through Micromanager.

In some embodiments, compressed sensing is used for dense images (Zhu et al., Faster STORM using compressed sensing. Nat. Methods. 2012, 9(7):721-3) and deconvolution methods are used to separate out the spots in dense clusters. In some embodiments, improvement in image analysis increases multiplex capacity of provided methods, e.g., seqFISH (for example, by about 4-5 folds beyond the 100 gene multiplex). In some embodiments, efficiency is improved in a similar fashion to improvement from the Illumina GAII sequencer to the HiSeq machines, wherein using image processing methods to analyze densely packed clusters on the sequencing chip increased the throughput. In some embodiments, data acquisition and analysis are integrated in a user-friendly package.

In some embodiments, provided technology provides software packages for data analysis. In some embodiments, provided technologies provide software packages for data analysis in Python and Matlab. Images of provided technologies can be a variety of sizes, and can the optionally optimized if desirable. In some embodiments, each FOV is 6 Megapixels at 14 bits depth, corresponding to 1.5 MB of data per image. In some embodiments, about 100 GB of data are generated per run. In some embodiments, provided technologies provide methods for data processing and/or mitigating data log jam. In some embodiments, data log jam is mitigated by segmenting out the spots from each image, fitting them with 2 dimensional Gaussian distributions and recording the center position of the fits. In some embodiments, provided technologies save computer space by discarding raw images and saving processed data.

Light sheet microscopy with CLARITY cleared brain slices. In some embodiments, provided technologies provide methods for imaging a tissue, an organ and/or an organism. In some embodiments, provided technologies provide methods for measuring thick tissues or organs. In some embodiments, a thick tissue or organ has a thickness of about or more than 100 μm. In some embodiments, provided technologies preserves long range projections and morphology beyond within single cells. In some embodiments, light sheet microscopy is used for measuring thick tissues or organs. In some embodiments, a tissue, an organ, and/or an organism is cleared by CLARITY (Chung et al., Structural and molecular interrogation of intact biological systems, *Nature,* 2013, doi:10.1038/nature12107).

Figure 16:
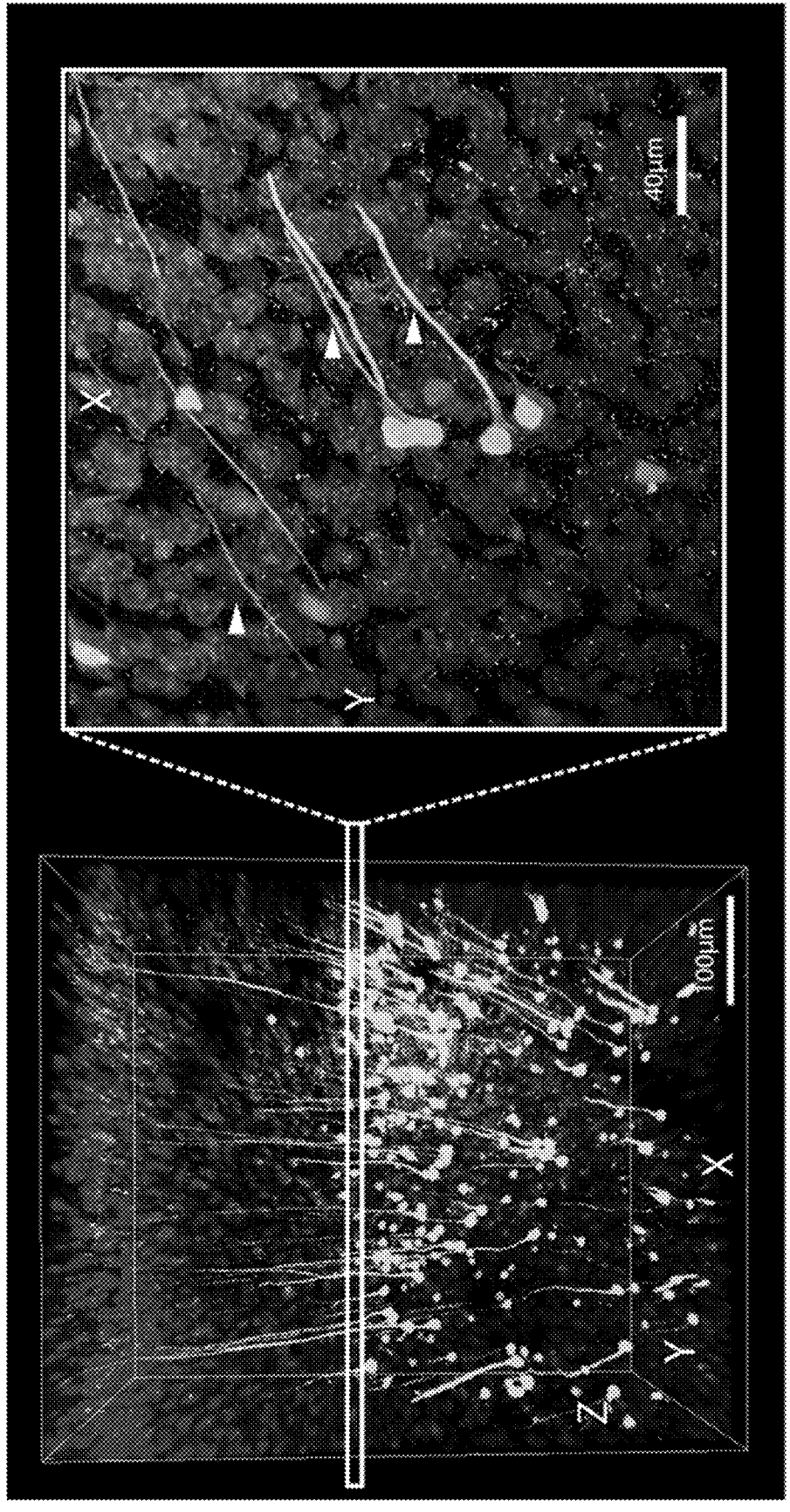
FIG. 16. CLARITY with Nissl: 1 mm-thick coronal section (Bregma AP, 2.3-1.3 mm) of a Thy-1-eYFP mouse brain was cleared and stained with NeuroTrace fluorescent Nissl stain (1:100 dilution, 48 hours, RT). Left, 3d coronal rendering of the motor cortex. Right, 100 µm-thick section of layer V motor cortex. Arrows indicate apical dendrites of the pyramidal neurons (Red-Fluorescent Nissl, Green-eYFP).

In some embodiments, to image thicker brain slices (>100 μm) which better preserves long range projections and morphology, light sheet microscopy, a.k.a. selective plane illumination microscopy (SPIM), are applied on CLARITY cleared brains tissues. In some embodiments, the CLARITY methodology renders the brain transparent for visualization and identification of neuronal components and their molecular identities. In some embodiments, CLARITY turns brain tissue optically transparent and macromolecule-permeable by removing light scattering lipids, which are replaced by a porous hydrogel to preserve the morphology of brain tissue, so that studies can be conducted without thinly sectioning the brain, which enables visualization of neurons of interest as well as their long-range synaptic connectivity. Without the intention to be limited by theory, Applicant notes that compared to FISH that was previously performed in culture or thin slices prior to the present invention, provided technologies can use thicker tissues and allow for more accurate reconstructions of individual neurons or 3D neuronal networks transcriptome. FIG. 16 illustrates a successful, validated Clarity-based protocol to prepare optically clear thick slices compatible with FISH staining: (1) 100 micron coronal brain slices in 2 mL Eppendorf tubes were incubated in 1.5 mL of 4% Acrylamide, 2% formaldehyde, 0.25% thermo-initiator, 1×PBS at 4 degrees overnight; (2) nitrogen gas was bubbled through the hydrogel solution for 10 seconds; (3) degassed samples were incubated for 2 hours at 42 degrees to polymerize; (4) samples were washed 3 times in PBS and incubated in 10% SDS, 1×PBS at 37 degrees for 4 hours to clear; and (5) samples were washed 3 times in PBS and ready to be used for seqFISH.

In some embodiments, provided technologies provide methods for minimizing or preventing out-of-focused background. In some embodiments, provided technologies utilize imaging technologies that minimize or prevent out-of-focused background. In some embodiments, SPIM is used for thicker slices that have higher out-of-focused background. In some embodiments, while confocal microscope can reject this background, it scans slowly and photobleaches the upper layers of sample while imaging the lower layers. In some embodiments, in SPIM only the layer that is being imaged is illuminated by excitation light. In some embodiments, in a SPIM setup useful for provided technologies, two objectives placed perpendicular to each other are suspended over the sample at approximately 55°. In some embodiments, a light sheet is generated using a cylindrical lens to focus one axis of the beam into an about 10 μm height and an effective width or FOV of about 200 μm.

Figure 17:
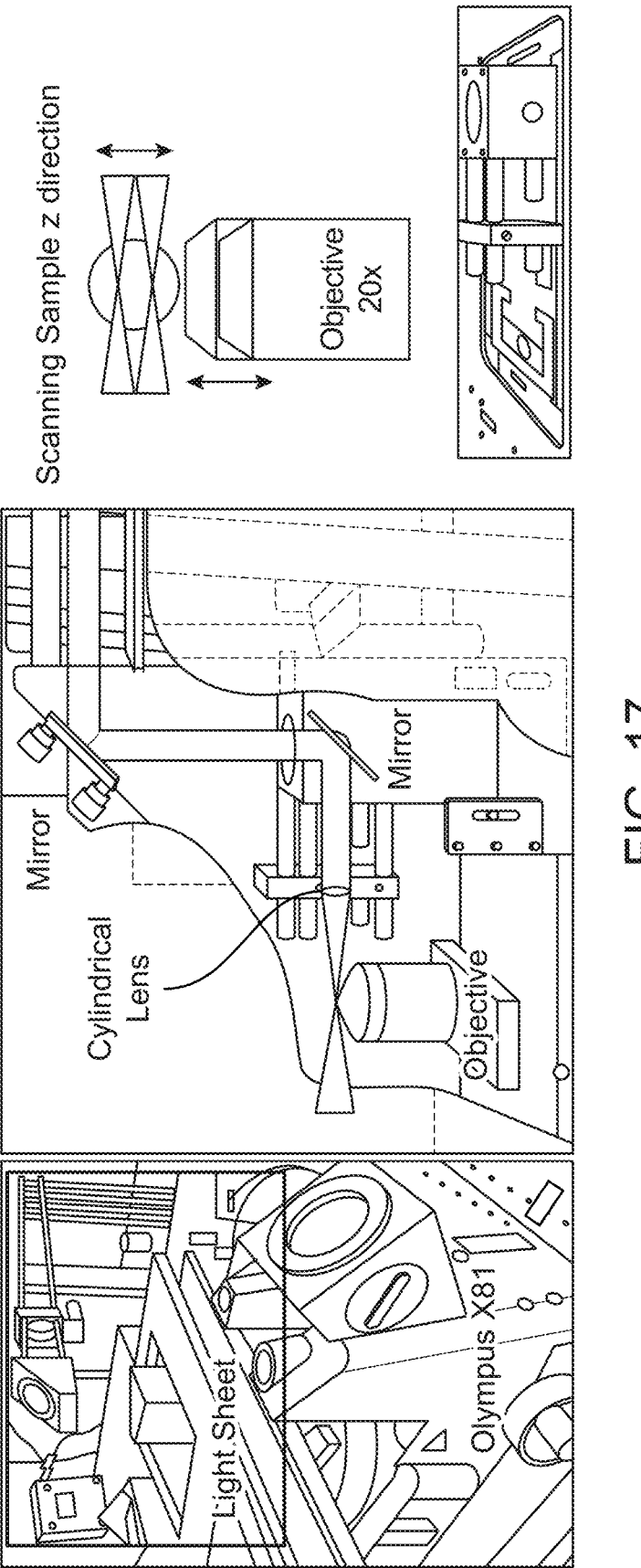
FIG. 17. A schematic display of an exemplary light sheet microscope.

In some embodiments, the present invention provides microscope setups for provided methods. In some embodiments, the present invention provides a light sheet microscope, wherein the sample is illuminated from the side. In some embodiments, a light sheet is parallel to a sample stage. In some embodiments, a light sheet is perpendicular to the detection objective. An exemplary setup of light sheet microscope is illustrated in FIG. 17. By adapting two mirrors and a cylindrical lens, a plane of light sheet is created and illuminates the sample from the side, and is perpendicular to the detection objective (middle). The bottom mirror is connected to the cylindrical lens and mounted directly onto the same base of objective. With this configuration, the objective is moving synchronically with the illumination sheet, allowing scanning the sample along z-axis (right, top). The right (bottom) figure also shows that, the sample is mounted inside the hybridization chamber, and imaged by an air objective below.

Figure 18:
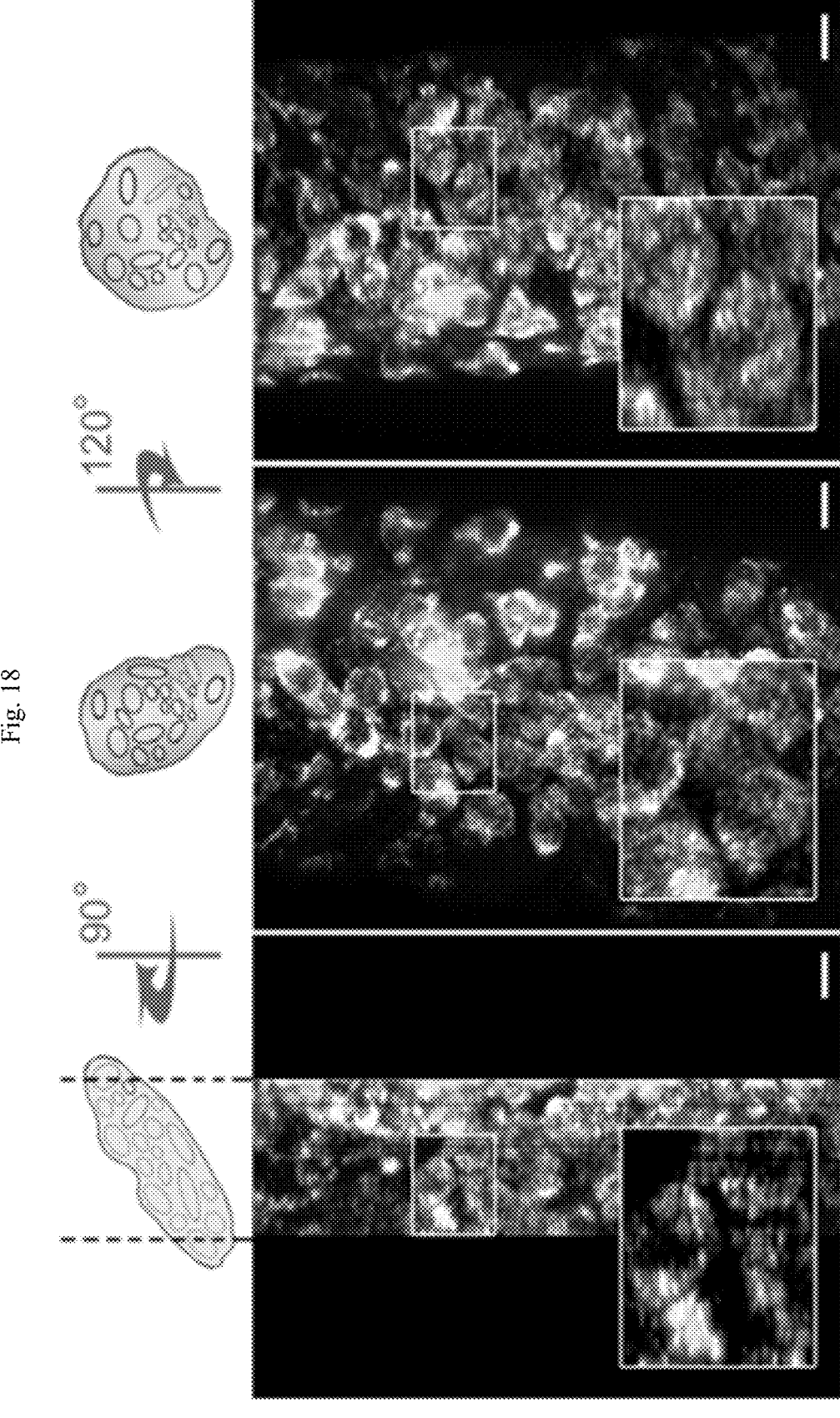
FIG. 18. SPIM detects single mRNAs in 100 µm CLAR-ITY brain slices. The slice was scanned over 100 µm. The images were then registered and stitched to a 3D reconstruction. Diffraction limited dots in the image corresponded to single β-Actin mRNAs detected by HCR. Scale bar is 15 µm.

As illustrated in FIG. 18, SPIM images were acquired with a 100 μm brain slice that was CLARITY cleared and hybridized with HCR probes against β-actin. 200 optical sections with 0.5 μm spacing were taken to generate the reconstruction. Clear HCR signals were observed with a 20× water immersion objective. The β-actin mRNA is highly expressed, accounting for the large number of dots in the cell bodies. However, clear diffraction limited spots were also observed in axons.

In some embodiments, HCR-seqFISH protocol to CLARITY cleared brains and SPIM microscopy can be adapted. 100 μm slices were efficiently hybridized in 4-5 hours, indicating that detectably labeled oligonucleotide probes can diffuse readily in 100 μm thick but cleared slices. In addition, DNase enzyme diffused readily as well to strip HCR signal from the slice (FIG. 15). In some embodiments, provided technologies provide detectably labeled oligonucleotides, such as FISH and HCR probes, that are smaller than antibodies that persons having ordinary skill in the art routinely diffuse into 1 mm thick coronal slices, and provide profiling of targets for whole tissues or organs, e.g., performance of seqFISH on CLARITY cleared whole brains.

In some embodiments, provided technologies provide geometries of microscopy. In some embodiments, provided technologies provide alternative geometry of SPIM such that thick brain slices (>100 μm) and potentially entire CLARITY cleared brain can be mounted on an epifluorescence microscope with a long working distance objective. In some embodiments, a light sheet is generated perpendicular to the imaging axis, and sections the sample, mounted at an angle on the microscope, with 10 μm width over 200-300 μm. In some embodiments, a provided geometry allows direct carry-over of a developed flow chamber and automation design. In some embodiments, fiducial markers in brain slices are used to register successive slices. In some embodiments, nanoscopic rods are injected into the brain prior to sectioning, allowing good registration between different sections.

Speed. In some embodiments, imaging speed limits the ultimate throughput. In some embodiments, provided HCR amplification provides more than sufficient number of photons for imaging, and less expensive cameras can be used to image the sample. In some embodiments, light from the collection objective can be split into multiple, e.g., 6 distinct paths (e.g., 5 fluorescence and 1 DAPI) with imaging flat dichroics and filters. This dramatically increases the throughput of in situ "sequencers," such that an entire brain can be completed in 1 week on a single microscope.

Target genes selection. In some embodiments, the present invention provides technologies for selecting and imaging a set of targets, such as a set of transcripts and/or DNA loci (e.g, a set of 100 targets as exemplified). In some embodiments, target genes are chosen from the in situ database from the Allen brain atlas (ABA). Multiple criteria can be used to select genes of interest, e.g., those likely to represent the cellular identity in the cortex region. Computational selection of an optimal set of genes from overlapping criteria is well-known (2.

Alon, N; Moshkovitz, Dana; Safra, Shmuel (2006), "Algorithmic construction of sets for k-restrictions", ACM Trans. Algorithms (ACM) 2 (2): 153-177, ISSN 1549-6325; 8.

Cormen, T H.; Leiserson, Charles E.; Rivest, Ronald L.; Stein, Clifford (2001), Introduction to Algorithms, Cambridge, Mass.: MIT Press and McGraw-Hill, pp. 1033-1038, ISBN 0-262-03293-7; 12. Feige, U (1998), "A threshold of ln n for approximating set cover", Journal of the ACM (ACM) 45 (4): 634-652, ISSN 0004-5411). In some embodiments, set-cover-heuristics (Pe'er, 2002) are used to select genes that: 1. are known to define sub cell types; 2. exhibit "salt and pepper" expression patterns in the ABA; 3. belong to a family of genes such as transcription factors, ion channels, GPCRs, and neurotropins; and 4. culled from RNA-seq experiments from cortex samples. For instance, SLC1A3 marks glia cells while SLC6A1 marks inhibitory neurons, and SLC17A7 marks excitatory neurons. In some embodiments, genes with heterogeneous expression pattern such as PVALB, SST and CALB2 mark out subsets of inhibitory neurons. An exemplary set of 100 genes is shown below:

| Gene Name | Expression Profile |
| --- | --- |
| SLC6A1 | all inhibitory (I) |
| SLC17A7 | all excitatory (E) |
| SLC1A3 | glia |
| PVALB | subset I |
| SST | subset I |
| CALB2 | subset I |
| LER5 | Isocortex |
| TNNC1 | Isocortex |
| MYL4 | Isocortex |
| SATB2 | Isocortex |
| CCL27a | Isocortex |
| BOC | Primary Motor L1 |
| DACT2 | Primary Motor L1 |
| LHX1 | Primary Motor L1 |
| PVRL3 | Primary Motor L1 |
| SLC44a3 | Primary Motor L2/L3 |
| KLK5 | Primary Motor L2/L3 |
| TNNC1 | Primary Motor L2/L3 |
| WNT6 | Primary Motor L2/L3 |
| ZMAT4 | Primary Motor L5 |
| STARD8 | Primary Motor L5 |
| TCF21 | Primary Motor L5 |
| MYL4 | Primary Motor L5 |
| KRT80 | Primary Motor L6a |
| OLFR19 | Primary Motor L6a |
| TBC1d30 | Primary Motor L6a |
| OLF16 | Primary Motor L6b |
| EAR6 | Primary Motor L6b |
| CHIT1 | Primary Motor L6b |
| SLN | Secondary Motor L1 |
| ADAMTS8 | Secondary Motor L1 |
| EPYC | Secondary Motor L1 |
| KCNV1 | Secondary Motor L1 |
| pcdh7 | Secondary Motor L2/L3 |
| GLT8d2 | Secondary Motor L2/L3 |
| HKDC1 | Secondary Motor L2/L3 |
| SRPX | Secondary Motor L3 |
| ZFP458 | Secondary Motor L3 |
| SLC30a8 | Secondary Motor L3 |
| GK5 | Secondary Motor L5 |
| TEX28 | Secondary Motor L5 |
| MS4a10 | Secondary Motor L5 |
| KRT16 | Secondary Motor L6a |
| KRT42 | Secondary Motor L6a |
| DOC2a | Secondary Motor L6a |
| KRT33b | Secondary Motor L6b |
| YBX | Secondary Motor L6b |
| PNPLA5 | Secondary Motor L6b |
| TMEM215 | Primary Somatosensory L1 |
| SDC1 | Primary Somatosensory L1 |
| PREX1 | Primary Somatosensory L1 |
| DIEXF | Primary Somatosensory L1 |
| DHRS7c | Primary Somatosensory L2/L3 |
| DDIT4l | Primary Somatosensory L2/L3 |
| TDG | Primary Somatosensory L2/L3 |
| EPSTI1 | Primary Somatosensory L2/L3 |
| RORb | Primary Somatosensory L4 |
| GSC2 | Primary Somatosensory L4 |
| KRT10 | Primary Somatosensory L4 |
| GCA | Primary Somatosensory L4 |
| DCBLD2 | Primary Somatosensory L5 |
| ABCD2 | Primary Somatosensory L5 |
| GTDC1 | Primary Somatosensory L5 |
| IL17RA | Primary Somatosensory L6a |
| TBR1 | Primary Somatosensory L6a |
| PPID | Primary Somatosensory L6a |
| IGHM | Primary Somatosensory L6b |
| MMGT1 | Primary Somatosensory L6b |
| CPLX3 | Primary Somatosensory L6b |
| ART2b | Secondary Somatosensory L1 |
| GNB4 | Secondary Somatosensory L1 |
| B3GAT2 | Secondary Somatosensory L1 |
| PDC | Secondary Somatosensory L2/L3 |

-continued

| Gene Name | Expression Profile |
| --- | --- |
| ADIG | Secondary Somatosensory L2/L3 |
| FPR1 | Secondary Somatosensory L2/L3 |
| INHBC | Secondary Somatosensory L4 |
| RUFY4 | Secondary Somatosensory L4 |
| HGFAC | Secondary Somatosensory L4 |
| EFCAB4b | Secondary Somatosensory L5 |
| SSTR2 | Secondary Somatosensory L5 |
| ZFP395 | Secondary Somatosensory L5 |
| CCDC36 | Secondary Somatosensory L6a |
| ST14 | Secondary Somatosensory L6a |
| MYL12b | Secondary Somatosensory L6b |
| RSPO2 | Secondary Somatosensory L6b |
| NDNF | L1 (I) |
| RASGRF2 | L2/3 (I) |
| CUX2 | L2/3/4 |
| RORB | L4 |
| SCNN1A | L4 |
| ETV1 | L5 |
| FEZF2 | L5 |
| BCL6 | L5 |
| TRIB2 | L5a |
| FOXP2 | L6 |
| TLE4 | L6/L6b |
| CTGF | L6b |
| CYLD | L2/3 |
| CMTM3 | L2/3 |
| ANKRD6 | L2/3 |

Integration of seqFISH with protein detection, organelle markers and activity measurements. In some embodiments, provided technologies, e.g., seqFISH, allow multiplex analysis of RNA, as well as proteins, neural activities, and structural arrangements in the same sample in situ with single cell resolution. Antibodies for specific targets can be hybridized in one additional round of hybridization to the sample. In some embodiments, provided methods optionally comprise a step of immunostaining. In some embodiments, multiple antibodies are used to detect many protein targets in sequential rounds of hybridization (Schubert W et al. Analyzing proteome topology and function by automated multidimensional fluorescence microscopy. Nat Biotechnol (2006) 24(10):1270-1278). Applicant notes that there are up to about 100-1000 or more fold higher abundance of proteins over mRNAs in cells. Targeted proteins can mark cellular organelles such as mitochondria, ER, transport vesicles, cytoskeleton, as well as synaptic junctions. For example, MAP2 antibodies can be used to mark out cell boundaries to help segmentation of axons and dendrites.

Live observation of brain slices can be imaged on the epi-fluorescence and light sheet microscope prior to transcription profiling by provided methods (e.g., seqFISH). Calcium (Nakai J, Ohkura M, Imoto K (February 2001). "A high signal-to-noise Ca(2+) probe composed of a single green fluorescent protein". *Nat. Biotechnol.* 19 (2): 137-41; Akerboom et al., "Optimization of a GCaMP calcium indicator for neural activity imaging." J Neurosci. 2012 Oct. 3; 32(40):13819-40; Stosiek et al., "In vivo two-photon calcium imaging of neuronal networks." *Proceedings of the National Academy of Sciences* 100 (12): 7319) and voltage sensor (Cohen, et al., "Optical Measurement of Membrane Potential" in Reviews of Physiology." Biochemistry and Pharmacology, vol. 83, pp. 35-88, 1978 (June); Mutoh et al., Genetically Engineered Fluorescent Voltage Reporters ACS Chem Neurosci. 2012 Aug. 15; 3(8): 585-592; Peterka et al., Imaging voltage in neurons. Neuron. 2011 Jan. 13; 69(1): 9-21) can be imaged in the brain slices. SPIM allows efficient and fast imaging of these sensors in brain slices. Brain slices are fixed on the microscope and provided protocols such as seqFISH protocols can be performed with automated fluidics. In some embodiments, in addition to the live measurements, mRNAs of activity dependent immediate early genes (IEGs) are detected as a measure of the integrated neural activities in the neurons. For example, CamKII and cFos were readily detected in neurons with heterogeneous expression levels; they can be incorporated in a set of genes, e.g., an exemplary 100 gene multiplex or FISHed separately in additional cycles depending on abundance.

Integrating Connectomics and seqFISH to Identify Molecular Identities of Distinct Neurons within Different Somatic Sensorimotor Neural Networks.

To systematically characterize the molecular identities of distinct neuronal populations within the somatic sensorimotor neural networks using provided technologies. In some embodiments, neuronal populations within the same functional subnetworks can share common sets of marker genes, but also have heterogeneous expression of other genes that defines identity at a cellular level. In some embodiments, cells in different subnetworks differ more in their expression patterns. Exemplary cortico-cortical somatic subnetworks each of which controls a basic class of sensorimotor function are: (1) orofaciopharyngeal for eating and drinking, (2) upper limbs for reaching and grabbing, (3) lower limbs for locomotion, and (4) whisker for rhythmic whisker movements. In some embodiments, provided technologies provide a novel and rigorous approach for characterizing molecular identities of cortical neurons with distinct neural networks and provide invaluable information for understanding genetic circuits underlying the wiring diagram of the mammalian brain.

Figure 19:
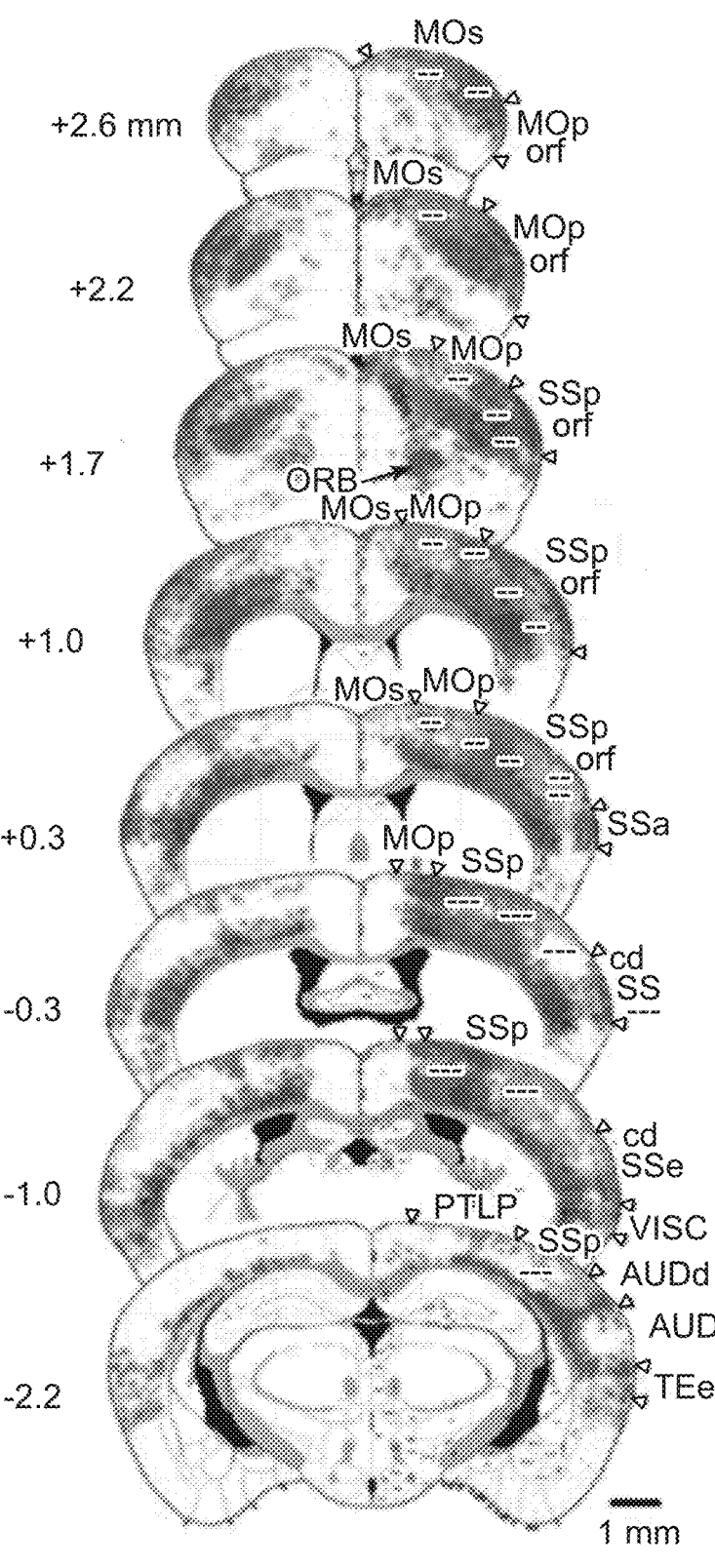
FIG. 19. A connectivity map of the cortical somatic sensorimotor subnetworks on serial coronal levels of the Allen Reference Atlas. It shows that each of the four major components of somatic sensorimotor areas, SSp, SSs, MOp, and MOs, are divided into 4 functional domains. These functionally correlated domains are extensively interconnected with all others and form four major cortical somatic sensorimotor subnetworks: orofaciopharyngeal (orf, blue), upper limb (ul, green), lower limb and trunk (ll/tr, red), and whisker (bfd.cm & w, yellow). Numbers indicate position of sections relative to bregma (mm). Provided methods can characterize connectivity and molecular identities of projection neurons in each of these distinct domains within different subnetworks.
Figure 20:
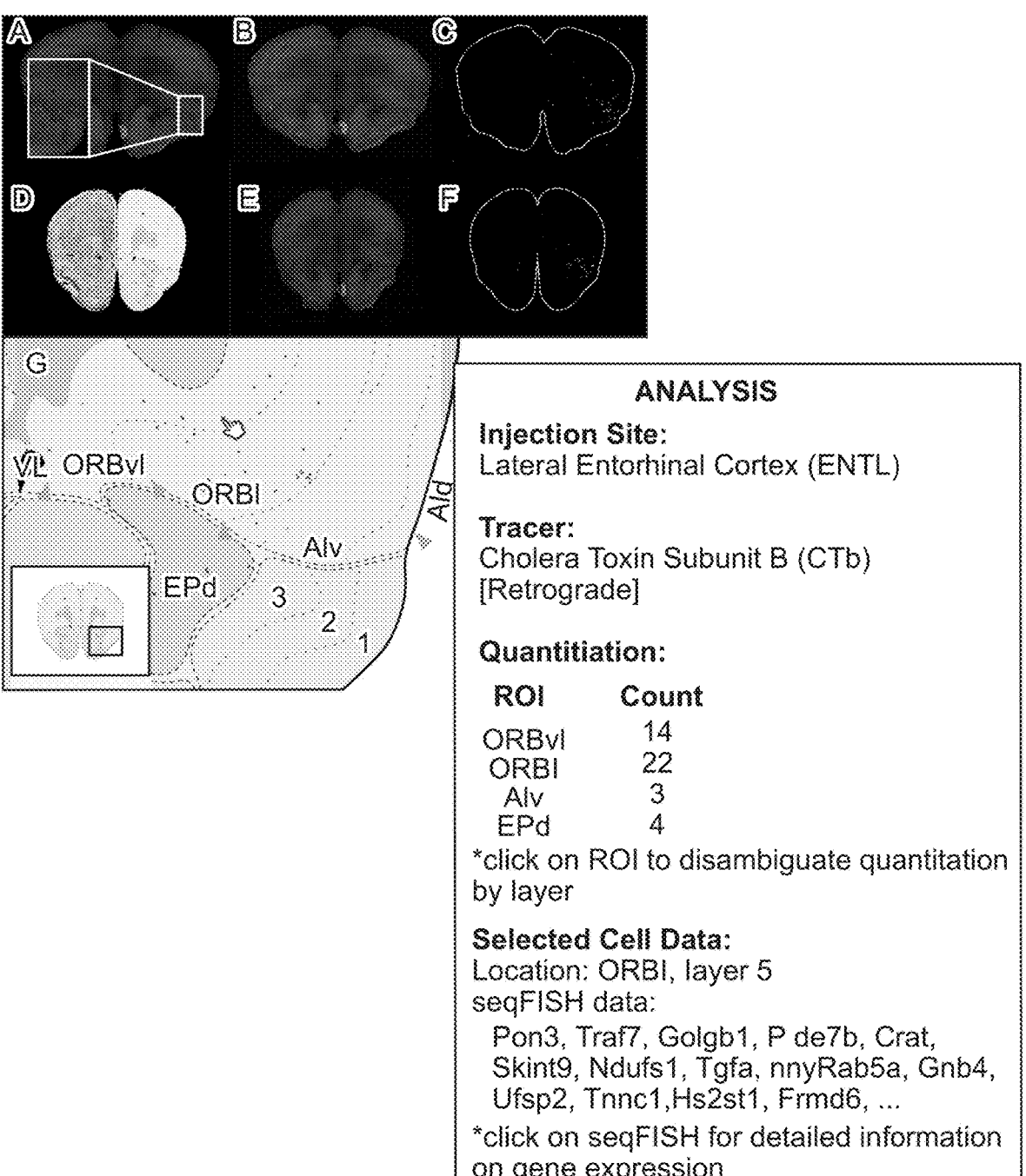
FIG. 20. Exemplary informatics workflow for automatically detecting and mapping retrogradely labeled neurons and gene barcoding information. A. Raw image with CTb labeling (pink) and Nissl staining (blue). The boxed area shows a close-up view of CTb labeled neurons. B. Multi-channel raw image are converted into grayscale for segmentation. C. Individual tracer channel images are run through a segmentation pipeline that discretely separates the tissue background from labeled cells. White dots are reconstructions of labeled somata. D. Reintegrated multi picture tiffs are associated with a coronal section in the ARA for registration. E. Using provided developed registration software, multi picture tiffs are warped to align both the tissue's silhouette and cytoarchitectural delineations to its corresponding ARA level. F. Cells extracted via the segmentation process are spatially normalized and can be associated with a layer- or sub-nucleus-specific ROI within the ARA. G. Segmented and registered labeling reconstructions are made available to the public on the iConnectome FISH viewer, along with their accompanying seqFISH data. An analysis tab provides information about the injection site, tracer type, number of labeled cells by ROI, which can be further disambiguated into layer-specific cell counts, and gene expression by cell.

Using a collection of neuronal pathways, digital cortical connectivity atlas can be generated to display raw images of tract tracing studies. Pathways can be graphically reconstructed to create cortico-cortical connectivity map to help analysis of large-scale data. Based on intracortical connectivity, four distinct cortico-cortical somatic subnetworks can be established each of which controls a basic class of sensorimotor function. Each of these subnetworks comprises 4-5 distinct functional domains in the primary somatic sensory (SSp), primary somatomotor (MOp), secondary somatomotor (MOs), and supplementary somatosensory (SSs) cortical areas, which were further subdivided according to their strength of connectivity with other somatic sensorimotor areas corresponding to a specific body subfield. In some embodiments, the orofaciopharyngeal subnetwork comprises five major nodes: (1) the SSp mouth and nose domain (SSp-m/n); (2) the MOp orofacial domain (MOp-orf); (3) the MOs rostrodorsolateral domain (MOs-rd1); (4) the SSp barrel field anterolateral domain (SSp-bfd.al); and (5) the SSs rostral and caudoventral domain (SSs-r & cv). In some embodiments, the four major nodes of the upper limb subnetwork comprise (1) the SSp upper limb (SSp-ul); (2) MOp-ul; (3) rostrodorsal MOs (MOs-rd); and (4) caudodorsal SSs (SSs-cd). In some embodiments, the lower limb/trunk subnetwork comprise the SSp lower limb/trunk region (SSp-ll/tr), the MOp-ll/tr, and the rostrodorsomedial MOs (MOs-rdm) (FIG. 10 B-D). In some embodiments, the whisker subnetwork comprises the caudomedial SSp-bfd (SSp-bfd.cm), MOp-w, which corresponds to the vibrissal primary motor cortex (vM1) and the caudodorsal SSs (SSs-cd; FIG. 19). Exemplary data are described by the Mouse Connectome Project (www.mouseconnectome.org).

To determine molecular identities of distinct neuronal populations in each of these somatic sensorimotor subnetworks, multi-fluorescent retrograde tracers are used to label neurons, and provided technologies such as seqFISH can be applied to determine the gene expression profile of retrogradely labeled population at single cell resolution. To label the neuronal populations, multiple (e.g., five) retrograde tracers are injected into five of the main targets of one of the main nodes of each sensorimotor subnetwork in the same animal (tracer information below). For example, in one animal, circuit tracers are injected into two of the major cortical nodes (SSp-bfd.al and SSs-r & cv) and three of the subcortical nodes (caudoputamen ventrolateral domain, CP-vl; ventral posteromedial thalamic nucleus, VPM; and ventral spinal trigeminal nucleus, SPV) of the orofaciopharyngeal subnetwork. This simultaneously back labels five different neuronal populations in all of the other nodes of the orofaciopharyngeal subnetwork. In this example, labeled neurons are in the SSp-m/n domain and in the MOp-oro.

On the other hand, tracer can be injected into four different SSp body subfield domains (i.e. SSp-m/n, SSp-ul, SSp-ll/tr, and SSp-bfd.cm), each of which belongs to a distinct somatic subnetwork. This simultaneously labels distinct neuronal populations in cortical areas associated with the different subnetworks. In this case for example, back labeled neurons are observed in the MOp domains associated with each subnetwork, i.e MOp-orf, MOp-ul, MOp-ll/tr, and MOp-w. This injection strategy applied to all the main nodes and subcortical targets of each of the four somatic sensorimotor subnetworks labels distinct neuronal populations of each of the subnetworks.

After injection of the tracers (e.g., one week following the injection of the tracers), animals are sacrificed, and their brains are harvested and coronally sectioned at 20 μm or 100 μm thickness for seqFISH analysis of back labeled neurons. Genes, such as the exemplified approximately 100 genes that are richly expressed in the somatic sensorimotor cortical areas (SSp, MOp, MOs, SSs) can be preselected for profiling using, for example, the online digital gene expression database of the Allen Brain Atlas project (www.Brian-Map.org) (Lein et al., 2007 Genome-wide atlas of gene expression in the adult mouse brain. Nature, 11;

Injection strategy and post injection processing. Three hundred 4-week-old male C57Bl/6 mice are used. In one animal, five fluorescent retrograde tracers are injected into either different nodes within the same somatic sensorimotor subnetworks, or different nodes in different somatic subnetworks as described above (FIG. 19). The tracers are Fluorogold (FG, yellow), cholera toxin b conjugated with 488 or 647 (CTb-488 [green], CTb-647 [pink]), red retrobeads (RR, red), and wheat germ agglutinin conjugated with 655 (WGA-Qdot655, white). Since Qdot655 has an excitation wavelength that differs from CTb 647, it can be captured into a different channel and pseudocolored with a unique hue. The tracers are injected (either iontophoretically or with pressure injection) via stereotaxic surgeries. Details on surgeries and perfusions are described, e.g., in Hintiryan et al., Comprehensive connectivity of the mouse main olfactory bulb:analysis and online digital atlas. Front Neuroanat. 2012 Aug. 7; 6:30. eCollection 2012. In some embodiments, two paired mice are injected with the same tracers used in the exact same coordinates. One of the animals is used to validate locations of labeled cells and injection sites, while the other is subjected to provided, e.g., seqFISH methods. One is perfused following tracer transport, and brains are coronally sectioned into 50 μm thickness sections and collected in four series. One in four series of sections is counterstained with a fluorescent Nissl stain solution (NeuroTrace Blue [NTB]), mounted onto glass slides, and imaged using an Olympus VS120 virtual microscopy system. In some embodiments, the Nissl stain provides cytoarchitectonic background for visualizing precise anatomical location of back labeled cells. These images are processed through an informatics pipeline so that every individual image is faithfully registered onto its corresponding level of the Allen Reference Atlas (ARA). This Nissl, along with provided informatics tools, enables automatical and precise counting of the approximate number of each tracer labeled neuronal population in each ROI (in this case, the different domains of somatic sensorimotor areas). The distribution patterns are automatically plotted onto the corresponding atlas level to create their connectivity map.

The paired mice are sacrificed at the same time and their brains are sectioned at either 20 μm or 100 μm thickness for seqFISH analysis. These sections are first imaged under 20× (or 10×) objective to reveal back labeled neurons with different tracers. Brain sections through all coronal levels containing the somatic sensorimotor areas are used to perform seqFISH for an exemplified set of 100 genes. This method reveals the gene expression in every tracer labeled neuron. All images are analyzed first for gene expression profiles of each individual tracer labeled neurons. Each section is registered back to the closest matched section of its paired brain so that sections at approximately the same coronal level from the paired brains can be displayed alongside in a connectome viewer. As such, molecular profiles of different neuronal populations are displayed within its closest matched anatomic background. In some embodiments, gene expression profiles are correlated in each retrogradely labeled neuronal population.

Results. In some embodiments, distinct retrogradely labeled neuronal populations within different somatic sensorimotor areas display different transcriptome profiles; even neuronal populations in the same domain (e.g., SSp-m) that are labeled with different tracers display distinct gene expression profile from its neighboring neurons that have different connectivity profiles. In some embodiments, different neuronal populations within different somatic sensorimotor nodes within the same subnetwork (e.g., SSp-m, MOp-orf, SSp-bfd.al, and SSs-r) share common network-specific genes, while neuronal populations within different neural networks (e.g., the orofaciopharyngeal and lower limb/trunk subnetworks) display very distinct transcriptome profiles. In some embodiments, regional (e.g., SSp or MOp) or laminar (different layers) specific genes are identified for those neurons in different cortical areas and different layers.

As exemplified, provided technologies provide a unique combination of fluorescent tract tracing with seqFISH technology to characterize molecular identities of connectivity-based neuronal populations (cell types) within distinct somatic sensorimotor networks with subneuronal resolution and faithful anatomic background. See, e.g., FIGS. 3 and 9 for exemplary results. In some embodiments, provided technologies comprise measuring other parameters in parallel (i.e. antibody and organelle stains, as well as IEG expression levels), and can be applied to the entire neocortex or brain.

High throughput pipelines and informatics tools for analyzing and presenting data online. In some embodiments, provided technologies provide high throughput pipelines and informatics tools for analyzing and presenting data online through, e.g., a publicly accessible database, such as www.MouseConnectome.org). In some embodiments, provided technologies provide integration with Mouse Connectome Project, whose broad scope of study and use of multi-fluorescent imaging make it a valuable tool among the connectomic community and well suited for studying long-range connectivity in the mouse brain. For example, it offers online visualization tools that allow users to visualize multiple fluorescent labeled pathways on the top of their own cytoarchitectural background and corresponding ARA atlas level. In some embodiments, to faithfully associate seqFISH information with its corresponding retrogradely labeled somata, labeled cell bodies are discretely segmented from tissue background and from images of the same section, but acquired at different rounds (e.g., first for image retrograde tracers, then for different mRNA in seqFISH), and spatially indexed by their coordinates relative to a fixed reference point on either the slide and/or an anatomical landmark in the tissue. In some embodiments, to associate data with a stereotaxic coordinate defined in the ARA, the present invention provides a novel registration pipeline that dramatically increases registration accuracy (i.e. warping each scanned microscopy image to the shape of the corresponding level of the ARA), and image segmentation that automatically and accurately enumerates fluorescently labeled neurons in a given ROI (e.g., SSp-m, MOp-11). In some embodiments, provided technologies collectively allow for labeling and seqFISH data from multiple tracers within a brain, and across multiple brains, to be collated into a single anatomical framework for the purposes of visualization and annotation.

In some embodiments, images are registered at corresponding atlas levels of the Allen Reference Atlas (Dong, H. W. (2008). The Allen Reference Atlas: A Digital Color Brain Atlas of C57BL/6J Male Mouse, John Wiley & Sons). The deformation matrix resulting from the registration process is applied on the original resolution images to get the high-resolution warped images. Following registration and registration refinement, the NeuroTrace® fluorescent Nissl stain is converted to a bright-field image. Next, each channel for every image is adjusted for brightness and contrast to maximize labeling visibility and quality in tools, e.g., iConnectome. After modifications (i.e. skewness, angles) and JPEG2000 file format conversions, images can be published to iConnectome view (www.MouseConnectome.org).

FISH visualization tool. In some embodiments, all connectivity data produced in are processed through the MCP informatics pipeline and presented online through a new iConnectome FISH Viewer (www.MouseConnectome.org). Different from available iConnectome viewer, which displays two anterograde (PHAL and BDA) and two retrograde (FG and CTb) labeling, iConnectome FISH can display up to five different neuronal populations with retrograde fluorescent dyes. As mentioned above, each set of injections can be given to a pair of mice. One can be processed following a regular MCP pipeline and be presented in iConnectome FISH viewer to display multiple fluorescent labeled neuronal populations within their own Nissl-stained cytoarchitetural background and within their corresponding ARA level. These can provide precise anatomic information for each of the fluorescent labeled neuronal populations across the entire brain. Brain sections from its paired partner following seqFISH are registered onto the closest ARA level that its paired partner was registered to and can be displayed side by side in different window. A list of genes that were expressed in the neurons can be listed on the side panel. Upon clicking on the gene, the fluorescently labeled neurons that expressed this gene can light up to indicate its expression locations. This provides a practical way to display the molecular identities of neuronal populations within the global context of connectivity and anatomical background.

In some embodiments, a corresponding database is developed that allows users to analyze these data and to correlate neural connectivity with their molecular identities. This informatics tool is built on top of a database that stores information associated with each retrograde labeled neuronal population (e.g. cell numbers, anatomic location) with gene barcoding. This database can help users to identify corresponding gene barcodes for neurons within the same neural networks or distinct neural networks.

Mapping the whole brain. In some embodiments, provided technologies have sufficient sensitivity, selectivity, automation, and/or spatiotemporal resolution at single neuron level for high-throughput analysis of gene expression in retrogradely labeled neurons for whole brains.

Additional Exemplary Methods for Removing Steps

Figure 21:
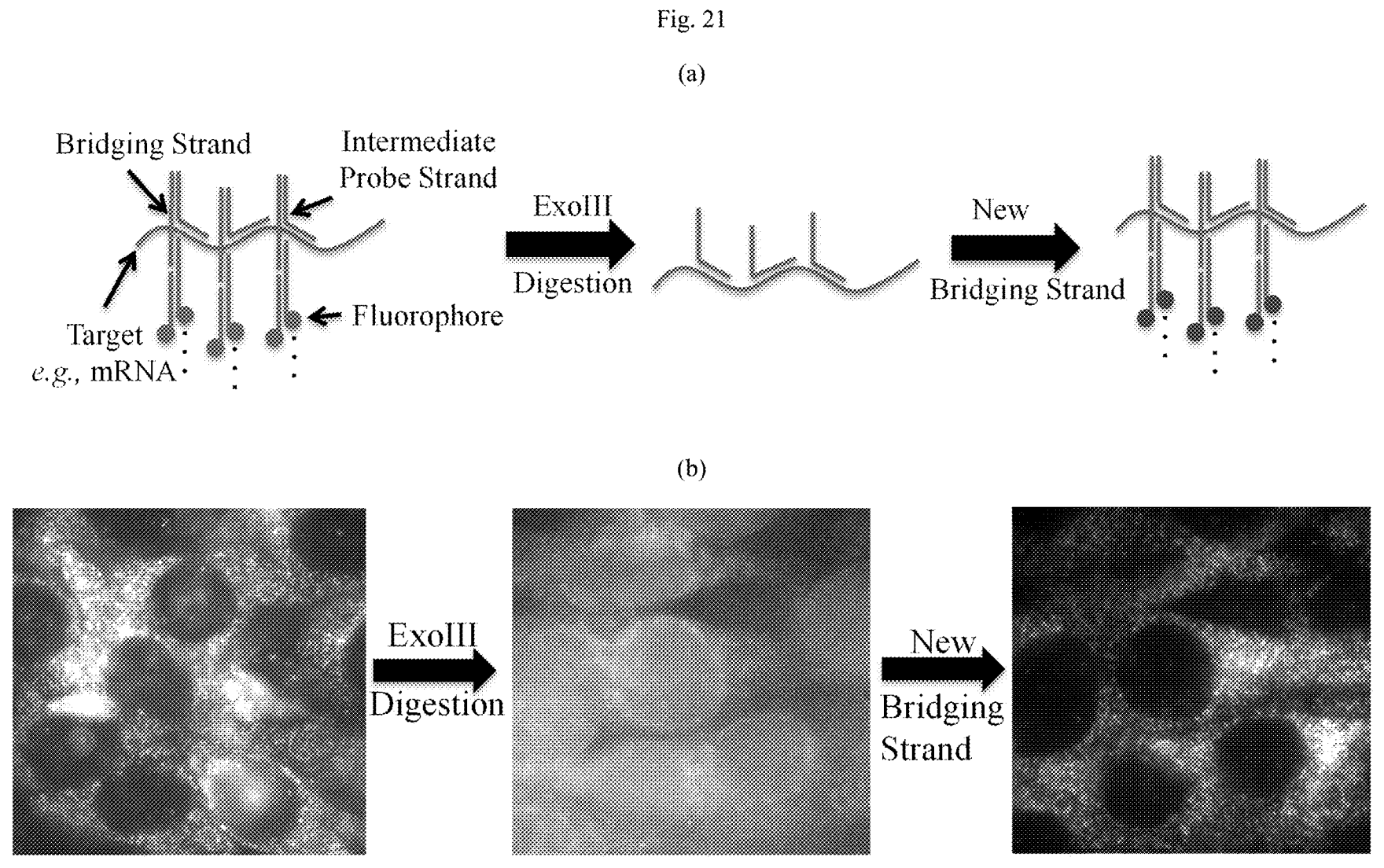

In some embodiments, the present invention provides a varieties of methods for removing detectably labeled oligonucleotides from targets. In some embodiments, exonuclease III (ExoIII) is used to remove detectably labeled oligonucleotides. FIG. 21 illustrates an exemplary process for HCR re-hybridization using Exo III. In FIG. 21, Exo III digests bridging strands and HCR polymers, keeping intermediate oligonucleotides intact for hybridization with new bridging strands. Exemplary data were presented in FIG. 21 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed complete loss of signal in the Alexa 488 channel after a 1 hour incubation in exoIII at room temperature. The right image showed re-amplification of Actb transcripts after addition of only the new bridging strand and the corresponding hairpins tagged with Alexa 647 dye. The contrast ratio of the images was adjusted to illustrate certain features of the method.

Figure 22:
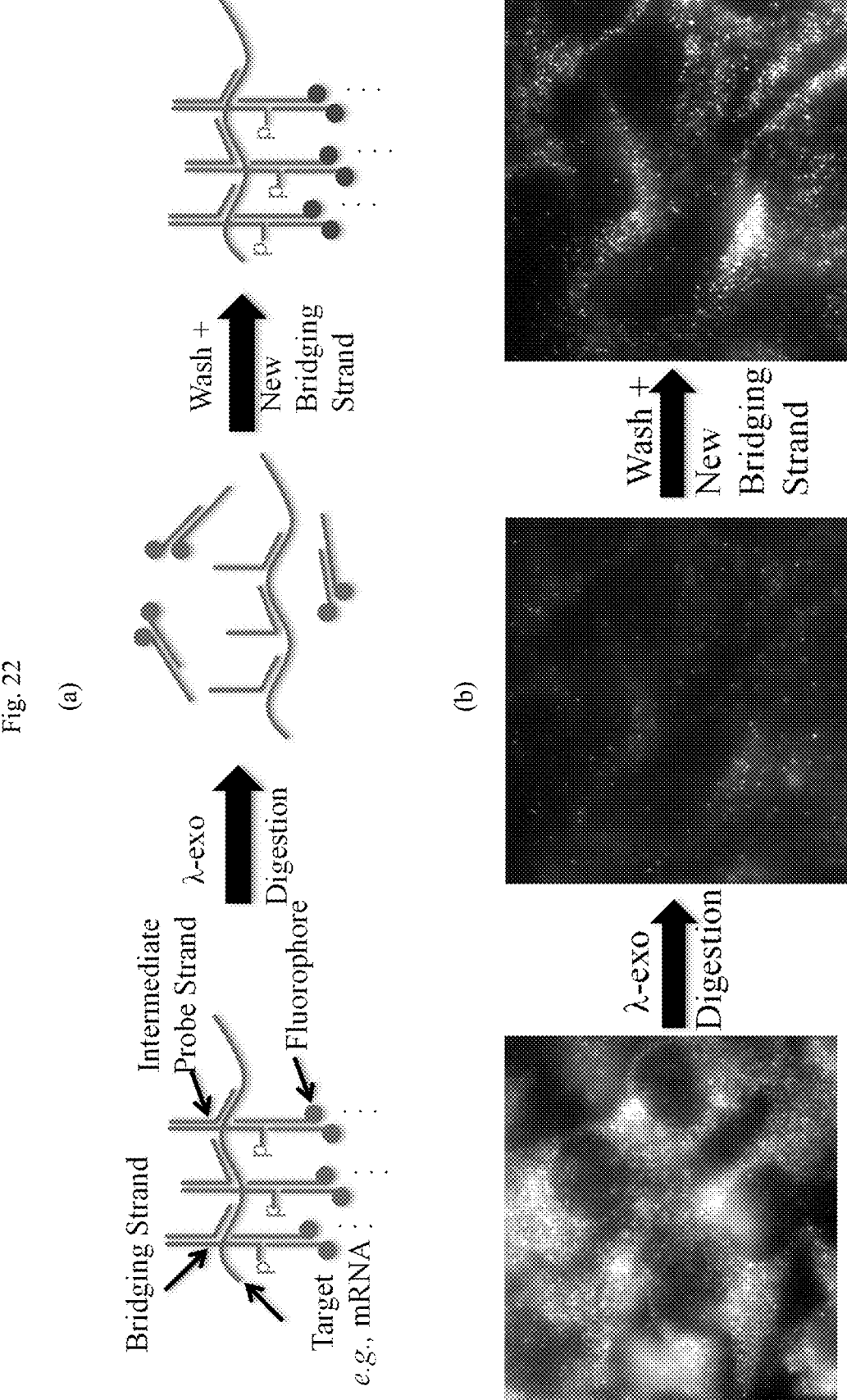
FIG. 22. Hybridization Chain Reaction (HCR) Re-hybridization Using Lambda Exonuclease (λ-exo). (a) Schematic representation of k-exo digestion of bridging strands. λ-exo selectively digests 5' phosphorylated bridging strands in the 5' to 3' direction releasing HCR polymers from intermediate probe strands bound to targets, e.g., mRNAs. Released polymers are washed out with wash buffer. A new bridging strand can then by hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

In some embodiments, Lambda Exonuclease (k-exo) is used to remove detectably labeled oligonucleotides. FIG. 22 illustrates an exemplary process for HCR re-hybridization using k-exo. In FIG. 22, k-exo digests 5' phosphorylated bridging strands and releases HCR polymers from intermediate oligonucleotides bound to targets, e.g., mRNAs and keeps intermediate oligonucleotides intact for hybridization with new bridging strands after washing out released polymers. Exemplary data were presented in FIG. 22 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed loss of signal in the Alexa 488 channel after a 1 hour incubation in k-exo at 37° C. The right image showed re-amplification of Actb transcripts after washing with wash buffer and addition of only the new bridging strand along with the corresponding hairpins tagged with Alexa 647 dye. The contrast ratio of the images was adjusted to illustrate certain features of the method.

Figure 23:
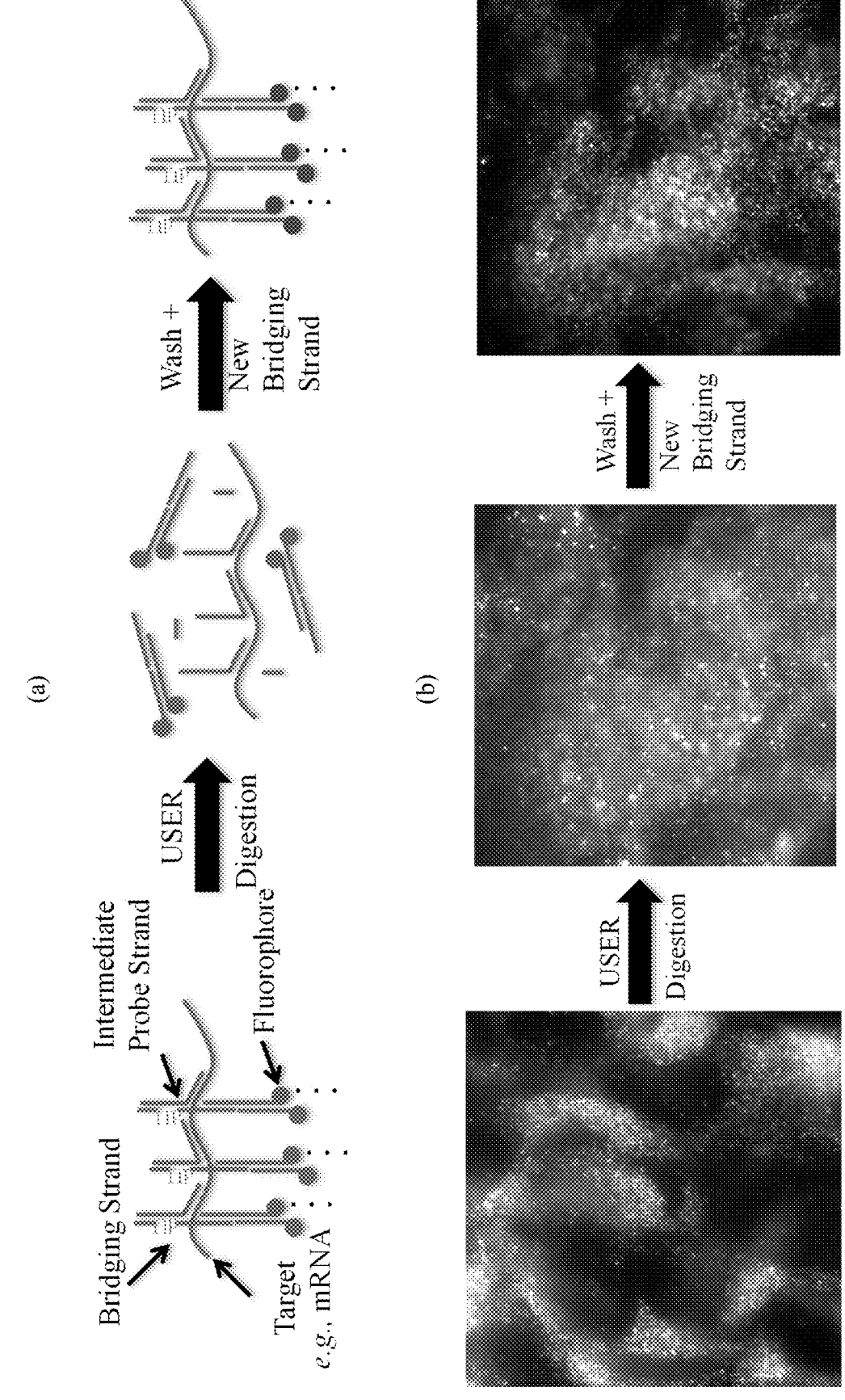
FIG. 23. Hybridization Chain Reaction (HCR) Re-hybridization Using Uracil-Specific Excision Reagent (USER). (a) Schematic representation of USER digestion of bridging strands. USER selectively digests deoxyuridine nucleotides in bridging strands causing bridging strands to become fragmented. Fragments then dissociate from intermediate probe strands releasing HCR polymers from probes bound to targets, e.g., mRNAs. Released polymers are washed out with wash buffer. A new bridging strand can then be hybridized to target bound probe with a different initiator sequence which initiates polymerization of a different hairpin set with a different fluorescent dye. (b) Raw data illustrating use of the schematic shown in (a) in T3T mouse fibroblast cell line using probes against beta-actin (Actb) transcripts.

In some embodiments, Uracil-Specific Excision Reagent (USER) is used to remove detectably labeled oligonucleotides. FIG. 23 illustrates an exemplary process for HCR re-hybridization using USER. In FIG. 23, USER digests at deoxyuridine nucleotides in bridging strands and releases HCR polymers from intermediate oligonucleotides bound to targets, e.g., mRNAs and keeps intermediate oligonucleotides intact for hybridization with new bridging strands after washing out fragments and released polymers. Exemplary data were presented in FIG. 23 (b) using detectably labeled oligonucleotides targeting beta-actin (Actb) transcripts in T3T mouse fibroblast cells. The left image showed the initial hybridization and amplification of Actb transcripts using Alexa 488 dye. The middle image showed loss of signal in the Alexa 488 channel after a 1 hour incubation in USER at 37° C. The right image showed re-amplification of Actb transcripts after washing with wash buffer and addition of only the new bridging strand along with the corresponding hairpins tagged with Alexa 647 dye. The contrast ratio of the images was adjusted to illustrate certain features of the method.

Figure 24:
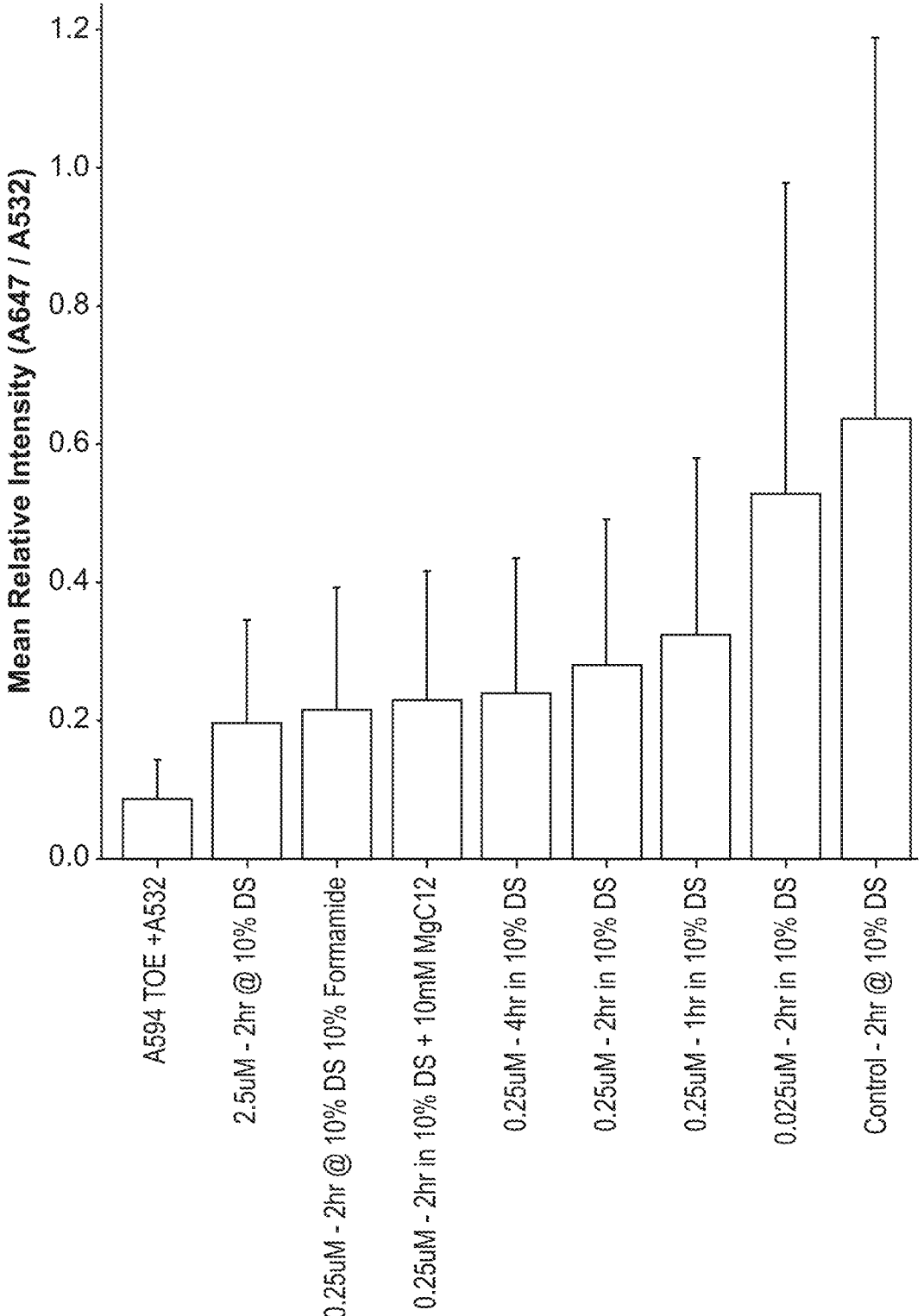
FIG. 24. Exemplary removal of detectably labeled oligonucleotides using complementary oligonucleotides (cTOE).

In some embodiments, detectably labeled oligonucleotides are removed by displacement using complementary oligonucleotides (cTOE). In some embodiments, displacement comprises use of a dextran or a derivative thereof, a salt, and/or an organic solvent. In some embodiments, displacement comprises use of a dextran or a derivative thereof. In some embodiments, displacement comprises use of dextran sulfate. In some embodiments, displacement comprises use of a salt. In some embodiments, a salt is $MgCl_2$. In some embodiments, displacement comprises use of an organic solvent. In some embodiments, an organic solvent is formamide. A variety of factors, for example but not limited to cTOE concentration, incubation time, buffer composition and type and/or concentration of organic solvent can be optimized individually or in combination. FIG. 24 showed exemplary data of displacement of smFISH probes using cTOE. The mean ratio of fluorescence intensity between the smFISH probe to be displaced (Alexa 647) and a colocalized smFISH probe (Alexa 532) is shown. Various treatments were performed in which the concentration of cTOE, hybridization buffer composition and displacement time were compared. All displacement probe conditions resulted in significantly more displacement than the control in which cells were placed in 10% DS and no cTOE was added. Without the intention to be limited by theory, Applicant notes that, among other things, increasing the concentration of cTOE, increasing the amount of time that cTOE probes hybridized, adjusting buffers to 10 mM $MgCl_2$ or 10% formamide all resulted in increased displacement. cTOE at 2.5 µM for 2 hours in 10% Dextran sulfate (DS) results in minimal residual Alexa 647 smFISH signal but a minor increase over the baseline signal determined by hybridizing Alexa 594(A594) in place of Alexa 647 and not adding cTOE.

Additional Examples for Oligonucleotide Preparation

Figure 26:
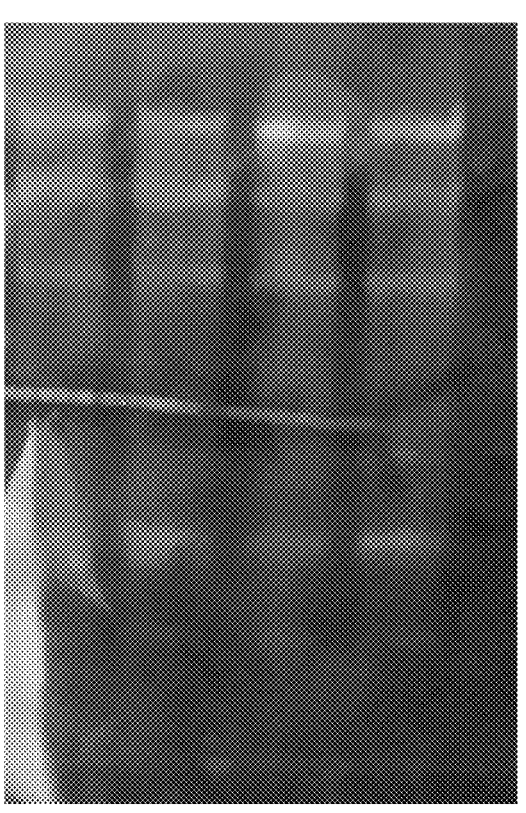
FIG. 26. Exemplary oligonucleotide preparation. Product was the third band on gel. The library has many different primers associated with it, one primer set for each subset of probes. Exemplified primers were random 20 nucleotide sequences with a GC content of 45-55% and a Tm of around 55° C. Nicking endonucleases sites were GTCTCNN; corresponding nicking endonuclease is Nt. BsmAI. Product probes were 20mer DNA sequences complementary to mRNA of interest with a GC content between 45-55%.

A set of sequences were amplified by PCR (FIG. 25). The product was isolated, e.g., precipitated using 5 volumes of precipitation buffer (30:1 EtOH: 1M NaOAc) at −20° C. for at least 10 minutes. The precipitation mixture was centrifuged for 10 minutes. The supernatant was discarded and the oligonucleotide pellet was reconstituted in nicking enzyme buffer with the appropriate units of enzyme, based on that about 10 units of enzyme digest about 1 µg of DNA in 1 hour. Once the incubation time had elapsed, the sample was again precipitated and reconstituted in 2× loading buffer (96% formamide/20 mM EDTA) and water to make a final loading buffer (48% formamide/10 mM EDTA). The sample was heated to 95° C. to completely denature the DNA. The denatured DNA was then loaded into a denaturing acrylamide gel (8M urea 10-12% acrylamide). The gel was run at 250V for 1 hour, or optimized as desired. After electrophoresis, the gel was stained using 1× sybr gold for 15 minutes and then visualized. The appropriate band was cut out, crushed, and incubated in DI water for 2 hours. After incubation, the sample was precipitated again and then purified using a vacuum column. The column was eluted with 30 µL of RNase free water to yield the final product, as shown in FIG. 26.

In some embodiments, provided methods use restriction sites instead of nicking endonuclease sites. Similar to the amplification step in FIG. 25, a set of sequences are amplified by PCR, with a BamHI site flanking the 5'-end, and an AatII site flanking the 3'-end. The PCR product is precipitated with 5 volumes of precipitation buffer (30:1 EtOH: 1M NaOAc) at −20° C. for at least 10 minutes and isolated, followed by digestion with BamHI and AatII. The product is again purified, and subjected to exo III digestion. Removal of the digested nucleic acids provides the product oligonucleotides.

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method, comprising steps of:
(a) contacting a sample comprising a plurality of target nucleic acids, proteins, or combination thereof, with a first plurality of detectably labeled proteins to form a composition, which composition comprises at least:
(i) a first detectably labelled protein that interacts with a first target nucleic acid, protein, or combination thereof; and
(ii) a second detectably labelled protein that interacts with a second target nucleic acid, protein, or combination thereof;

wherein the first detectably labelled protein is different from the second detectably labelled protein;
(b) imaging the sample after the first contacting step so that interactions of the detectably labelled proteins with their targets are detected;
(c) repeating the contacting and imaging steps, each time with a new plurality of detectably labelled proteins,
so that a target in the sample is described by a barcode, and can be differentiated from another target in the sample by a difference in their barcodes.

2. A method, comprising steps of:
(a) contacting a sample comprising a plurality of target nucleic acids, proteins, or combination thereof, with a first plurality of detectably labeled oligonucleotides to form a composition, which composition comprises at least:
(i) a first detectably labelled oligonucleotide that interacts with a first target nucleic acid, protein, or combination thereof; and
(ii) a second detectably labelled oligonucleotide that interacts with a second target nucleic acid, protein, or combination thereof;
wherein the first detectably labelled oligonucleotide is different from the second detectably labelled oligonucleotide;
(b) imaging the sample after the first contacting step so that interactions of the detectably labelled oligonucleotides with their targets are detected;
(c) repeating the contacting and imaging steps, each time with a new plurality of detectably labelled oligonucleotides,
so that a target in the sample is described by a barcode, and can be differentiated from another target in the sample by a difference in their barcodes.

3. The method of claim 1, wherein each plurality of detectably labeled proteins comprises F detectable moieties, wherein F is at least two.

4. The method of claim 1, comprising N contacting steps, wherein N is at least two.

5. The method of claim 1, wherein each plurality of detectably labelled proteins targets $(F)^N$ transcripts, DNA loci, proteins, or combination thereof.

6. The method of claim 1, wherein each plurality of detectably labelled proteins targets less than $(F)^N$ transcripts, DNA loci, proteins, or combination thereof.

7. The method of claim 1, optionally comprising a step of removing a plurality of detectably labeled proteins after an imaging step.

8. The method of claim 1, comprising a step of removing a plurality of detectably labeled proteins after each imaging step.

9. The method of claim 8, wherein the step of removing comprises contacting the plurality of detectably labeled proteins with an enzyme that digests detectable moieties.

10. The method of claim 1, wherein the detectably labelled protein is a detectably labelled antibody.

11. The method of claim 8, wherein the step of removing comprises photobleaching.

12. The method of claim 1, wherein each plurality comprises two or more detectably labeled proteins targeting the same transcript, or DNA locus loci.

13. The method of claim 12, wherein all detectably labeled proteins targeting the same transcript or DNA locus are labelled with a fluorophore providing the same color.

14. The method of claim 12, wherein all detectably labeled proteins targeting the same transcript or DNA locus are labelled with the same fluorophore.

15. The method of claim 1, wherein the third protein is labeled with a different detectable moiety than was the first protein, and the fourth protein is labeled with the same detectable moiety as was the second protein; or the third protein is labeled the same detectable moiety as was the first protein, and the fourth protein is labeled with a different detectable moiety than was the second protein.

16. The method of claim 1, wherein the third protein is labeled with a different detectable moiety than was the first protein, and the fourth protein is labeled with a different detectable moiety than was the second protein.

17. The method of claim 1, wherein an imaging step comprises imaging the cell after a contacting step so that interaction by a plurality of detectably labeled proteins with their targets is quantified.

18. The method of claim 1, wherein the detectably labelled proteins interact with target nucleic acids.

19. The method of claim 18, wherein the detectably labelled proteins are antibodies.

20. The method of claim 2, wherein a detectably labeled oligonucleotide interacts with its target through an intermediate oligonucleotide, bound, hybridized, or specifically linked to a target.

21. The method of claim 20, wherein the intermediate oligonucleotide comprises a sequence complementary to its target nucleic acid and an overhang sequence.

22. The method of claim 21, wherein the overhang sequences are complementary to one or more bridge oligonucleotides.

23. The method of claim 22, wherein one or more bridge oligonucleotides binds, hybridizes, or links, to a detectably labelled oligonucleotide.

24. The method of claim 20, wherein the intermediate oligonucleotides are preserved through multiple contacting and imaging steps.

25. The method of claim 20, wherein each detectably labelled oligonucleotide interacts with its target through one or more intermediate oligonucleotides each of which hybridized to the target.

26. The method of claim 21, wherein each detectably labelled oligonucleotide interacts with its target through one or more bridge oligonucleotides.

27. The method of claim 2, wherein each of the first and second target nucleic acids is a transcript.

28. The method of claim 27, wherein each of the first and second detectably labeled oligonucleotides interacts with its target via an intermediate oligonucleotide that hybridized to the target.

29. The method of claim 2, wherein:

the first detectably labelled oligonucleotide interacts with the first target nucleic acid;

the second detectably labelled oligonucleotide interacts with the second target nucleic acid;

each of the first target nucleic acid and second target nucleic acid is a nucleic acid within a cell;

and each of the first and second target nucleic acids is described by a barcode, and can be differentiated from each other by a difference in their barcodes.

30. The method of claim 29, wherein each of the first and second target nucleic acids is a transcript.

31. The method of claim 29, wherein each of the first and second detectably labeled oligonucleotides interacts with nucleic acids obtained by subjecting the intermediate oligonucleotide to amplification.

32. The method of claim 31, wherein each of the first and second detectably labelled oligonucleotides comprises a fluorophore that is bound to the oligonucleotide.

33. The method of claim 29, further comprising a step of removing the plurality of detectably labeled oligonucleotides after each imaging step.

34. The method of claim 32, wherein the step of removing comprises photobleaching.

35. The method of claim 2, further comprising:

(a) contacting the sample with a first plurality of detectably labeled oligonucleotides, so that the composition comprises at least:

(i) the first detectably labelled oligonucleotide that interacts with a first target protein; and (ii) the second detectably labelled oligonucleotide that interacts with a second target protein;

wherein the first detectably labelled oligonucleotide is different from the second detectably labelled oligonucleotide;

(b) imaging the sample so that interactions of the detectably labelled oligonucleotides with their targets are detected;

(c) repeating the contacting and imaging steps, each time with a new plurality of detectably labelled proteins, so that each of the first and second target proteins are described by a barcode, and can be differentiated from each other by a difference in their barcodes.

36. The method of claim 20, wherein each of the first and second detectably labeled oligonucleotides interacts with its target through nucleic acids obtained by subjecting the intermediate oligonucleotide to amplification.

37. The method of claim 29, wherein each of the first and second target nucleic acids is a nucleic acid produced by amplification.

38. The method of claim 28, wherein each of the first and second detectably labeled oligonucleotides interacts with its target via nucleic acids obtained by subjecting the intermediate oligonucleotide to amplification.

39. The method of claim 37, wherein the first detectably labeled oligonucleotide targets the first target nucleic acid and is labeled with a first detectable moiety, and the second detectably labeled oligonucleotide targets the second target nucleic acid and is labeled with a second detectable moiety.

40. The method of claim 39, wherein each of the first and second detectably labeled oligonucleotides is at least 10 nucleotides in length.

41. The method of claim 35, wherein:

each of the first and second target proteins is an antibody; and each of the first and second detectably labeled oligonucleotides interacts with its target antibody via nucleic acids obtained by subjecting an intermediate oligonucleotide on the antibody to amplification.

42. The method of claim 2, wherein each of the first and second target nucleic acids is a DNA locus.

43. The method of claim 42, wherein each of the first and second detectably labeled oligonucleotides interacts with its target via an intermediate oligonucleotide that hybridized to the target.

44. The method of claim 43, wherein each of the first and second detectably labeled oligonucleotides interacts with its target via nucleic acids obtained by subjecting the intermediate oligonucleotide to amplification.

45. The method of claim 2, wherein at least one barcode includes no signal for one or more of the contacting steps.

46. The method of claim 2, further comprising a step of removing the plurality of detectably labeled oligonucleotides after each imaging step.

47. The method of claim 46, wherein the step of removing comprises photobleaching or contacting the plurality of detectably labeled oligonucleotide with an enzyme that digests detectable moieties.

* * * * *